US011198723B2

(12) United States Patent
Branco et al.

(10) Patent No.: US 11,198,723 B2
(45) Date of Patent: Dec. 14, 2021

(54) ARENAVIRUS MONOCLONAL ANTIBODIES AND USES

(71) Applicants: THE ADMINISTRATORS OF THE TULANE EDUCATIONAL FUND, New Orleans, LA (US); THE SCRIPPS RESEARCH INSTITUTE, La Jolla, CA (US); THE BOARD OF REGENTS OF THE UNIVERSITY OF TEXAS SYSTEM, Austin, TX (US); ZALGEN LABS, LLC, Germantown, MD (US)

(72) Inventors: Luis M. Branco, Germantown, MD (US); Robert F. Garry, New Orleans, LA (US); James E. Robinson, New Orleans, LA (US); Erica O. Saphire, La Jolla, CA (US); Kathryn M. Hastie, La Jolla, CA (US); Thomas W. Geisbert, Albany, TX (US)

(*) Notice: Subject to any disclaimer, the term of this patent is extended or adjusted under 35 U.S.C. 154(b) by 0 days.

(21) Appl. No.: 16/466,544

(22) PCT Filed: Dec. 5, 2017

(86) PCT No.: PCT/US2017/064744
§ 371 (c)(1),
(2) Date: Jun. 4, 2019

(87) PCT Pub. No.: WO2018/106712
PCT Pub. Date: Jun. 14, 2018

(65) Prior Publication Data
US 2020/0002405 A1    Jan. 2, 2020

Related U.S. Application Data

(60) Provisional application No. 62/430,225, filed on Dec. 5, 2016.

(51) Int. Cl.
*C07K 16/10* (2006.01)
*A61P 31/14* (2006.01)

(52) U.S. Cl.
CPC .............. *C07K 16/10* (2013.01); *A61P 31/14* (2018.01); *C07K 2317/21* (2013.01); *C07K 2317/31* (2013.01); *C07K 2317/33* (2013.01); *C07K 2317/565* (2013.01); *C12N 2760/10011* (2013.01)

(58) Field of Classification Search
CPC .............. C07K 16/10; C12N 2760/10011
See application file for complete search history.

(56) References Cited

U.S. PATENT DOCUMENTS

| 4,816,567 A | 3/1989 | Cabilly et al. |
| 5,219,740 A | 6/1993 | Miller et al. |
| 5,422,120 A | 6/1995 | Kim |
| 5,530,101 A | 6/1996 | Queen et al. |
| 5,565,332 A | 10/1996 | Hoogenboom et al. |
| 5,580,717 A | 12/1996 | Dower et al. |
| 5,580,859 A | 12/1996 | Felgner et al. |
| 5,585,362 A | 12/1996 | Wilson et al. |
| 5,693,762 A | 12/1997 | Queen et al. |
| 5,733,743 A | 3/1998 | Johnson et al. |
| 5,807,715 A | 9/1998 | Morrison et al. |
| 5,866,692 A | 2/1999 | Shitara et al. |
| 6,180,370 B1 | 1/2001 | Queen et al. |
| 6,265,150 B1 | 7/2001 | Terstappen et al. |
| 6,331,415 B1 | 12/2001 | Cabilly et al. |
| 6,376,471 B1 | 4/2002 | Lawrence, III et al. |
| 6,413,942 B1 | 7/2002 | Felgner et al. |
| 6,436,908 B1 | 8/2002 | Koch et al. |
| 2014/0271580 A1 | 9/2014 | Garry et al. |

FOREIGN PATENT DOCUMENTS

| CN | 105296507 A | 2/2016 |
| CN | 105548539 A | 5/2016 |
| WO | 20080124176 A2 | 10/2008 |

OTHER PUBLICATIONS

Lukashevich, I. S., 2012, Advanced vaccine candidates for lassa fever, Viruses 4:2514-2557.*
Zapata, J. C., et al., 2018, Improving the breadth of the host's immune response to lassa virus, Pathogens 7, 84:doi:10.3390/pathogens7040084, pp. 1-18.*
Both, L., et al., 2013, Monoclonal antibodies for prophylactic and therapeutic use against viral infections, Vaccine 31:1553-1559.*
Cross, R. W., et al., 2019, Antibody therapy for lassa fever, Curr. Opin. Virol. 37:97-104.*
Zenke, M., et al., Receptor-Mediated Endocytosis of Transferrin-Polycation Conjugates: An Efficient Way to Introduce DNA Into Hematopoietic Cells, PNAS 87, 3655-3659 (1990).
Andersen, K.G. et al., Clinical Sequencing Uncovers Origins and Evolution of Lassa Virus, Cell 162, 738-750 (2015).
Auperin, D. D. et al., Nucleotide Sequence of the Glycoprotein Gene and Intergenic Region of the Lassa Virus S Genome RNA, Virology 154, 155-167 (1986).
Beyer, W.R. et al., Endoproteolytic Processing of the Lymphocytic Choriomeningitis Virus Glycoprotein by the Subtilase SKI-1/S1P, Journal of Virology 77 (5), 2866-2872 (2003).

(Continued)

*Primary Examiner* — Jeffrey S Parkin
(74) *Attorney, Agent, or Firm* — Olson & Cepuritis, Ltd.

(57) ABSTRACT

Disclosed herein are compositions comprising arenavirus monoclonal antibodies, as well as therapeutic, diagnostic, and preventative methods using the novel antibodies. Preventative methods include preparation of vaccines, as well as factors (e.g. small molecules, peptides) that inhibit Old World arenavirus infectivity, including LASV and LCMV. In some embodiments, the antibodies provide pan-arenavirus protection against a number of arenavirus types and strains. Diagnostic and therapeutic antibodies including neutralizing antibodies for the prevention and treatment of infection by LASV and other arenaviruses are also disclosed, as well as new tools and methods for the design, production, and use of arenavirus monoclonal antibodies, including expression in engineered bacterial- and mammalian-based systems.

13 Claims, 10 Drawing Sheets

Specification includes a Sequence Listing.

(56) References Cited

OTHER PUBLICATIONS

Branco, L.M. et al., Lassa Virus-Like Particles Displaying All Major Immunological Virology Determinants as a Vaccine Candidate for Lassa Hemorrhagic Fever, Virology Journal 7 (279), 1-19 (2010).
Branco, L.M. et al., Emerging Trends in Lassa Fever: Redefining the Role of Immunoglobulin M and Inflammation in Diagnosing Acute Infection, Virology Journal 8 (478), 1-15 (2011).
Buchmeier, M.J. et al., Monoclonal Antibodies to Lymphocytic Choriomeningitis Virus React With Pathogenic Arenaviruses, Nature 288, 486-487 (1980).
Buchmeier, M.J. et al., Arenaviruses: Protein Structure and Function, Current Topics in Microbiology and Immunology, 288, 159-173 (2002).
Buck, D.W. et al., Monoclonal Antibodies Specific for Cell Culture Mycoplasmas, In Vitro 18 (4), 377-381 (1982).
Burnette, W.N., Western Blotting: Electrophoretic Transfer of Proteins From Sodium Dodecyl Sulfate—Polyacrylamide Gels to Unmodified Nitrocellulose and Radiographic Detection With Antibody and Radioiodinated Protein A, Analytical Biochemistry 112, 195-203 (1981).
Chiou, H.C. et al., In Vivo Gene Therapy Via Receptor-Mediated DNA Delivery, Gene Therapeutics: Methods and Applications of Direct Gene Transfer 141-156, Birkhauser Boston (1994).
Clegg, J.C.S. et al., Structural and Cell-Associated Proteins of Lassa Virus, Journal General Virology 64, 1127-1136 (1983).
Curiel, D.T. et al., High-Efficiency Gene Transfer Mediated by Adenovirus Coupled to DNA-Polylysine Complexes, Human Gene Therapy 3, 147-154 (1992).
Dayhoff, M.O. et al., A Model of Evolutionary Change in Proteins, Atlas of Protein Sequence and Structure, 345-358 (1978).
Eichler, R. et al., Lassa Virus Glycoprotein Signal Peptide Displays a Novel Topology With an Extended Endoplasmic Reticulum Luminal Region, The Journal of Biological Chemistry 279 (13), 12293-12299 (2004).
Eichler, R. et al., Identification of Lassa Virus Glycoprotein Signal Peptide as a Trans-Acting Maturation Factor, EMBO Reports 4 (11), 1084-1088 (2003).
Eichler, R. et al., Signal Peptide of Lassa Virus Glycoprotein GP-C Exhibits an Unusual Length, FEBS Letters 538, 203-206 (2003).
Elagoz, A. et al., Biosynthesis and Cellular Trafficking of the Convertase SKI-1-S1P, The Journal of Biological Chemistry 277 (13), 11265-11275 (2002).
Findeis, M.A. et al., Targeted Delivery of DNA for Gene Therapy Via Receptors, Trends Biotechnology 11, 202-205 (1993).
Grove, J.N. et al., Capacity Building Permitting Comprehensive Monitoring of a Severe Case of Lassa Hemorrhagic Fever in Sierra Leone With a Positive Outcome: Case Report, Virology Journal 8 (314), 1-14 (2011).
Hartnett, J.N. et al., Current and Emerging Strategies for the Diagnosis, Prevention and Treatment of Lassa Fever, Future Virology 10 (5), 559-584 (2015).
Higgins, D.G. et al., Fast and Sensitive Multiple Sequence Alignments on a Microcomputer, Cabios Communications 5 (2), 151-153 (1989).
Hufert, F.T. et al., Epitope Mapping of the Lassa Virus Nucleoprotein Using Monoclonal Anti-Nucleocapsid Antibodies, Arch Virology 106, 201-212 (1989).
Johnson, K.S. et al., Human Antibody Engineering, Current Opinion in Structural Biology 3, 564-571 (1993).
Kohler, G. et al., Continuous Cultures of Fused Cells Secreting Antibody of Predefined Specificity, Nature 256, 495-497 (1975).
Lenz, O. et al., Identification of a Novel Consensus Sequence at the Cleavage Site of the Lassa Virus Glycoprotein, Journal of Virology 74 (23), 11418-11421 (2000).
Lonberg, N. et al., Human Antibodies From Transgenic Mice, International Reviews of Immunology 13, 65-93 (1995).
Lukashevich, I.S. et al., Lassa Virus Activity in Guinea: Distribution of Human Antiviral Antibody Defined Using Enzyme-Linked Immunosorbent Assay With Recombinant Antigen, Journal of Medical Virology 40, 210-217 (1993).
McCafferty, J. et al., Phage Antibodies: Filamentous Phage Displaying Antibody Variable Domains, Nature 348, 552-554 (1990).
McCormick, J.B. et al., Lassa Fever, Current Topics in Microbiology and Immunology 262, 75-109 (2002).
Meulen, J.T. et al., Characterization of Human CD4+ T-Cell Clones Recognizing Conserved and Variable Epitopes of the Lassa Virus Nucleoprotein, Journal of Virology 74 (5), 2186-2192 (2000).
Meulen, J.T. et al., Detection of Lassa Virus Antinucleoprotein Immunoglobulin G (IgG) and IgM Antibodies by a Simple Recombinant Immunoblot Assay for Field Use, Journal of Clinical Microbiology 36 (11), 3143-3148 (1998).
Myers, E.W. et al., Optimal Alignments in Linear Space, CABIOS 4 (1) 11-17 (1988).
Peeters, K. et al., Production of Antibodies and Antibody Fragments in Plants, Vaccine 19 2756-2761 (2001).
Philip, R. et al., Efficient and Sustained Gene Expression in Primary T Lymphocytes and Primary and Cultured Tumor Cells Mediated by Adeno-Associated Virus Plasmid DNA Complexed to Cationic Liposomes, Molecular and Cellular Biology 14 (4), 2411-2418 (1994).
Pollock, D.P. et al., Transgenic Milk as a Method for the Production of Recombinant Antibodies, Journal of Immunological Methods 231, 147-157 (1999).
Robinson, D.F., Comparison of Labeled Trees With Valency Three, Journal of Combinatorial Theory 11, 105-119 (1971).
Ruo, S.L. et al., Antigenic Relatedness Between Arenaviruses Defined at the Epitope Level by Monoclonal Antibodies, Journal of General Virology 72, 549-555 (1991).
Saitou, N. et al., The Neighbor-Joining Method: A New Method for Reconstructing Phylogenetic Trees, Molecular Biology Evol. 4 (4):406-425 (1987).
Sanchez, A. et al., Junin Virus Monoclonal Antibodies: Characterization and Cross-Reactivity With Other Arenaviruses, Journal General Virology 70, 1125-1132 (1989).
Shaffer, J.G. et al., Lassa Fever in Post-Conflict Sierra Leone, PLOS Neglected Tropical Diseases 8 (3), e2748, 1-12 (2014).
Spiropoulou, C.F. et al., New World Arenavirus Clade C, But Not Clade A and B Viruses, Utilizes a-Dystroglycan as Its Major Receptor, Journal of Virology 76 (10), 5140-5146 (2002).
Wilbur, W.J. et al., Rapid Similarity Searches of Nucleic Acid and Protein Data Banks, PNAS 80, 726-730 (1983).
Winter, G. et al., Making Antibodies by Phage Display Technology, Annual Review Immunology 12, 433-455 (1994).
Woffendin, C. et al., Nonviral and Viral Delivery of a Human Immunodeficiency Virus Protective Gene Into Primary Human T Cells, PNAS 91, 11581-11585 (1994).
Wu, G.Y. et al., Receptor-Mediated Gene Delivery in Vivo, Partial Correction of Genetic Analbuminemia in Nagase Rats, The Journal of Biological Chemistry 266 (22), 14338-14342 (1991).
Wu, G.Y. et al., Receptor-Mediated Gene Delivery and Expression in Vivo, The Journal of Biological Chemistry 263 (29), 14621-14624 (1988).
Wu, C.H., et al., Targeting Genes: Delivery and Persistent Expression of a Foreign Gene Driven by Mammalian Regulatory Elements in Vivo, The Journal of Biological Chemistry 264 (29), 16985-16987 (1989).
Wu, G.Y. et al., Incorporation of Adenovirus Into a Ligand-based DNA Carrier System Results in Retention of Original Receptor-Mediated Specificity and Enhances Targeted Gene Expression, The Journal of Biological Chemistry 269 (15), 11542-11546 (1994).
York, J. et al., Genetic Analysis of Heptad-Repeat Regions in the G2 Fusion Subunit of the Junin Arenavirus Envelope Glycoprotein, Virology 343, 267-274 (2005).
York, J. et al., The Signal Peptide of the Junin Arenavirus Envelope Glycoprotein is Myristoylated and Forms an Essential Subunit of the Mature G1-G2 Complex, Journal of Virology 78 (19), 10783-10792 (2004).
Fisher-Hoch, S.P. et al., Effective Vaccine for Lassa Fever, Journal of Virology 74 (15), 6777-6783 (2000).
Robinson, J.E. et al., Most Neutralizing Human Monoclonal Antibodies Target Novel Epitopes Requiring Both Lassa Virus Glycoprotein Subunits, Nature Communications 7 (11544), 1-14 (2016).

(56) References Cited

OTHER PUBLICATIONS

Branco, L.M. et al., Shedding of Soluble Glycoprotein 1 Detected During Acute Lassa Virus Infection in Human Subjects, Virology Journal 7 (1), Biomed Central, London, GB, 306 (2010).

Buchmeier, M.J. et al., Monoclonal Antibodies to Lymphocytic Choriomeningitis and Pichinide Viruses: Generation, Characterization, and Cross-Reactivity With Other Arenaviruses, Virology 113 (1), 73-85 (1981).

Cross, R.W. et al., Treatment of Lassa Virus Infection in Outbred Guinea Pigs With First-in-Class Human Monoclonal Antibodies, Antiviral Research 133, 218-222 (2016).

Hastie, K.M. et al., Structural Basis for Antibody-Mediated Neutralization of Lassa Virus, Science 356 (6341), 923-928 (2017).

Mahmutovic, S. et al., Molecular Basis for Antibody-Mediated Neutralization of New World Hemorrhagic Fever Mammarenaviruses, Cell Host & Microbe 18 (6), 705-713 (2015).

Mire, C.E., Human-Monoclonal-Antibody Therapy Protects Nonhuman Primates Against Advanced Lassa Fever, Nature Medicine 23 (10) 1146-1149 (2017).

Robinson, J.E. et al., Supplementary Information for Most Neutralizing Human Monoclonal Antibodies Target Novel Epitopes Requiring Both Lassa Virus Glycoprotein Subunits, Nature Communications 7, 1-13 (2016).

\* cited by examiner

Antibody:
- ● 9.7A
- ■ 12.1F
- ▲ 13.4E
- ▼ 37.7H

- ■ no mAb
- ▼ 37.7H

```
                                                                CDR1: ++++++++++
10.4B    METDTLLLWVLLLWVPGSTGDQVQLVQSGGGVVQPGRSLRVSCVTSGFNF-RAYGMHWVR
19.7E    METDTLLLWVLLLWVPGSTGDEVQLVESGGGLVRPGGSLRLSCAASGFSF-SSYSMHWVR
2.9D     METDTLLLWVLLLWVPGSTGDEVQLVESGGGLVKPGGSLRLSCAASGFTF-TRFTLTWVR
25.6A    METDTLLLWVLLLWVPGSTGDQVQLQESGGGLVKAGGSLRLSCAASGFMF-ERYSLHWVR
36.1F    METDTLLLWVLLLWVPGSTGDQVQLQESGAGLVKPSETLSLTCAVSGGPF-SGAYWTWIR
36.9F    METDTLLLWVLLLWVPGSTGDEVQLVQSGGGLVKAGGSLKLSCGASGFTF-SSYSMSWVR
37.2D    METDTLLLWVLLLWVPGSTGDEVQLVQSGAEVKKPGASVKVSCKASGYTF-TKYGISWVR
37.2G    METDTLLLWVLLLWVPGSTGDEVQLVESGGGLVKPGGSRRLSCAASGFTF-SRDTMTWVR
37.7H    METDTLLLWVLLLWVPGSTGDEVQLVQSGGGLVKAGGSLRLSCAASGFTF-STYSMNWIR
8.9F     METDTLLLWVLLLWVPGSTGDQGTLRESGPGLVRPSETLSLTCGVSGYSISSGYYWGWIR
NE13     METDTLLLWVLLLWVPGSTGDEVQLVESGGGLVKPGGSLRLSCVASGFTF-SSYSMNWVR
12.1F    METDTLLLWVLLLWVPGSTGDQVQLQESGAGLLKPSETLSLSCTVDGESF-NGFFWTWIR
9.8A     METDTLLLWVLLLWVPGSTGDEVQLVQSGGRLVQPGGSLRLSCVASGFTF-SSHAMSWVR
18.5C    METDTLLLWVLLLWVPGSTGDEVQLVESGGGLVRPGGSLRLSCAAAGFTF-KSYSMNWVR
8.11G    METDTLLLWVLLLWVPGSTGDQVQLQESGPGLVKPSETLSLTCSISGVST-RNYYWSWIR
25.10C   METDTLLLWVLLLWVPGSTGDQVQLQESGGGLVKPGGSLRLSCTASGFNF-NKYNMNWVR
         ********************:  *  :**     :   :  : ::*    *        *;*

CDR2: ^^^^^^^^^                                  CDR3: #
10.4B    QIPGKGLEWVADIWSA-ETNRHYADSVKGRFTISRDNSKSTLYLQMNSLRAEDTGVYFCA
19.7E    HVPGKGLVWVSYINSD-GSTKIYADSVKGRFSISRDNAKNKLYLQMDSLRVEDTAVYSCV
2.9D     QAPGKGLEWVSSISS-GSSDINYADSVKGRFTISRDNARNSLFLQMSSLRVDDTAVYYCA
25.6A    QTPGKGLEWVSSISSLSGSHINYADSVKGRFTISRDNAKNSLSLQMNSLRVEDTAIYYCA
36.1F    QTPGKGLEWIGEAGRS--GTTNYNPSLKSRVTISLDTSKSQFSLKLTSVTAADTAVYFCG
36.9F    QAPGKGLEWVSYISS-GGSSIHYADSVKGRFTISRDNAKNSLYLQMKNLRVDDTGRYYCV
37.2D    QAPGQGLEWMGWISAF-NGYTRYGQRFQGKVTMTTDTSTNTASLEVRTLTSNDTAVYYCA
37.2G    QAPGKGLEWVASISS-GSSDINYADSVKGRFTISRDNGKNSLYLHMNSLRADDTAIYYCA
37.7H    QAPGKGLEWVASISSRSGSHINYVDSVKGRFTISRDNARDLLYLQMNSLRVDDSALYYCA
8.9F     QPPGKGLEWIGNIYRS--GSTYYNPSLKSRVTVSIDTSKNQFSLKLNSVTAADTAVYYCA
NE13     QAPGKGLEWVSSISS-GSSYIEYADSVKGRLTISRDNAKKSLYLQLNSLRAEDTAVYYCA
12.1F    QPPGKGLEWIGEINHL--ASTGYNPSLKSRVTISVDTSKNQFSLKLTSVTAADTAVYYCA
9.8A     QAPGKGLEWVSGFSGS-SGTTKYADSVKGRFTISRDNSKKTLYLQMNSLRAEDTAVYYCA
18.5C    QAPGRGLEWVSSITS-GGSKTYYADVVKGRFTVSRDNAKQSLYLQMNSLRAEDTAIYFCA
8.11G    QSPGKGLEWIGYIFNI--GTTNYNPSLKSRLTISVDTSKNQFSLKITSVTAADTAVYYCA
25.10C   QAPGKGLEWVSSISAL-STYIYYADSLKGRFTVSRDNAKNSLFLQMNSLRDDDTAVYYCA
         :  **:** *:.            *   .:.:.::  *..  .    *.:  .:   *:. * *

CDR3:  ################################
10.4B    KARP----GY--------------DYVVDLWGQGTLVIVSSASTKGPSVFPLAPCSRSTS
19.7E    RLVHY-------------------DWSPFVWGQGTLVTVSSASTKGPSVFPLAPSSKSTS
2.9D     KDPRSGISG---------------RYGMDVWGQGTTVIVSSASTKGPSVFPLAPCSRSTS
25.6A    RDRRSGSS----------------PVPLDVWGQGTTVTVSSASTKGPSVFPLAPSSKSTS
36.1F    RRQIMSLSN---------------LYKRPVDSWGRGTPVIVSSASTKGPSVFPLAPSSKSTS
36.9F    RDPRSGISG---------------RYGMDVWGQGTTVTVSSASTKGPSVFPLAPSSKSTS
37.2D    RQYPDQYSSSGW-----------PRLFAMDVWGQGTTVIVSPASTKGPSVFPLAPSSKSTS
37.2G    RDPRSGISG---------------RYGMDVWGQGTTVTVSSASTKGPSVFPLAPSSKSTS
37.7H    RDRRSGTS----------------PLPLDVWGQGTTVTVFSASTKGPSVFPLAPSSKSTS
8.9F     RSGIKVADDYYYEMDVWGQGTDDYSYAMDVWGQGTTVTVSSASTKGPSVFPLAPSSKSTS
NE13     RHT-ARIDS---------------YHGMDVWGQGTTVTVSSASTKGPSVFPLAPSSKSTS
12.1F    RGYSYGFAW---------------PNYHYLDVWGKGTTVTVSSASTKGPSVFPLAPSSKSTS
9.8A     KGFSPFRGVQ--------------FPYFDYWGQGTLVTVSSASTKGPSVFPLAPSSKSTS
18.5C    RSLHSTSQ----------------PSYMDVWGRKITVIVSSASTKGPSVFPLAPSSKSTS
8.11G    SGFEYGDY----------------TFDYWGQGTPVTVSSASTKGPSVFPLAPSSKSTS
25.10C   REIRRAS-----------------TWSADLWGRGTLVTVSSASTKGPSVFPLAPSSKSTS
                                  **:    *  *  *************.*.***
```

FIG. 7

```
10.4B    GGTAALGCLVKDYFPEPVTVSWNSGALTSGVHTFPAVLQSSGL-------------------
19.7E    GGTAALGCLVKDYFPEPVTVSWNSGALTSGVHTFPAVLQSSGLYSLSSVVTVPSSSLGTQ
2.9D     GGTAALGCLVKDYFPEPVTVSWNSGALTSGVHTFPAVLQSSGLYSLSSVVTVPSSSLGTQ
25.6A    GGTAALGC----------------------------------------------------
36.1F    GGTAALGCLVKDYFPEPVTVSWNSGALTSGVHTFPAVLQSSGLYSLSSVVTVPSSSLGTQ
36.9F    GGTAALGCLVKDYFPEPVTVSWNSGALTSGVHTFPAVLQSSGLYSLSSVVTVPSSSLGTQ
37.2D    GGTAALGCLVKDYFPEPVTVSWNSGALTSGVHTFPAVLQSSGLYSLSSVVTVPSSSLGTQ
37.2G    GGTAALGCLVKDYFPEPVTVSWNSGALTSGVHTFPAVLQSSGLYSLSSVVTVPSSSLGTQ
37.7H    GGTAALGCLVKDYFPEPVTVSWNSGALTSGVHTFPAVLQSSGLYSLSSVVTVPSSSLGTQ
8.9F     GGTAALGCLVKDYFPEPVTVSWNSGALTSGVHTFPAVLQSSGLYSLSSVVTVPSSSLGTQ
NE13     GGTAALGCLVKDYFPEPVTVSWNSGALTSGVHTFPAVLQSSGLYSLSSVVTVPSSSLGTQ
12.1F    GGTAALGCLVKDYFPEPVTVSWNSGALTSGVHTFPAVLQSSGLYSLSSVVTVPSSSLGTQ
9.8A     GGTAALGCLVKDYFPEPVTVSWNSGALTSGVHTFPAVLQSSGLYSLSSVVTVPSSSLGTQ
18.5C    GGTAALGCLVKDYFPEPVTVSWNSGALTSGVHTFPAVLQSSGLYSLSSVVTVPSSSLGTQ
8.11G    GGTAALGCLVKDYFPEPVTVSWNSGALTSGVHTFPAVLQSSGLYSLSSVVTVPSSSLGTQ
25.10C   GGTAALGCLVKDYFPEPVTVSWNSGALTSGVHTFPAVLQSSGLYSLSSVVTVPSSSLGTQ
         *******

10.4B    ------------------------------------------------------------
19.7E    TYICNVNHKPSNTKVDKKVEPQSCDKTHTCPPCPAPELL---------------------
2.9D     TYICNVNHKPSNTKVDKRVEPKSCDKTHTCPPCPAPELLGGPSVFLFPPKPKDTLMISRT
25.6A    ------------------------------------------------------------
36.1F    TYICNVNHKPSNTKVDKRVEPKSCDKTHTCPPCPAPELLGGPSVFLFPPX----------
36.9F    TYICNVNHKPSNTKVDKRVEPKSCDKTHTCPPCPAPELLGGPSVFLFPPNPRTPS*S---
37.2D    TYICNVNHKPSNTKVDKRVEPKSCDKTHTCPPCPAPELLGGPSVFLF-------------
37.2G    TYICNVNHKPSNTKVDKRVEPKSCDKTHTCPPCPAPELLGGPSVFLFPPKPKDTLMISRT
37.7H    TYICNVNHKPSNTKVDKRVEPKSCDKTHTCPPCPAPELLGGPSVFLFPPKPKDTLMISRT
8.9F     TYICNVNHKPSNTKVDKRVEPKSCDKTHTCPPCPAPELLGGPSVFLFPPKPKDTLMX---
NE13     TYICNVNHKPSNTKVDKRVEPKSCDKTHTCPPCPAPELLGGPSVFLFPPKPKDTLMISRT
12.1F    TYICNVNHKPSNTKVDKRVEPKSCDKTHTCPPCPAPELLGGPSVFLXPPKPKDTLMISRT
9.8A     TYICNVNHKPSNTKVDKRVEPKSCDKTHTCPPCPAPELLGGPSVFLFPPKPRTPS*SPGP
18.5C    TYICNVNHKPSNTKVDKRVEPKSCDKTHTCPPCPAPELLGGPSVFLFPPKPKDTLMISRT
8.11G    TYICNVNHKPSNTKVDKRVEPKSCDKTHTCPPCPAPELLGGPSVFLFPPKPKDTLMIFRT
25.10C   TYICNVNHKPSNTKVDKRVEPKSCDKTHTCPPCPAPELLGGPSVFLFPPNPRTPS-----

10.4B    -------------------------
19.7E    -------------------------
2.9D     PEVTCVVVDVS--------------
25.6A    -------------------------
36.1F    -------------------------
36.9F    -------------------------
37.2D    -------------------------
37.2G    PEVTCVVVDVSHEDPEVKFNWYVDGV
37.7H    PEVTCVVVDVSHE------------
8.9F     -------------------------
NE13     P------------------------
12.1F    PEVTCVVVDVS--------------
9.8A     -------------------------
18.5C    PEVTC--------------------
8.11G    PEVTCVVVDVS--------------
25.10C   -------------------------
```

FIG. 7 Cont.

```
                                                               CDR1: +++++++++++
10.4B      METDTLLLWVLLLWVPGSTGDEIVLTQSPSSLSASVGDRVTITCRASRDI------NTYL
19.7E      METDTLLLWLLLLWVPGSTGDEIVLTQSPSTLSASVGDRVTITCRASQSI------NNWL
2.9D       MKTDTLLLWVLLLWVPGSTGDDIVLTQSPDSLAVSLGERATINCKSSQSVLYSSNNKNYL
25.6A      METDTLLLWVLLLWVPGSTGDLPVLTQ-PASVSGSPGQSITISCTGTSSDV---GAYNYV
36.1F      METDTLLLWVLLLWVPGSTGDEIVLTQSPGTLSLSPGERATLSCRASQSVT------KNYL
36.9F      METDTLLLWVLLLWVPGSTGDDIVMTQSPDSLAVSLGERATINCKSSQTVLFTS---YYV
37.2D      METDTLLLWVLLLWVPGSTGDETTLTQSPATLSVSPGETATLSCRASQNVI------N-NL
37.2G      METDTLLLWVLLLWVPGSTGDDIVLTQSPGTLSLSPGERATLSCRASQSVN------SIFL
37.7H      METDTLLLWVLLLWVPGSTGDQSALTQ-PASVSGSPGQSITISCTGTGSDI---GGYNFV
8.9F       METDTLLLWVLLLWVPGSTGDQAGLTQ-PASVSGSPGQSITISCTAANSDI---GDFNFV
NE13       METDTLLLWVLLLWVPGSTGDETTLTQSPGTLSLSPGERATLSCRASQSVS------STYL
12.1F      METDTLLLWVLLLWVPGSTGDETTLTQSPATLSLSPGERATLSCRASQSVS------S-YL
9.8A       METDTLLLWVLLLWVPGSTGDDIVMTQSPSTLSASVGDRVTITCRASQSI------DRWL
18.5C      METDTLLLWVLLLWVPGSTGDDIQMTQSPGTLSLSPGERATLSCRASQSVI------SYYV
8.11G      METDTLLLWVLLLWVPGSTGDEIVLTQSPATLSVSPGGRASLSCRASQSIG-------DKL
25.10C     METDTLLLWVLLLWVPGSTGDDIQMTQSPSSLSASVGDRVIITCRASQSI------SSSL
           *:*******:***********      :** * ::: * *     :.* .:          :

CDR2: ^^^                              CDR3: #####
10.4B      GWFQQRPGKAPKSLIYGASNLQNGVPSRFSGSGSGTYFTLTINGLQTEDFATYYCQQYSI
19.7E      AWYQEKPGKAPKLLINKASSLESGVPSRFSGSGSGTEFTLTITSLQPDDFATYYCQQYNS
2.9D       AWYQQKPGQPPKLLIYWASTRESGVPDRFSGSGSGTDFTLTISSLQAEDVAVYYCQQYYS
25.6A      SWYQQHPGKAPKLIIYEVKIRPSGVSNRFSGSKSGNTASLTISGLQAEDEADYFCSSYST
36.1F      AWYQQKPGQAPTLVIYDASTRASGIPDRFIGSGSGTDFTLTISRLEPEDFAVYYCHQYGS
36.9F      AWYQQKPGQPPKLLFSGASSRESGVPDRFSAGGSGTDFYLTINSLQAEDVADYYCQQYHT
37.2D      AWYQQKPGQAPRLLIYGASTRATGIPARFSGSGSGTEFTLTISSMQSEDFAVYYCQQYND
37.2G      AWYQQKPGQAPRLLIYGASSRATGIPDRFSGSGSGTDFTLTISRLEPEDFAVYYCQQYHS
37.7H      SWYQQYPGKAPKLIIYEVRIRASGVSNRFSGSKSGNTASLTISGLQAEDEADYYCNSYSI
8.9F       SWYQQRPDKAPKLMVYEVSSRPSGVSNRFSGSKSGNTASLTISGLQAEDEADYYCTSYTS
NE13       AWYQQKPGQSPRLLIYGASSRATGIPDRFSGSGSGTQFTLTINRLEPEDFAVYYCQQFGS
12.1F      AWYQHKPGQAPRLLIYGASKRATGIPSRFSGSGSGTDFSLTISSLEPEDFAVYYCQHRSD
9.8A       AWYQQKPGKAPKLLIYQASSLERGVPSRFSGSGSGTEFTLTISSLQPDDFATYYCQQYNG
18.5C      AWYQHKGGQAPRLLIYGASSRATGVPDRFSGSGSGTDFTLTISSLEPEDFALYYCQYYGS
8.11G      SWYQQKPGQAPRLVIYGAYTRATDISPRFSGSRSGTDFNLTISRMQSGDFAVYFCQQYEN
25.10C     NWYQQKPGKAPKLLIYAAVNLETGVPSRFSGSFGTDFTLAISNVQPEDFATYYCQQSDT
           *:*.  .: *  :.    .:  ** ..  *. *:*. ::  * * *:*

CDR3: #####
10.4B      Y-PLSLGGGTKADMKR-TVAAPSVFIFPPSDEQLKSGTASVVCLLNNFYPREAKVQWKVD
19.7E      N-SWTFGQGTKVDMKR-TVAAPSVFIFPPSDEQLKSGTASVVCLLNNFYPREAKVQWKVD
2.9D       T-PPTFGQGTKVEIKR-TVAAPSVFIFPPSDEQLKSGTASVVCLLNNFYPREAKVQWKVD
25.6A      NSPWVFGGGTKVTVLRQPKAAPSVTLFPPSSEELQANKATLVCLISDFYPGAVTVAWKAD
36.1F      SPPYTFGRGTKLEIKR-TVAAPSVFIFPPSDEQLKSGTASVVCLLNNFYPREAKVQWKVD
36.9F      P-PFTFGGGTKLEIRR-TVAAPSVFIFPPSDEQLKSGTASVVCLLNNFYPREAKVQWKVD
37.2D      W-PRSFGQGTRLDIRR-TVAAPSVFIFPPSDEQLKSGTASVVCLLNNFYPREAKVQWKVD
37.2G      SPKLTFGGGTKVEIKR-TVAAPSVFIFPPSGEQLKSGTASVVCLLNNFYPREAKVQWKVD
37.7H      HSPWVFGGGTKLTVLRQPKAAPSVTLFPPSSEELQANKATLVCLISDFYPGAVTVAWKAD
8.9F       SSTFVFGTGTKVTVLGQPKANPTVTLFPPSSEELQANKATLVCLISDFYPGAVTVAWKAD
NE13       --PWTFGQGTKVEIKR-TVAAPSVFIFPPSDEQLKSGTASVVCLLNNFYPREAKVQWKVD
12.1F      W-RTTFGQGTRLEIKR-TVAAPSVFIFPPSDEQLKSGTASVVCLLNNFYPREAKVQWKVD
9.8A       Y-PLTFGGGTKVEIKR-TVAAPSVFIFPPSDEQLKSGTASVVCLLNNFYPREAKVQWKVD
18.5C      SPLWAFGQGTKVEIKR-TVAAPSVFIFPPSDEQLKSGTASVVCLLNNFYPREAKVQWKVD
8.11G      W-PRTFGQGTKLEIKR-TVAAPSVFIFPPSDEQLKSGTASVVCLLNNFYPREAKVQWKVD
25.10C     ---RTFGRGTKLDVKR-TVAAPSVFIFPPSDEQLKSGTASVVCLLNNFYPREAKVQWKVD
           :* **:  :      * :.* :****.*:*:::.:***:..*** ..**.**.*
```

FIG. 8

```
10.4B    NALQSGNSQESVTEQDSKDSTYSLSSTLTLSKADYEKHKVYACEVTHQGLSSP-------
19.7E    NALQSGNSQESVTEQDSKDSTYSLSSTLTLSKADYEKHKVYACEVTHQGLSSPVTKSFNR
2.9D     NALQSGNSQESVTEQDSKDSTYSLSSTLTLSKADYEKHKVYACEVTHQGLSSPVTKSFNR
25.6A    SSPVKAGV-ETTTPSKQSNNKYAASSYLSLTPEQWKSHRSYSCQVTHEGST--VEKTVAP
36.1F    NALQSGNSQESVTEQDSKDSTYSLSSTLTLSKADYEKHKVYACEVTHQGLSSPVTKSFNR
36.9F    NALQSGNSQESVTEQDSKDSTYSLSSTLTLSKADYEKHKVYACEVTHQGLSSPVTKSFNR
37.2D    NALQSGNSQESVTEQDSKDSTYSLSSTLTLSKADYEKHKVYACEVTHQGLSSPVTKSFNR
37.2G    NALQSGNSQESVTEQDSKDSTYSLSSTLTLSKADYEKHKVYACEVTHQGLSSPVTKSFNR
37.7H    SSPVKAGV-ETTTPSKQSNNKYAASSYLSLTPEQWESHRSYSCQVTHEGST--VEKTVAP
8.9F     SSPVKAGV-ETTTPSKQSNNKYAASSYLSLTPEQWKSHRSYSCQVTHEGST--VEKTVAP
NE13     NALQSGNSQESVTEQDSKDSTYSLSSTLTLSKADYEKHKVYACEVTHQGLSSPVTKSFNR
12.1F    NALQSGNSQESVTEQDSKDSTYSLSSTLTLSKADYEKHKVYACEVTHQGLSSPVTKSFNR
9.8A     NALQSGNSQESVTEQDSKDSTYSLSSTLTLSKADYEKHKVYACEVTHQGLSSPVTKSFNR
18.5C    NALQSGNSQESVTEQDSKDSTYSLSSTLTLSKADYEKHKVYACEVTHQGLSSPVTKSFNR
8.11G    NALQSGNSQESVTEQDSKDSTYSLSSTLTLSKADYEKHKVYACEVTHQGLSSPVTKSFNR
25.10C   NALQSGNSQESVTEQDSKDSTYSLSSTLTLSKADYEKHKVYACEVTHQGLSSPVTKSFNR
          .:   ...    *:.*  ....:..*: ** *:*:   :::.*: *:*:***:* :

10.4B    ------------------------------------------------------------
19.7E    GEC---------------------------------------------------------
2.9D     GEC---------------------------------------------------------
25.6A    TECS*-------------------------------------------------------
36.1F    GEC*--------------------------------------------------------
36.9F    GEC*--------------------------------------------------------
37.2D    GEC*--------------------------------------------------------
37.2G    GEC*--------------------------------------------------------
37.7H    TECS*-------------------------------------------------------
8.9F     TECS*-------------------------------------------------------
NE13     GEC*--------------------------------------------------------
12.1F    GEC*--------------------------------------------------------
9.8A     GEC*--------------------------------------------------------
18.5C    GEC*--------------------------------------------------------
8.11G    GEC*--------------------------------------------------------
25.10C   GEVLGGRKLGRHGPTCLLQLIMVTNKAIASQISQIKHFFHCILVVVCPNSSMYLIMSGSG
```

FIG. 8 Cont.

SEQUENCE LISTING

<160> NUMBER OF SEQ ID NOS: 144

<210> SEQ ID NO 1
<211> LENGTH: 670
<212> TYPE: DNA
<213> ORGANISM: Artificial Sequence
<220> FEATURE:
<223> OTHER INFORMATION: cDNA 10.4B HC variable region
<221> NAME/KEY: misc_feature
<222> LOCATION: 11
<223> OTHER INFORMATION: n = A,T,C or G

<400> SEQUENCE: 1

| | | | | | | |
|---|---|---|---|---|---|---|
| tgcgcgttac | ngatccaagc | tgtgaccggc | gcctacctga | tcaccggt | gctagcacca | 60 |
| tggagacaga | cacactcctg | ctatgggtac | tgctgctctg | ggttccaggt | tccactggtg | 120 |
| accaggtgca | gctggtacag | tctgggggag | gcgtggtcca | gcctgggagg | tccctgagag | 180 |
| tctcctgtgt | tacgtctgga | ttcaatttca | gagcctacgg | catgcactgg | gtccgccaga | 240 |
| ttccaggcaa | gggactggag | tgggtggcag | atatttggtc | tgccgagact | aatagacact | 300 |
| atgcagattc | cgtgaagggc | cgattcacca | tctccagaga | caactccaag | agcacactgt | 360 |
| atctgcaaat | gaacagcctg | agagccgagg | acacggcgt | atatttctgt | gccaaagcgc | 420 |
| gaccaggcta | tgattatgtc | gttgacttat | ggggccaggg | aacgctggtc | atcgtctcct | 480 |
| cagcttccac | caagggccca | tcggtcttcc | ccctggcgcc | ctgctccagg | agcacctctg | 540 |
| ggggcacagc | ggccctgggc | tgcctggtca | aggactactt | ccccgaaccg | gtgacggtgt | 600 |
| cgtggaactc | aggcgccctg | accagcggcg | tgcacacctt | cccggctgtc | ctacagtcct | 660 |
| caggactcta | | | | | | 670 |

<210> SEQ ID NO 2
<211> LENGTH: 819
<212> TYPE: DNA
<213> ORGANISM: Artificial Sequence
<220> FEATURE:
<223> OTHER INFORMATION: cDNA 19.7E HC variable region

<400> SEQUENCE: 2

| | | | | | | |
|---|---|---|---|---|---|---|
| atccagctgt | gaccggcgcc | tacctgagat | caccggtgct | agcaccatgg | agacagacac | 60 |
| actcctgcta | tgggtactgc | tgctctgggt | tccaggttcc | actggtgacg | aggtgcagct | 120 |
| ggtggagtct | gggggaggct | tagttcggcc | tggggggtcc | ctgagactct | cctgtgcagc | 180 |
| ctctggattc | tccttcagta | gctactcgat | gcactgggtc | cgccatgttc | tgggaaggg | 240 |
| gctggtgtgg | gtctcatata | ttaatagtga | tgggagtact | aaaatctacg | cggactccgt | 300 |
| gaagggccga | ttctccatct | ccagagacaa | tgccaagaac | aagctctatc | tgcaaatgga | 360 |
| cagtttgaga | gtcgaggaca | cggctgtata | ttcgtgtgta | aggcttgtac | attacgactg | 420 |
| gtccccattc | gtgtgggcc | agggaaccct | ggtcaccgtc | tcctcagcct | ccaccaaggg | 480 |
| cccatcggtc | ttccccctgg | caccctcctc | caagagcacc | tctgggggca | gcggccct | 540 |
| gggctgcctg | gtcaaggact | acttccccga | accggtgacg | gtgtcgtgga | actcaggcgc | 600 |
| cctgaccagc | ggcgtgcaca | ccttcccggc | tgtcctacag | tcctcaggac | tctactccct | 660 |
| cagcagcgtg | gtgaccgtgc | cctccagcag | cttgggcacc | cagacctaca | tctgcaacgt | 720 |
| gaatcacaag | cccagcaaca | ccaaggtgga | caagaaagtt | gagcccaat | cttgtgacaa | 780 |
| aactcacaca | tgcccaccgt | gcccagcacc | tgaactcct | | | 819 |

<210> SEQ ID NO 3

```
<211> LENGTH: 920
<212> TYPE: DNA
<213> ORGANISM: Artificial Sequence
<220> FEATURE:
<223> OTHER INFORMATION: cDNA 2.9D HC variable region

<400> SEQUENCE: 3
gtcactgcac ctcggttcta tcgattggct agcaccatgg agacagacac actcctgcta      60
tgggtactgc tgctctgggt tccaggttcc actggtgacg aggtgcagct ggtggagtct     120
gggggaggcc tggtcaagcc tggggggtcc cttagactct cctgtgcagc ctctggattc     180
accttcacta gatttacttt gacctgggtc cgccaggctc cagggaaggg gctggagtgg     240
gtctcatcca ttagtagtgg gagtagtgac ataaactacg cagactcagt gaagggccga     300
ttcaccatat ccagagacaa cgccaggaac tccctgttcc tgcaaatgag cagcctgaga     360
gtcgacgaca cggctgtgta ttactgtgcg aaagatcccc ggtcggggat ctctggtcgc     420
tacgggatgg acgtctgggg ccaagggacc acggtcatcg tctcctcagc ttccaccaag     480
ggcccatcgg tcttcccccct ggcgccctgc tccaggagca cctctggggg cacagcggcc     540
ctgggctgcc tggtcaagga ctacttcccc gaaccggtga cggtgtcgtg gaactcaggc     600
gccctgacca gcggcgtgca caccttcccg gctgtcctac agtcctcagg actctactcc     660
ctcagcagcg tggtgaccgt gccctccagc agcttgggca cccagaccta catctgcaac     720
gtgaatcaca agcccagcaa caccaaggtg gacaagagag ttgagcccaa atcttgtgac     780
aaaactcaca catgcccacc gtgcccagca cctgaactcc tggggggacc gtcagtcttc     840
ctcttccccc caaaacccaa ggacaccctc atgatctccc ggacccctga ggtcacatgc     900
gtggtggtgg acgtgagcca                                                 920

<210> SEQ ID NO 4
<211> LENGTH: 540
<212> TYPE: DNA
<213> ORGANISM: Artificial Sequence
<220> FEATURE:
<223> OTHER INFORMATION: cDNA 25.6A HC variable region

<400> SEQUENCE: 4
acctcggttc ttcgattggc tagcaccatg gagacagaca cactcctgct atgggtactg      60
ctgctctggg ttccaggttc cactggtgac caggtgcagc tgcaggagtc aggaggaggc     120
ctggtcaagg ctgggggggtc cctgagactc tcctgtgcag cctctggatt catgttcgag     180
agatatagcc ttcactgggt ccgtcagact ccaggcaagg ggctggagtg gtctcatcc     240
attagtagtc ttagtggcag tcacataaac tacgcagact cagtgaaggg ccgattcacc     300
atctccagag acaacgccaa gaattcactg tctctgcaaa tgaacagcct gagagtcgaa     360
gacacggcta tatattattg tgcgagagat cgacgttcgg ggagttcccc cgtccccttg     420
gacgtctggg gccaagggac cacggtcacc gtctcctctg cctccaccaa gggcccatcg     480
gtcttccccc tggcaccctc ctccaagagc acctctgggg gcacagcggc cctgggctgc     540

<210> SEQ ID NO 5
<211> LENGTH: 855
<212> TYPE: DNA
<213> ORGANISM: Artificial Sequence
<220> FEATURE:
<223> OTHER INFORMATION: cDNA 36.1F HC variable region

<400> SEQUENCE: 5
gtcactgccc tcggttctat cgattggcta gcaccatgga gacagacaca ctcctgctat      60
```

```
gggtactgct gctctgggtt ccaggttcca ctggtgacca ggtgcagctg caggagtcgg    120
gcgcgggact ggtgaagcct tcggagaccc tgtccctcac ctgcgctgtc tcaggtggac    180
ccttcagcgg tgcctactgg acgtggatcc gccaaactcc agggaagggg ctggagtgga    240
ttggagaggc cggtcggagt ggaaccacca actacaatcc gtccctcaag agtcgagtca    300
ccatatcact ggacacgtcc aagagccagt tttccctgaa gctgacttcc gtgaccgccg    360
cggacacggc tgtttacttc tgtgggagac gccaaataat gtctttgagt aatctttata    420
agagacccgt tgactcttgg ggccggggaa ccccggtcat cgtctcctca gcctccacca    480
agggcccatc ggtcttcccc ctggcaccct cctccaagag cacctctggg ggcacagcgg    540
ccctgggctg cctggtcaag gactacttcc ccgaaccggt gacggtgtcg tggaactcag    600
gcgccctgac cagcggcgtg cacaccttcc cggctgtcct acagtcctca ggactctact    660
ccctcagcag cgtggtgacc gtgccctcca gcagcttggg cacccagacc tacatctgca    720
acgtgaatca caagcccagc aacaccaagg tggacaagag agttgagccc aaatcttgtg    780
acaaaactca cacatgccca ccgtgcccag cacctgaact cctggggga ccgtcagtct    840 tcctcttccc cccaa                                                     855
```

<210> SEQ ID NO 6
<211> LENGTH: 874
<212> TYPE: DNA
<213> ORGANISM: Artificial Sequence
<220> FEATURE:
<223> OTHER INFORMATION: cDNA 36.9F HC variable region

<400> SEQUENCE: 6

```
gtcactgccc tcggttctat cgattggcta gcaccatgga gacagacaca ctcctgctat     60
gggtactgct gctctgggtt ccaggttcca ctggtgacga ggtgcagctg gtgcagtctg    120
gaggaggcct ggtcaaggcg ggggggtccc tgaaactctc ctgtggagcc tctggattca    180
ccttcagtag ttatagcatg agctgggtcc gccaggctcc agggaagggg ctggagtggg    240
tctcatacat tagtagtggt gggagttcta tacactacgc agactcagtg aagggccgat    300
tcaccatctc cagagacaac gccaagaatt cactgtatct gcaaatgaag aacctgaggg    360
ctgacgacac gggtcggtat tattgtgtga gagatccccg atcggggatc tctggtcggt    420
acggtatgga cgtctggggt caagggacca cggtcaccgt ctcctcagcc tccaccaagg    480
gcccatcggt cttccccctg gcaccctcct ccaagagcac ctctggggc acagcggccc    540 tgggctgcct ggtcaaggac tacttccccg aaccggtgac ggtgtcgtgg aactcaggcg    600
ccctgaccag cggcgtgcac accttcccgg ctgtcctaca gtcctcagga ctctactccc    660
tcagcagcgt ggtgaccgtg ccctccagca gcttgggcac ccagacctac atctgcaacg    720
tgaatcacaa gcccagcaac accaaggtgg acaagagagt tgagcccaaa tcttgtgaca    780
aaactcacac atgcccaccg tgcccagcac ctgaactcct gggggaccg tcagtcttcc    840 tcttcccccc aaacccaagg acaccctcat gatc                                 874
```

<210> SEQ ID NO 7
<211> LENGTH: 859
<212> TYPE: DNA
<213> ORGANISM: Artificial Sequence
<220> FEATURE:
<223> OTHER INFORMATION: cDNA 37.2D HC variable region

<400> SEQUENCE: 7

```
tcactgccct cggttctatc gattggctag caccatggag acagacacac tcctgctatg    60
ggtactgctg ctctgggttc caggttccac tggtgacgaa gtgcagctgg tgcagtctgg   120
agctgaggtg aagaagcctg ggcttcagt gaaggtgtcc tgcaaggcct ctggttacac   180
ctttacgaaa tacggaatca gctgggtgcg acaggcccct ggacaagggc ttgagtggat   240
gggatggatc agcgcgttta atggttacac aaggtatggt cagagattcc agggcaaagt   300
caccatgacc acagacacat ccacgaacac agcctctttg gaggtgagga ccctgacatc   360
taacgacacg gccgtctatt actgtgcgag acaatatccc gaccaatata gtagcagcgg   420
ttggccccgc ctcttcgcca tggacgtctg gggccaaggg accacggtca tcgtctcccc   480
agcctccacc aagggcccat cggtcttccc cctggcaccc tcctccaaga gcacctctgg   540
gggcacagcg gccctgggct gcctggtcaa ggactacttc cccgaaccgg tgacggtgtc   600
gtggaactca ggcgccctga ccagcggcgt gcacaccttc ccggctgtcc tacagtcctc   660
aggactctac tccctcagca gcgtggtgac cgtgccctcc agcagcttgg gcacccagac   720
ctacatctgc aacgtgaatc acaagcccag caacaccaag gtggacaaga gagttgagcc   780
caaatcttgt gacaaaactc acacatgccc accgtgccca gcacctgaac tcctgggggg   840
accgtcagtc ttcctcttc                                                859

<210> SEQ ID NO 8
<211> LENGTH: 960
<212> TYPE: DNA
<213> ORGANISM: Artificial Sequence
<220> FEATURE:
<223> OTHER INFORMATION: cDNA 37.2G HC variable region

<400> SEQUENCE: 8
tcactgccct cggttctatc gattggctag caccatggag acagacacac tcctgctatg    60
ggtactgctg ctctgggttc caggttccac tggtgacgag gtgcagctgg tggagtctgg   120
gggaggcctg gtcaagccgg gggggtcccg gagactctcc tgtgctgcct ctggattcac   180
cttcagtaga gataccatga cctgggtccg ccaggctcca gggaagggc tggagtgggt   240 cgcatccata gtagtggta gcagtgacat aaactacgca gactcagtga agggccgatt   300
caccatctcc agagacaacg caagaactc actgtatctg cacatgaaca gcctgagagc   360
cgacgacacg gctatatatt actgtgcgag agatccccgg tcgggaatct ctggtcggta   420
tggtatggac gtctggggcc aagggaccac ggtcaccgtc tcctcagcct ccaccaaggg   480
cccatcggtc ttccccctgg caccctcctc aagagcacc tctggggca cagcggccct   540 gggctgcctg gtcaaggact acttccccga accggtgacg gtgtcgtgga actcaggcgc   600
cctgaccagc ggcgtgcaca ccttcccggc tgtcctacag tcctcaggac tctactccct   660
cagcagcgtg gtgaccgtgc cctccagcag cttgggcacc cagacctaca tctgcaacgt   720
gaatcacaag cccagcaaca ccaaggtgga caagagagtt gagcccaaat cttgtgacaa   780
aactcacaca tgcccaccgt gcccagcacc tgaactcctg ggggaccgt cagtcttcct   840 cttccccca aaacccaagg acaccctcat gatctcccgg acccctgagg tcacatgcgt   900
ggtggtggac gtgagccacg aagaccctga ggtcaagttc aactggtacg tggacggcgt   960

<210> SEQ ID NO 9
<211> LENGTH: 924
<212> TYPE: DNA
<213> ORGANISM: Artificial Sequence
<220> FEATURE:
<223> OTHER INFORMATION: cDNA 37.7H HC variable region
```

<400> SEQUENCE: 9

```
gtcactgcac ctcggttcta tcgattggct agcaccatgg agacagacac actcctgcta    60
tgggtactgc tgctctgggt tccaggttcc actggtgacg aggtgcagct ggtgcagtct   120
ggaggaggcc tggtcaaggc ggggggtcc ctgaggctct cctgtgcagc ctccggattc   180
acattcagca cctacagtat gaactggatc cgccaggctc cagggaaggg gctggagtgg   240
gtcgcttcca ttagtagtcg aagtggcagt acataaaact acgtagactc agtgaaggga   300
cgattcacca tctccagaga caacgccagg gacttattgt atctgcaaat gaacagcctg   360
agagtcgacg actcggctct ctattactgt gcgagagatc gccgttcggg gacttctccc   420
ctccccttgg acgtctgggg ccaagggacc acggtcaccg tcttctcagc ctccaccaag   480
ggcccatcgg tcttccccct ggcacccctcc tccaagagca cctctggggg cacagcggcc   540
ctgggctgcc tggtcaagga ctacttcccc gaaccggtga cggtgtcgtg aactcaggc   600
gccctgacca gcggcgtgca caccttcccg gctgtcctac agtcctcagg actctactcc   660
ctcagcagcg tggtgaccgt gccctccagc agcttgggca cccagaccta catctgcaac   720
gtgaatcaca agcccagcaa caccaaggtg gacaagagag ttgagcccaa atcttgtgac   780
aaaactcaca catgcccacc gtgcccagca cctgaactcc tgggggggacc gtcagtcttc   840
ctcttccccc caaaacccaa ggacaccctc atgatctccc ggaccctga ggtcacatgc   900
gtggtggtgg acgtgagcca cgaa                                         924
```

<210> SEQ ID NO 10
<211> LENGTH: 911
<212> TYPE: DNA
<213> ORGANISM: Artificial Sequence
<220> FEATURE:
<223> OTHER INFORMATION: cDNA 8.9F HC variable region

<400> SEQUENCE: 10

```
cctcggttct atcgattggc tagcaccatg gagacagaca cactcctgct atgggtactg    60
ctgctctggg ttccaggttc cactggtgac cagggcacct tgagggagtc tggtccagga   120
ctggtgaggc cttcggagac cctgtccctc acctgcggtg tctctggtta ttccatcagt   180
agtggttact actggggctg gatccggcag cccccaggga aggggctgga gtggattggg   240
aatatctatc gtagtgggag cacctactac aacccgtccc tcaagagtcg agtcaccgtc   300
tcaatagaca cgtccaaaaa ccagttctcc ctgaagttga attctgtgac cgccgcagac   360
acggccgtgt attactgtgc gagatcgggt ataaaagtgg ctgacgacta ttactacgaa   420
atggacgtct ggggccaagg gaccgacgac tactcttacg ctatggacgt ctggggccaa   480
gggaccacgg tcaccgtctc ctcagcctcc accaagggcc catcggtctt ccccctggca   540
ccctcctcca agagcacctc tggggggcaca gcggccctgg gctgcctggt caaggactac   600
ttccccgaac cggtgacggt gtcgtggaac tcaggcgccc tgaccagcgg cgtgcacacc   660
ttcccggctg tcctacagtc ctcaggactc tactccctca gcagcgtggt gaccgtgccc   720
tccagcagct gggcacccca gacctacatc tgcaacgtga atcacaagcc cagcaacacc   780
aaggtggaca agagagttga gcccaaatct tgtgacaaaa ctcacacatg cccaccgtgc   840
ccagcacctg aactcctggg gggaccgtca gtcttcctct tccccccaaa acccaaggac   900
accctcatga t                                                       911
```

<210> SEQ ID NO 11

```
<211> LENGTH: 881
<212> TYPE: DNA
<213> ORGANISM: Artificial Sequence
<220> FEATURE:
<223> OTHER INFORMATION: cDNA NE13 HC variable region

<400> SEQUENCE: 11
actgcacctc ggttctatcg attggctagc accatggaga cagacacact cctgctatgg      60
gtactgctgc tctgggttcc aggttccact ggtgacgagg ttcagctggt ggagtctggg     120
ggaggcctgg tcaagcctgg ggggtccctg agactctcct gtgtagcctc tggattcacc     180
ttcagttcct atagcatgaa ctgggtccgc caggctccag gaaggggct ggagtgggtc      240
tcatccatta gtagtggtag tagttacata gagtacgcag actcagtgaa gggccgactc     300
accatctcca gagacaacgc caagaagtca ctgtatctgc aactgaacag cctgagagcc     360
gaggacacgg ctgtgtatta ctgtgcgaga cacacagctc gaatcgactc ttaccacggt     420
atggacgtct ggggccaagg gaccacagtc accgtctcct cagcctccac caagggccca     480
tcggtcttcc ccctggcacc ctcctccaag agcacctctg gggcacagc ggccctgggc      540
tgcctggtca aggactactt ccccgaaccg gtgacggtgt cgtggaactc aggcgccctg     600
accagcggcg tgcacacctt cccggctgtc ctacagtcct caggactcta ctccctcagc     660
agcgtggtga ccgtgccctc agcagcttg gcacccaga cctacatctg caacgtgaat      720
cacaagccca gcaacaccaa ggtggacaag agagttgagc ccaaatcttg tgacaaaact     780
cacacatgcc caccgtgccc agcacctgaa ctcctggggg gaccgtcagt cttcctcttc     840
cccccaaaac ccaaggacac cctcatgatc tcccggaccc c                        881

<210> SEQ ID NO 12
<211> LENGTH: 921
<212> TYPE: DNA
<213> ORGANISM: Artificial Sequence
<220> FEATURE:
<223> OTHER INFORMATION: cDNA 12.1F HC variable region
<221> NAME/KEY: misc_feature
<222> LOCATION: 849
<223> OTHER INFORMATION: n = A,T,C or G

<400> SEQUENCE: 12
gtcactgcac ctcggttcta tcgattggct agcaccatgg agacagacac actcctgcta      60
tgggtactgc tgctctgggt tccaggttcc actggtgacc aggtgcagct gcaggagtcg     120
ggcgcaggac tgttgaagcc ttcggagacc ctgtccctca gttgcactgt cgatggtgag     180
tccttcaatg gttccttctg gacgtggatc cgccagcccc cagggaaggg tctggagtgg     240
attggagaaa tcaatcatct gcaagcaccg gctacaaccc gtccctcaa gagtcgagtc      300
accatttcag tagacacgtc caagaaccag ttctctttga gttgacctc tgtgaccgcc      360
gcggacacgg ctgtgtatta ctgtgcgaga ggatacagct atggttttgc atggcccaac     420
taccactatt tggacgtctg gggcaaaggg accacggtca ccgtctcctc agcctccacc     480
aagggcccat cggtcttccc cctggcaccc tcctccaaga gcacctctgg gggcacagcg     540
gccctgggct gcctggtcaa ggactacttc cccgaaccgg tgacggtgtc gtggaactca     600
ggcgccctga ccagcggcgt gcacaccttc ccggctgtcc tacagtcctc aggactctac     660
tccctcagca gcgtggtgac cgtgccctcc agcagcttgg cacccagac ctacatctgc      720
aacgtgaatc acaagcccag caacaccaag gtggacaaga gagttgagcc caaatcttgt     780
gacaaaactc acacatgccc accgtgccca gcacctgaac tcctgggggg accgtcagtc     840
```

```
ttcctcttnc ccccaaaacc caaggacacc ctcatgatct cccggacccc tgaggtcaca      900
tgcgtggtgg tggacgtgag c                                                921

<210> SEQ ID NO 13
<211> LENGTH: 874
<212> TYPE: DNA
<213> ORGANISM: Artificial Sequence
<220> FEATURE:
<223> OTHER INFORMATION: cDNA 9.8A HC variable region

<400> SEQUENCE: 13
ttctatcgat ttggctagca ccatggagac agacacactc ctgctatggg tactgctgct       60
ctgggttcca ggttccactg gtgacgaggt gcagctggtg cagtctggag acgcttggt       120 acagcctggg gggtccctga cactctcctg tgtagcctct ggattcacct ttagcagcca      180
tgccatgagc tgggtccgcc aggctccagg aaggggctg gagtgggtct caggttttag       240
tggtagtagt ggtaccacaa agtacgcaga ctccgtgaag gccggttca ccatctccag       300 agacaattcc aagaaaacgc tgtatctgca aatgaacagc ctgagagccg aggacacggc      360
cgtatattac tgtgcgaaag gcttctcccc atttcgggga gtacaattcc cctactttga     420
ctactggggc cagggaacgc tggtcaccgt ctcctcagcc tccaccaagg gcccatcggt      480 cttcccctg gcaccctcct ccaagagcac ctctgggggc acagcggccc tgggctgcct      540
ggtcaaggac tacttccccg aaccggtgac ggtgtcgtgg aactcaggcg ccctgaccag     600
cggcgtgcac accttcccgg ctgtcctaca gtcctcagga ctctactccc tcagcagcgt     660
ggtgaccgtg ccctccagca gcttgggcac ccagacctac atctgcaacg tgaatcacaa     720
gcccagcaac accaaggtgg acaagagagt tgagcccaaa tcttgtgaca aaactcacac     780
atgcccaccg tgcccagcac ctgaactcct ggggggaccg tcagtcttcc tcttcccccc      840
aaaacccagg acaccctcat gatctcccgg accc                                  874

<210> SEQ ID NO 14
<211> LENGTH: 898
<212> TYPE: DNA
<213> ORGANISM: Artificial Sequence
<220> FEATURE:
<223> OTHER INFORMATION: cDNA 18.5C HC variable region

<400> SEQUENCE: 14
gtccactgca cctcggttct atcgattggc tagcaccatg gagacagaca cactcctgct       60
atgggtactg ctgctctggg ttccaggttc cactggtgac gaggttcagc tggtggagtc      120
tgggggaggc ctggtcaggc cggggggtc ccttagactc tcctgtgcag ccgctggatt       180
cactttcaag agttatagca tgaattgggt ccgccaggct ccaggagggg gcctggagtg      240
ggtctcatct atcactagtg gtggtagtaa gacatactat gcagacgtag tgaagggccg      300
attcaccgtc tccagagaca acgccaagca gtcgctctat ctgcaaatga acagcctgag      360
agccgaggac acggctatat acttctgtgc gagatcccta catagtacca gccagcctag      420
ctacatggac gtctgggca gaaagatcac ggtcatcgtc tcctcagcct ccaccaaggg      480
cccatcggtc ttccccctgg caccctcctc caagagcacc tctgggggca gcggccct     540 gggctgcctg gtcaaggact acttccccga accggtgacg gtgtcgtgga actcaggcgc      600
cctgaccagc ggcgtgcaca ccttcccggc tgtcctacag tcctcaggac tctactccct      660
cagcagcgtg gtgaccgtgc cctccagcag cttgggcacc cagacctaca tctgcaacgt      720
gaatcacaag cccagcaaca ccaaggtgga caagagagtt gagcccaaat cttgtgacaa      780
```

```
aactcacaca tgcccaccgt gcccagcacc tgaactcctg ggggaccgt cagtcttcct      840 cttcccccca aacccaagg acaccctcat gatctcccgg accctgagg tcacatgc        898

<210> SEQ ID NO 15
<211> LENGTH: 903
<212> TYPE: DNA
<213> ORGANISM: Artificial Sequence
<220> FEATURE:
<223> OTHER INFORMATION: cDNA 8.11G HC variable region

<400> SEQUENCE: 15
tgcacctcgg ttctatcgat tggctagcac catggagaca gacacactcc tgctatgggt     60
actgctgctc tgggttccag gttccactgg tgaccaggtg cagctgcagg agtcgggtcc    120
aggactggtg aagccttcgg agaccctgtc cctcacctgc agtatttctg gtgtgtccac    180
cagaaattat tattggagct ggatccgcca gtccccaggg aagggactgg agtggattgg    240
atatatcttt aacattggga ccaccaacta caatccgtcc ctcaagagtc gactcaccat    300
atctgtagac acgtcgaaga accagttctc cctgaagatc acctctgtga ccgctgcgga    360
cacggccgtc tattactgtg cgagtggatt tgagtacggt gactatacct tcgactactg    420
gggccaggga accccggtca ccgtctcctc agcctccacc aagggcccat cggtcttccc    480
cctggcaccc tcctccaaga gcacctctgg gggcacagcg gccctgggct gcctggtcaa    540
ggactacttc cccgaaccgg tgacggtgtc gtggaactca ggcgccctga ccagcggcgt    600
gcacaccttc ccggctgtcc tacagtcctc aggactctac tccctcagca gcgtggtgac    660
cgtgccctcc agcagcttgg gcacccagac ctacatctgc aacgtgaatc acaagcccag    720
caacaccaag gtggacaaga gagttgagcc caaatcttgt gacaaaactc acacatgccc    780
accgtgccca gcacctgaac tcctgggggg accgtcagtc ttcctcttcc cccaaaacc    840 caaggacacc ctcatgatct ccggaccccc tgaggtcaca tgcgtggtgg tggacgtgag    900
cca                                                                  903

<210> SEQ ID NO 16
<211> LENGTH: 860
<212> TYPE: DNA
<213> ORGANISM: Artificial Sequence
<220> FEATURE:
<223> OTHER INFORMATION: cDNA 25.10C HC variable region

<400> SEQUENCE: 16
ctcggttcta tcgattggct agcaccatgg agacagacac actcctgcta tgggtactgc     60
tgctctgggt tccaggttcc actggtgacc aggtgcagct gcaggagtct ggggaggcc    120 tggtcaagcc tgggggtcc ctgagactct cctgtacagc ctctggattc aacttcaata    180
aatataacat gaactgggtc cgccaggctc agggaaggg gctggagtgg gtctcatcca    240
ttagtgctct tagcacttac atctattatg cagactcgct gaaggccga ttcaccgtct    300 ccagagacaa cgccaagaac tcactgtttc tgcaaatgaa cagcctgaga gacgacgaca    360
cggctgttta ttactgtgcg agagaaatac gacgtgccag tacctggtcc gccgacctct    420
ggggccgtgg cactctggtc actgtctcct cagcctccac caagggccca tcggtcttcc    480
ccctggcacc ctcctccaag agcacctctg gggcacagc ggccctgggc tgcctggtca    540
aggactactt ccccgaaccg gtgacggtgt cgtggaactc aggcgccctg accagcggcg    600
tgcacacctt cccggctgtc ctacagtcct caggactcta ctccctcagc agcgtggtga    660
```

| | |
|---|---|
| ccgtgccctc cagcagcttg ggcacccaga cctacatctg caacgtgaat cacaagccca | 720 |
| gcaacaccaa ggtggacaag agagttgagc ccaaatcttg tgacaaaact cacacatgcc | 780 |
| caccgtgccc agcacctgaa ctcctggggg gaccgtcagt cttcctcttc cctccaaacc | 840 |
| caaggacacc ctcatgatct | 860 |

<210> SEQ ID NO 17
<211> LENGTH: 716
<212> TYPE: DNA
<213> ORGANISM: Artificial Sequence
<220> FEATURE:
<223> OTHER INFORMATION: cDNA 10.4B LC variable region

<400> SEQUENCE: 17

| | |
|---|---|
| agctgtgacc ggcgcctacc tgagatcacc ggtgctagca ccatggagac agacacactc | 60 |
| ctgctatggg tactgctgct ctgggttcca ggttccactg gtgacgaaat tgtgttgaca | 120 |
| cagtctccat cctcactgtc tgcgtctgta ggagacagag tcaccatcac ttgtcgggcg | 180 |
| agtcgggaca tcaatactta tttaggttgg tttcagcaga gaccagggaa agcccctaag | 240 |
| tccctgatct atggtgcatc taatttgcaa aatggggtcc catcaaggtt cagcggcagt | 300 |
| ggatctggga cgtattttac tctcaccatc aacggcctgc agactgaaga ctttgcgact | 360 |
| tattattgcc aacaatatag catctacccg ctcagtctcg gcggagggac caaggcggac | 420 |
| atgaagcgaa ctgtggctgc accatctgtc ttcatcttcc cgccatctga tgagcagttg | 480 |
| aaatctggaa ctgcctctgt tgtgtgcctg ctgaataact tctatcccag agaggccaaa | 540 |
| gtacagtgga aggtggataa cgccctccaa tcgggtaact cccaggagag tgtcacagag | 600 |
| caggacagca aggacagcac ctacagcctc agcagcaccc tgacgctgag caaagcagac | 660 |
| tacgagaaac acaaagtcta cgcctgcgaa gtcacccatc agggcctgag ctcgcc | 716 |

<210> SEQ ID NO 18
<211> LENGTH: 906
<212> TYPE: DNA
<213> ORGANISM: Artificial Sequence
<220> FEATURE:
<223> OTHER INFORMATION: cDNA 19.7E LC variable region

<400> SEQUENCE: 18

| | |
|---|---|
| tcagctgtga ccggcgccta cctgagatca ccggtgctag caccatggag acagacacac | 60 |
| tcctgctatg gctcctgctg ctctgggttc aggttccac tggtgacgaa attgtgttga | 120 |
| cacagtctcc ttccaccctg tctgcatctg tgggagacag agtcaccatc acttgccggg | 180 |
| ccagtcagag tattaataat tggttggcct ggtatcagga gaaccagggg aaagccccta | 240 |
| agctcctgat aaataaggcg tctagtttag aaagtggggt cccatcaagg ttcagcggca | 300 |
| gtggatctgg gacagaattc actctcacca tcaccagcct gcagcctgat gattttgcaa | 360 |
| cttattactg ccaacaatat aatagtaatt cgtggacgtt cggccaaggg accaaggtgg | 420 |
| acatgaaacg aactgtggct gcaccatctg tcttcatctt cccgccatct gatgagcagt | 480 |
| tgaaatctgg aactgcctct gttgtgtgcc tgctgaataa cttctatccc agagaggcca | 540 |
| aagtacagtg gaaggtggat aacgccctcc aatcgggtaa ctcccaggag agtgtcacag | 600 |
| agcaggacag caaggacagc acctacagcc tcagcagcac cctgacgctg agcaaagcag | 660 |
| actacgagaa acacaaagtc tacgcctgcg aagtcaccca tcagggcctg agctcgcccg | 720 |
| tcacaaagag cttcaacagg ggagagtgtt agagggagct agctcgacat gataagatac | 780 |
| attgatgagt ttggacaaca cacaactaga atgcagtgaa aaaaatgctt tatttgtgaa | 840 |

```
atttgtgatg ctattgcttt tattgtgaaa tttgtgatgc tattgcttta tttgtaacca    900
ttataa                                                                906
```

<210> SEQ ID NO 19
<211> LENGTH: 894
<212> TYPE: DNA
<213> ORGANISM: Artificial Sequence
<220> FEATURE:
<223> OTHER INFORMATION: cDNA 2.9D LC variable region

<400> SEQUENCE: 19

```
actgcacctc ggttctatcg attggctagc accatgaaga cagacacact cctgctatgg     60
gtactgctgc tctgggttcc aggttccact ggtgacgaca ttgtgctgac ccagtctcca    120
gactccctgg ctgtgtctct gggcgagagg gccaccatca actgcaagtc cagccagagt    180
gttttataca gctccaacaa taagaactac ttagcttggt accagcagaa gccaggacag    240
cctcctaagc tgctcatttt actgggcatct acccgggaat ccggggtccc tgaccgattc    300
agtggcagcg gtctgggac agatttcact ctcaccatca gcagcctgca ggctgaagat    360
gtggcagttt attactgtca gcaatattat agtactcctc gacgttcgg ccaagggacc    420 aaggtggaaa tcaaacgaac tgtggctgca ccatctgtct tcatcttccc gccatctgat    480
gagcagttga atctggaac tgcctctgtt gtgtgcctgc tgaataactt ctatcccaga    540
gaggccaaag tacagtggaa ggtggataac gccctccaat cgggtaactc caggagagt    600 gtcacagagc aggacagcaa ggacagcacc tacagcctca gcagcaccct gacgctgagc    660
aaagcagact acgagaaaca caaagtctac gcctgcgaag tcacccatca gggcctgagc    720
tcgcccgtca caaagagctt caacagggga gagtgttagg cggccgcaag cttggccgcc    780
atggcccaac ttgtttattg cagcttataa tggttacaaa taaagcaata gcatcacaaa    840
tttcacaaat aaagcatttt tttcactgca ttctagttgt ggtttgtcca actc          894
```

<210> SEQ ID NO 20
<211> LENGTH: 903
<212> TYPE: DNA
<213> ORGANISM: Artificial Sequence
<220> FEATURE:
<223> OTHER INFORMATION: cDNA 25.6A LC variable region

<400> SEQUENCE: 20

```
ctcggttcta tcgattggct agcaccatgg agacagacac actcctgcta tgggtactgc     60
tgctctgggt tccaggttcc actggtgacc tgcctgtgct gactcagcct gcctccgtgt    120
ctgggtctcc tggacagtcg atcaccatct cctgcactgg aaccagcagt gacgttggtg    180
gttataacta tgtctcctgg taccaacagc acccaggcaa agcccccaaa ctcataattt    240
atgaagtcaa gattcggccg tcaggggtgt ctaatcgttt ctctggctcc aagtctggca    300
acacggcctc cctgaccatc tctgggctcc aggctgagga cgaggctgat tattttttgca    360 gctcatattc aaccaacagc ccttgggtgt cggcggagg gacgaaggtg accgtcctac    420
gtcagcccaa ggctgccccc tcggtcactc tgttcccacc ctcctctgag gagcttcaag    480
ccaacaaggc cacactggtg tgtctcataa gtgacttcta cccgggagcc gtgacagtgg    540
cctggaaggc agatagcagc cccgtcaagg cgggagtgga gaccaccaca ccctccaaac    600
aaagcaacaa caagtacgcg gccagcagct acctgagcct gacgcctgag cagtggaagt    660
cccacagaag ctacagctgc caggtcacgc atgaagggag caccgtggag aagacagtgg    720
```

```
cccctacaga atgttcatga gcggccgcaa gcttggccgc catggcccaa cttgtttatt    780
gcagcttata atggttacaa ataaagcaat agcatcacaa atttcacaaa taaagcattt    840
ttttcactgc attctagttg tggtttgtcc aaactcatca atgtatctta tcatgtctgg    900
atc                                                                 903
```

<210> SEQ ID NO 21
<211> LENGTH: 900
<212> TYPE: DNA
<213> ORGANISM: Artificial Sequence
<220> FEATURE:
<223> OTHER INFORMATION: cDNA 36.1F LC variable region

<400> SEQUENCE: 21

```
tccaggtcac tgcacctcgg ttctatcgat tggctagcac catggagaca gacacactcc     60
tgctatgggt actgctgctc tgggttccag gttccactgg tgacgaaatt gtgctgacac    120
agtctccagg cacccgtgtct ttgtctccag gggaagagc accctctcc tgcagggcca    180 gtcagagtgt tactaaaaac tacttagcct ggtaccagca gaaacctggc caggctccca    240
ccctcgtcat ctatgatgca tccaccaggg ccagtggcat cccagacagg ttcattggca    300
gtgggtctgg gacagacttc actctcacca tcagcagact ggagcctgaa gattttgcag    360
tatattactg ccaccagtat ggcagctcac ctccgtacac ttttggccgg gggaccaagc    420
tggagatcaa acgaactgtg gctgcaccat ctgtcttcat cttcccgcca tctgatgagc    480
agttgaaatc tggaactgcc tctgttgtgt gcctgctgaa taacttctat cccagagagg    540
ccaaagtaca gtggaaggtg gataacgccc tccaatcggg taactcccag gagagtgtca    600
cagagcagga cagcaaggac agcacctaca gcctcagcag caccctgacg ctgagcaaag    660
cagactacga gaaacacaaa gtctacgcct gcgaagtcac ccatcagggc ctgagctcgc    720
ccgtcacaaa gagcttcaac aggggagagt gttaggcggc cgcaagcttg gccgccatgg    780
cccaacttgt ttattgcagc ttataatggt tacaaataaa gcaatagcat cacaaatttc    840
acaaataaag catttttttc actgcattct agttgtgggt tgtccaaact catcaatgta    900
```

<210> SEQ ID NO 22
<211> LENGTH: 922
<212> TYPE: DNA
<213> ORGANISM: Artificial Sequence
<220> FEATURE:
<223> OTHER INFORMATION: cDNA 36.9F LC variable region

<400> SEQUENCE: 22

```
aggtcactgc acctcggttc tatcgattgg ctagcaccat ggagacagac acactcctgc     60
tatgggtact gctgctctgg gttccaggtt ccactggtga cgacatcgtg atgacccagt    120
ctccagactc cctggctgtg tctctgggcg agagggccac catcaactgc aagtccagcc    180
agactgtttt gttcacctcc tattacgtag cttggtatca acaaaagcca gggcagccgc    240
ctaagttgct cttttccggg gcctcttctc gggaatccgg ggtccctgac cgattcagtg    300
ccggcgggtc tgggacagat ttctatctca ccatcaacag cctgcaggct gaagatgtgg    360
cagattacta ttgtcagcaa tatcatactc tccctttcac tttcggcgga gggaccaagc    420
tggagatcag acgaactgtg gctgcaccat ctgtcttcat cttcccgcca tctgatgagc    480
agttgaaatc tggaactgcc tctgttgtgt gcctgctgaa taacttctat cccagagagg    540
ccaaagtaca gtggaaggtg gataacgccc tccaatcggg taactcccag gagagtgtca    600
cagagcagga cagcaaggac agcacctaca gcctcagcag caccctgacg ctgagcaaag    660
```

| | |
|---|---|
| cagactacga gaaacacaaa gtctacgcct gcgaagtcac ccatcagggc ctgagctcgc | 720 |
| ccgtcacaaa gagcttcaac aggggagagt gttaggcggc cgcaagcttg gccgccatgg | 780 |
| cccaacttgt ttattgcagc ttataatggt tacaaataaa gcaatagcat cacaaatttc | 840 |
| acaaataaag cattttttc actgcattct agttgtggtt tgtccaaact catcaatgta | 900 |
| tcttatcatg tctggatcgg ga | 922 |

<210> SEQ ID NO 23
<211> LENGTH: 858
<212> TYPE: DNA
<213> ORGANISM: Artificial Sequence
<220> FEATURE:
<223> OTHER INFORMATION: cDNA 37.2D LC variable region

<400> SEQUENCE: 23

| | |
|---|---|
| tcactgcacc tcggttctat cgattggcta gcaccatgga gacagacaca ctcctgctat | 60 |
| gggtactgct gctctgggtt ccaggttcca ctggtgacga aacgactc acgcagtctc | 120 |
| cagccaccct gtctgtgtct caggggaaa cagccaccct ctcctgcagg gccagtcaaa | 180 |
| atgttatcaa caacttagcc tggtaccagc agaaacctgg ccaggctccc aggctcctca | 240 |
| tttatggtgc atccaccagg gccactggta tcccagccag gttcagtggc agtgggtctg | 300 |
| ggacagagtt cactctcacc atcagcagca tgcagtctga agattttgca gtttattact | 360 |
| gtcagcaata taatgactgg cctcgaagtt ttggccaggg gaccaggctg gacatcagac | 420 |
| gaactgtggc tgcaccatct gtcttcatct cccgccatc tgatgagcag ttgaaatctg | 480 |
| gaactgcctc tgttgtgtgc ctgctgaata acttctatcc cagagaggcc aaagtacagt | 540 |
| ggaaggtgga taacgccctc caatcgggta actcccagga gagtgtcaca gagcaggaca | 600 |
| gcaaggacag cacctacagc ctcagcagca ccctgacgct gagcaaagca gactacgaga | 660 |
| aacacaaagt ctacgcctgc gaagtcaccc atcagggcct gagctcgccc gtcacaaaga | 720 |
| gcttcaacag gggagagtgt taggcggccg caagcttggc cgccatggcc caacttgttt | 780 |
| attgcagctt ataatggtta caaataaagc aatagcatca caaatttcac aaataaagca | 840 |
| tttttttcac tgcattct | 858 |

<210> SEQ ID NO 24
<211> LENGTH: 958
<212> TYPE: DNA
<213> ORGANISM: Artificial Sequence
<220> FEATURE:
<223> OTHER INFORMATION: cDNA 37.7G LC variable region

<400> SEQUENCE: 24

| | |
|---|---|
| tccaggtcac tgccctcggt tctatcgatt ggctagcacc atggagacag acacactcct | 60 |
| gctatgggta ctgctgctct gggttccagg ttccactggt gacgacattg tgctgaccca | 120 |
| gtctccaggc accctgtctt tgtctccagg ggaaagagcc accctctcct gcagggccag | 180 |
| tcagagtgtg aacagcatct tcttagcctg gtaccagcag aaacctggcc aggctcccag | 240 |
| gctcctcatc tatggtgcat ccagcagggc cactggcatc ccagacaggt tcagtggcag | 300 |
| tgggtctggg acagacttca ctctcaccat cagcagactg gagcctgagg attttgcagt | 360 |
| gtattactgt cagcagtatc atagctcacc taagctcact ttcggcggag ggaccaaggt | 420 |
| ggagatcaaa cgaactgtgg ctgcaccatc tgtcttcatc ttcccgccat ctgatgagca | 480 |
| gttgaaatct ggaactgcct ctgttgtgtg cctgctgaat aacttctatc ccagagaggc | 540 |

| | |
|---|---|
| caaagtacag tggaaggtgg ataacgccct ccaatcgggt aactcccagg agagtgtcac | 600 |
| agagcaggac agcaaggaca gcacctacag cctcagcagc accctgacgc tgagcaaagc | 660 |
| agactacgag aaacacaaag tctacgcctg cgaagtcacc catcagggcc tgagctcgcc | 720 |
| cgtcacaaag agcttcaaca ggggagagtg ttaggcggcc gcaagcttgg ccgccatggc | 780 |
| ccaacttgtt tattgcagct tataatggtt acaaataaag caatagcatc acaaatttca | 840 |
| caaataaagc attttttca ctgcattcta gttgtggttt gtccaaactc atcaatgtat | 900 |
| cttatcatgt ctggatcggg aattaattcg gcgcagcacc atggcctgaa ataacctc | 958 |

<210> SEQ ID NO 25
<211> LENGTH: 1015
<212> TYPE: DNA
<213> ORGANISM: Artificial Sequence
<220> FEATURE:
<223> OTHER INFORMATION: cDNA 37.7H LC variable region

<400> SEQUENCE: 25

| | |
|---|---|
| tcactgcacc tcggttctat cgattggcta gcaccatgga gacagacaca ctcctgctat | 60 |
| gggtactgct gctctgggtt ccaggttcca ctggtgacca gtctgccctg actcagcctg | 120 |
| cctccgtgtc tgggtctcct ggacagtcga tcaccatctc ctgcactgga accggcagtg | 180 |
| acattggtgg ttataacttt gtctcctggt accaacagta tcccggcaaa gcccccaaac | 240 |
| tcattattta tgaggtccgt attcgggcct caggggtttc caatcgcttc tctggctcca | 300 |
| agtctggcaa cacggcctcc ctgaccatct ctggactcca ggctgaggac gaggctgatt | 360 |
| attactgcaa ctcatattca atccacagcc ttgggtgtt cggcggaggg accaagttga | 420 |
| ccgtcctgcg tcagcccaag gctgccccct cggtcactct gttcccaccc tcctctgagg | 480 |
| agcttcaagc caacaaggcc acactggtgt gtctcataag tgacttctac ccgggagccg | 540 |
| tgacagtggc ctgaaggca gatagcagcc ccgtcaaggc gggagtggag accaccacac | 600 |
| cctccaaaca aagcaacaac aagtacgcgg ccagcagcta cctgagcctg acgcctgagc | 660 |
| agtgggagtc ccacagaagc tacagctgcc aggtcacgca tgaagggagc accgtggaga | 720 |
| agacagtggc ccctacagaa tgttcatgag cggccgcaag cttggccgcc atggcccaac | 780 |
| ttgtttattg cagcttataa tggttacaaa taaagcaata gcatcacaaa tttcacaaat | 840 |
| aaagcatttt tttcactgca ttctagttgt ggtttgtcca aactcatcaa tgtatcttat | 900 |
| catgtctgga tcgggaatta attcggcgca gcaccatggc ctgaaatacc ctctgaaaga | 960 |
| ggaacttggt taggtacctt ctgaggcgga agaaccatc tgtggaatgt gtgtc | 1015 |

<210> SEQ ID NO 26
<211> LENGTH: 910
<212> TYPE: DNA
<213> ORGANISM: Artificial Sequence
<220> FEATURE:
<223> OTHER INFORMATION: cDNA 8.9F LC variable region

<400> SEQUENCE: 26

| | |
|---|---|
| cactgccctc ggttctatcg attggctagc accatggaga cagacacact cctgctatgg | 60 |
| gtactgctgc tctgggttcc aggttccact ggtgaccagg cagggctgac tcagcctgcc | 120 |
| tccgtgtctg ggtctcctgg acagtcgatc accatctcct gcactgcagc caacagtgac | 180 |
| attggtgatt taactttgt ctcctggtac caacagcgcc cagacaaagc ccccaaactc | 240 |
| atggtttatg aggtcagcag tcggccctca ggggttctta tcgcttctc tggctccaag | 300 |
| tctggcaaca cggcctccct gaccatctct gggctccagg ctgaggacga ggctgattat | 360 |

```
tactgcacct catatacaag cagcagcact tttgtcttcg aactgggac caaggtcacc      420 gtcctaggtc agcccaaggc aaccccact gtcactctgt tcccgccctc ctctgaggag       480
cttcaagcca acaaggccac actggtgtgt ctcataagtg acttctaccc gggagccgtg      540
acagtggcct ggaaggcaga tagcagcccc gtcaaggcgg gagtggagac caccacaccc     600
tccaaacaaa gcaacaacaa gtacgcggcc agcagctacc tgagcctgac gcctgagcag     660
tggaagtccc acagaagcta cagctgccag gtcacgcatg aagggagcac cgtggagaag     720
acagtggccc ctacagaatg ttcatgagcg ccgcaagct tggccgccat ggcccaactt      780
gtttattgca gcttataatg gttacaaata aagcaatagc atcacaaatt tcacaaataa     840 agcattttt tcactgcatt ctagttgtgg tttgtccaaa ctcatcaatg tatcttatca      900
tgtctggatc                                                             910

<210> SEQ ID NO 27
<211> LENGTH: 908
<212> TYPE: DNA
<213> ORGANISM: Artificial Sequence
<220> FEATURE:
<223> OTHER INFORMATION: cDNA NE13 LC variable region

<400> SEQUENCE: 27
ctcccaggtc actgcacctc ggttctatcg attggctagc accatggaga cagacacact      60
cctgctatgg gtactgctgc tctgggttcc aggttccact ggtgacgaaa cgacactcac     120
gcagtctcca ggcaccctgt ctttgtctcc aggggaaaga gccaccctct cctgcagggc     180
cagtcagagt gttagcagca cctacttagc ctggtaccag cagaaacctg gccagtctcc     240
caggctcctc atttatggtg catccagtag ggccactggc atcccagaca ggttcagtgg     300
cagtgggtct gggacacagt tcactctcac catcaacaga ctggagcctg aagattttgc     360
agtgtattac tgtcagcagt ttggtagccc gtggacattc ggccaaggga ccaaggtgga     420
aatcaaacga actgtggctg caccatctgt cttcatcttc ccgccatctg atgagcagtt     480
gaaatctgga actgcctctg ttgtgtgcct gctgaataac ttctatccca gagaggccaa     540
agtacagtgg aaggtggata acgccctcca atcgggtaac tcccaggaga gtgtcacaga     600
gcaggacagc aaggacagca cctacagcct cagcagcacc ctgacgctga gcaaagcaga     660
ctacgagaaa cacaaagtct acgcctgcga agtcacccat cagggcctga gctcgcccgt     720
cacaaagagc ttcaacaggg gagagtgtta ggcggccgca agcttggccg ccatggccca     780
acttgtttat tgcagcttat aatggttaca aataaagcaa tagcatcaca aatttcacaa     840
ataaagcatt ttttcactg cattctagtt gtggtttgtc caaactcatc aatgtatctt      900
atcatgtc                                                              908

<210> SEQ ID NO 28
<211> LENGTH: 932
<212> TYPE: DNA
<213> ORGANISM: Artificial Sequence
<220> FEATURE:
<223> OTHER INFORMATION: cDNA 12.1F LC variable region

<400> SEQUENCE: 28
gtcactgcac ctcggttcta tcgattggct agcaccatgg agacagacac actcctgcta      60
tgggtactgc tgctctgggt tccaggttcc actggtgacg aaacgacact cacgcagtct    120
ccagccaccc tgtctttgtc tccaggggag agagccaccc tctcctgtag ggccagtcag    180
```

| | |
|---|---|
| agtgttagca gctacttagc ctggtaccaa cacaaacctg gccaggctcc caggctcctc | 240 |
| atctatggtg catcaaagag ggccactggc atcccgtcca ggttcagtgg cagtgggtct | 300 |
| gggacagact tcagtctcac catcagcagc ctagagcctg aagattttgc agtttactac | 360 |
| tgtcagcacc gaagcgactg gcggactacc ttcggccaag gacacgact ggagattaaa | 420 |
| cgaactgtgg ctgcaccatc tgtcttcatc ttcccgccat ctgatgagca gttgaaatct | 480 |
| ggaactgcct ctgttgtgtg cctgctgaat aacttctatc ccagagaggc caaagtacag | 540 |
| tggaaggtgg ataacgccct ccaatcgggt aactcccagg agagtgtcac agagcaggac | 600 |
| agcaaggaca gcacctacag cctcagcagc accctgacgc tgagcaaagc agactacgag | 660 |
| aaacacaaag tctacgcctg cgaagtcacc catcagggcc tgagctcgcc cgtcacaaag | 720 |
| agcttcaaca ggggagagtg ttaggcggcc gcaagcttgg ccgccatggc ccaacttgtt | 780 |
| tattgcagct tataatggtt acaaataaag caatagcatc acaaatttca caaataaagc | 840 |
| atttttttca ctgcattcta gttgtggttt gtccaaactc atcaatgtat cttatcatgt | 900 |
| ctggatcggg aaattaatcg gcgcagcacc at | 932 |

<210> SEQ ID NO 29
<211> LENGTH: 895
<212> TYPE: DNA
<213> ORGANISM: Artificial Sequence
<220> FEATURE:
<223> OTHER INFORMATION: cDNA 9.8A LC variable region

<400> SEQUENCE: 29

| | |
|---|---|
| ggttctatcg attggctagc accatggaga cagacacact cctgctatgg gtactgctgc | 60 |
| tctgggttcc aggttccact ggtgacgaca tcgtgatgac ccagtctcct tccaccctgt | 120 |
| ctgcatctgt aggagacaga gtcaccatca cttgccgggc cagtcagagt attgataggt | 180 |
| ggttggcctg gtatcagcag aaaccaggga agcccctaa gctcctgatc tatcaggcat | 240 |
| ctagtttaga aagaggggtc ccatcaaggt tcagcggcag tggatctggg acagaattca | 300 |
| ctctcaccat cagcagcctg cagcccgatg attttgcaac ttattactgc caacagtata | 360 |
| atggttaccc tctcactttc ggcggaggga ccaaggtgga gatcaaacga actgtggctg | 420 |
| caccatctgt cttcatcttc ccgccatctg atgagcagtt gaaatctgga actgcctctg | 480 |
| ttgtgtgcct gctgaataac ttctatccca gagaggccaa agtacagtgg aaggtggata | 540 |
| acgccctcca atcgggtaac tcccaggaga gtgtcacaga gcaggacagc aaggacagca | 600 |
| cctacagcct cagcagcacc ctgacgctga gcaaagcaga ctacgagaaa cacaaagtct | 660 |
| acgcctgcga agtcacccat cagggcctga gctcgcccgt cacaaagagc ttcaacaggg | 720 |
| gagagtgtta ggcggccgca agcttggccg ccatggccca acttgtttat tgcagcttat | 780 |
| aatggttaca aataaagcaa tagcatcaca aatttcacaa ataaagcatt ttttcactg | 840 |
| cattctagtt gtggtttgtc caaactcatc aatgtatctt atcatgtctg gatcg | 895 |

<210> SEQ ID NO 30
<211> LENGTH: 784
<212> TYPE: DNA
<213> ORGANISM: Artificial Sequence
<220> FEATURE:
<223> OTHER INFORMATION: cDNA 18.5C LC variable region

<400> SEQUENCE: 30

| | |
|---|---|
| tccaggtcca ctgcacctcg gttctatcga ttggctagca ccatggagac agacacactc | 60 |
| ctgctatggg tactgctgct ctgggttcca ggttccactg gtgacgacat ccagatgacc | 120 |

```
cagtctccag gcaccctgtc tttgtctcca ggggaaagag ccaccctctc ctgcagggcc      180
agtcagagtg ttatcagtta ctacgtagcc tggtaccagc acaaaggtgg ccaggctccc      240
aggctcctca tttatggtgc atccagcagg gccactggcg tcccagacag gttcagtggc      300
agtgggtctg ggacagactt cactctcacc atcagcagcc tggagcctga agattttgca      360
ctgtattact gtcagtacta tgggagctca cctctgtggg cgttcggcca agggaccaag      420
gtggaaatca aacgaactgt ggctgcacca tctgtcttca tcttcccgcc atctgatgag      480
cagttgaaat ctggaactgc ctctgttgtg tgcctgctga ataacttcta tcccagagag      540
gccaaagtac agtggaaggt ggataacgcc ctccaatcgg gtaactccca ggagagtgtc      600
acagagcagg acagcaagga cagcacctac agcctcagca gcaccctgac gctgagcaaa      660
gcagactacg agaaacacaa agtctacgcc tgcgaagtca cccatcaggg cctgagctcg      720
cccgtcacaa agagcttcaa caggggagag tgttaggcgg ccgcaagctt ggccgccatg      780
gccc                                                                    784

<210> SEQ ID NO 31
<211> LENGTH: 845
<212> TYPE: DNA
<213> ORGANISM: Artificial Sequence
<220> FEATURE:
<223> OTHER INFORMATION: cDNA 8.11G LC variable region

<400> SEQUENCE: 31
cggttctatc gattggctag caccatggag acagacacac tcctgctatg ggtactgctg       60
ctctgggttc caggttccac tggtgacgaa attgtgctga ctcagtctcc agccaccctg      120
tctgtgtctc caggggggtag ggcctccctc tcctgccggg ccagtcagag tattggcgac      180
aagttatcct ggtatcagca gaaacctggg caggctccca ggctcgtcat ctatggtgca      240
tataccaggg ccactgatat ctcacccagg ttcagtggca gtaggtctgg gacagacttc      300
aatctcacca tcagcagaat gcagtctgga gactttgcag tttatttctg tcagcagtat      360
gaaaactggc ctcggacttt tggccagggg accaagctgg agatcaaacg aactgtggct      420
gcaccatctg tcttcatctt cccgccatct gatgagcagt tgaaatctgg aactgcctct      480
gttgtgtgcc tgctgaataa cttctatccc agagaggcca agtacagtg gaaggtggat      540 aacgccctcc aatcgggtaa ctcccaggag agtgtcacag agcaggacag caaggacagc      600
acctacagcc tcagcagcac cctgacgctg agcaaagcag actacgagaa acacaaagtc      660
tacgcctgca agtcacccca tcagggcctg agctcgcccg tcacaaagag cttcaacagg      720
ggagagtgtt aggcggccgc aagcttggcc gccatggccc aacttgttta ttgcagctta      780
taatggttac aaataaagca atagcatcac aaatttcaca ataaagcat tttttcact      840 gcatt                                                                  845

<210> SEQ ID NO 32
<211> LENGTH: 900
<212> TYPE: DNA
<213> ORGANISM: Artificial Sequence
<220> FEATURE:
<223> OTHER INFORMATION: cDNA 25.10C LC variable region

<400> SEQUENCE: 32
cctcggttct atcgattggc tagcaccatg gagacagaca cactcctgct atgggtactg       60
ctgctctggg ttccaggttc cactggtgac gacatccaga tgacccagtc tccatcctcc      120
```

```
ctgtctgcat ctgttggaga cagagtcatc atcacttgcc gggcaagtca gagcatcagc    180
agctctttaa attggtatca gcagaaacca gggaaagccc ctaagctcct gatctatgct    240
gcagtcaatt tggagactgg ggtcccgtca aggttcagtg gcagtggatt tgggacagat    300
ttcactctcg ccatcagcaa tgtgcaacct gaagattttg caacttacta ctgtcaacag    360
agcgatactc ggacttttgg ccgggggacc aagctggacg tcaaacgaac tgtggctgca    420
ccatctgtct tcatcttccc gccatctgat gagcagttga aatctggaac tgcctctgtt    480
gtgtgcctgc tgaataactt ctatcccaga gaggccaaag tacagtggaa ggtggataac    540
gccctccaat cgggtaactc ccaggagagt gtcacagagc aggacagcaa ggacagcacc    600
tacagcctca gcagcaccct gacgctgagc aaagcagact acgagaaaca caaagtctac    660
gcctgcgaag tcacccatca gggcctgagc tcgcccgtca caaagagctt caacagggga    720
gaagtgttag gcggccgcaa gcttggccgc catggcccaa cttgtttatt gcagcttata    780
atggttacaa ataaagcaat agcatcacaa atttcacaaa taaagcattt ttttcactgc    840
attctagttg tggtttgtcc aaactcatca atgtatctta tcatgtctgg atcgggaatt    900
```

<210> SEQ ID NO 33
<211> LENGTH: 203
<212> TYPE: PRT
<213> ORGANISM: Artificial Sequence
<220> FEATURE:
<223> OTHER INFORMATION: HC variable region

<400> SEQUENCE: 33

```
Met Glu Thr Asp Thr Leu Leu Leu Trp Val Leu Leu Leu Trp Val Pro
1               5                   10                  15

Gly Ser Thr Gly Asp Gln Val Gln Leu Val Gln Ser Gly Gly Gly Val
            20                  25                  30

Val Gln Pro Gly Arg Ser Leu Arg Val Ser Cys Val Thr Ser Gly Phe
        35                  40                  45

Asn Phe Arg Ala Tyr Gly Met His Trp Val Arg Gln Ile Pro Gly Lys
    50                  55                  60

Gly Leu Glu Trp Val Ala Asp Ile Trp Ser Ala Glu Thr Asn Arg His
65                  70                  75                  80

Tyr Ala Asp Ser Val Lys Gly Arg Phe Thr Ile Ser Arg Asp Asn Ser
                85                  90                  95

Lys Ser Thr Leu Tyr Leu Gln Met Asn Ser Leu Arg Ala Glu Asp Thr
            100                 105                 110

Gly Val Tyr Phe Cys Ala Lys Ala Arg Pro Gly Tyr Asp Tyr Val Val
        115                 120                 125

Asp Leu Trp Gly Gln Gly Thr Leu Val Ile Val Ser Ser Ala Ser Thr
    130                 135                 140

Lys Gly Pro Ser Val Phe Pro Leu Ala Pro Cys Ser Arg Ser Thr Ser
145                 150                 155                 160

Gly Gly Thr Ala Ala Leu Gly Cys Leu Val Lys Asp Tyr Phe Pro Glu
                165                 170                 175

Pro Val Thr Val Ser Trp Asn Ser Gly Ala Leu Thr Ser Gly Val His
            180                 185                 190

Thr Phe Pro Ala Val Leu Gln Ser Ser Gly Leu
        195                 200
```

<210> SEQ ID NO 34
<211> LENGTH: 258
<212> TYPE: PRT

<213> ORGANISM: Artificial Sequence
<220> FEATURE:
<223> OTHER INFORMATION: HC variable region

<400> SEQUENCE: 34

Met Glu Thr Asp Thr Leu Leu Leu Trp Val Leu Leu Trp Val Pro
1               5                   10                  15

Gly Ser Thr Gly Asp Glu Val Gln Leu Val Glu Ser Gly Gly Leu
                20                  25                  30

Val Arg Pro Gly Gly Ser Leu Arg Leu Ser Cys Ala Ala Ser Gly Phe
            35                  40                  45

Ser Phe Ser Ser Tyr Ser Met His Trp Val Arg His Val Pro Gly Lys
    50                  55                  60

Gly Leu Val Trp Val Ser Tyr Ile Asn Ser Asp Gly Ser Thr Lys Ile
65                  70                  75                  80

Tyr Ala Asp Ser Val Lys Gly Arg Phe Ser Ile Ser Arg Asp Asn Ala
                85                  90                  95

Lys Asn Lys Leu Tyr Leu Gln Met Asp Ser Leu Arg Val Glu Asp Thr
                100                 105                 110

Ala Val Tyr Ser Cys Val Arg Leu Val His Tyr Asp Trp Ser Pro Phe
            115                 120                 125

Val Trp Gly Gln Gly Thr Leu Val Thr Val Ser Ser Ala Ser Thr Lys
130                 135                 140

Gly Pro Ser Val Phe Pro Leu Ala Pro Ser Ser Lys Ser Thr Ser Gly
145                 150                 155                 160

Gly Thr Ala Ala Leu Gly Cys Leu Val Lys Asp Tyr Phe Pro Glu Pro
                165                 170                 175

Val Thr Val Ser Trp Asn Ser Gly Ala Leu Thr Ser Gly Val His Thr
            180                 185                 190

Phe Pro Ala Val Leu Gln Ser Ser Gly Leu Tyr Ser Leu Ser Ser Val
        195                 200                 205

Val Thr Val Pro Ser Ser Leu Gly Thr Gln Thr Tyr Ile Cys Asn
    210                 215                 220

Val Asn His Lys Pro Ser Asn Thr Lys Val Asp Lys Lys Val Glu Pro
225                 230                 235                 240

Gln Ser Cys Asp Lys Thr His Thr Cys Pro Pro Cys Pro Ala Pro Glu
                245                 250                 255

Leu Leu

<210> SEQ ID NO 35
<211> LENGTH: 294
<212> TYPE: PRT
<213> ORGANISM: Artificial Sequence
<220> FEATURE:
<223> OTHER INFORMATION: HC variable region

<400> SEQUENCE: 35

Met Glu Thr Asp Thr Leu Leu Leu Trp Val Leu Leu Trp Val Pro
1               5                   10                  15

Gly Ser Thr Gly Asp Glu Val Gln Leu Val Glu Ser Gly Gly Leu
                20                  25                  30

Val Lys Pro Gly Gly Ser Leu Arg Leu Ser Cys Ala Ala Ser Gly Phe
            35                  40                  45

Thr Phe Thr Arg Phe Thr Leu Thr Trp Val Arg Gln Ala Pro Gly Lys
    50                  55                  60

Gly Leu Glu Trp Val Ser Ser Ile Ser Ser Gly Ser Ser Asp Ile Asn

```
                65                  70                  75                  80
        Tyr Ala Asp Ser Val Lys Gly Arg Phe Thr Ile Ser Arg Asp Asn Ala
                        85                  90                  95

Arg Asn Ser Leu Phe Leu Gln Met Ser Ser Leu Arg Val Asp Asp Thr
                        100                 105                 110

Ala Val Tyr Tyr Cys Ala Lys Asp Pro Arg Ser Gly Ile Ser Gly Arg
                        115                 120                 125

Tyr Gly Met Asp Val Trp Gly Gln Gly Thr Thr Val Ile Val Ser Ser
                        130                 135                 140

Ala Ser Thr Lys Gly Pro Ser Val Phe Pro Leu Ala Pro Cys Ser Arg
        145                 150                 155                 160

Ser Thr Ser Gly Gly Thr Ala Ala Leu Gly Cys Leu Val Lys Asp Tyr
                        165                 170                 175

Phe Pro Glu Pro Val Thr Val Ser Trp Asn Ser Gly Ala Leu Thr Ser
                        180                 185                 190

Gly Val His Thr Phe Pro Ala Val Leu Gln Ser Ser Gly Leu Tyr Ser
                        195                 200                 205

Leu Ser Ser Val Val Thr Val Pro Ser Ser Ser Leu Gly Thr Gln Thr
                210                 215                 220

Tyr Ile Cys Asn Val Asn His Lys Pro Ser Asn Thr Lys Val Asp Lys
        225                 230                 235                 240

Arg Val Glu Pro Lys Ser Cys Asp Lys Thr His Thr Cys Pro Pro Cys
                        245                 250                 255

Pro Ala Pro Glu Leu Leu Gly Gly Pro Ser Val Phe Leu Phe Pro Pro
                        260                 265                 270

Lys Pro Lys Asp Thr Leu Met Ile Ser Arg Thr Pro Glu Val Thr Cys
                        275                 280                 285

Val Val Val Asp Val Ser
                        290

<210> SEQ ID NO 36
<211> LENGTH: 171
<212> TYPE: PRT
<213> ORGANISM: Artificial Sequence
<220> FEATURE:
<223> OTHER INFORMATION: HC variable region

<400> SEQUENCE: 36

Met Glu Thr Asp Thr Leu Leu Leu Trp Val Leu Leu Leu Trp Val Pro
1               5                   10                  15

Gly Ser Thr Gly Asp Gln Val Gln Leu Gln Glu Ser Gly Gly Gly Leu
                20                  25                  30

Val Lys Ala Gly Gly Ser Leu Arg Leu Ser Cys Ala Ala Ser Gly Phe
            35                  40                  45

Met Phe Glu Arg Tyr Ser Leu His Trp Val Arg Gln Thr Pro Gly Lys
        50                  55                  60

Gly Leu Glu Trp Val Ser Ser Ile Ser Ser Leu Ser Gly Ser His Ile
65                  70                  75                  80

Asn Tyr Ala Asp Ser Val Lys Gly Arg Phe Thr Ile Ser Arg Asp Asn
                85                  90                  95

Ala Lys Asn Ser Leu Ser Leu Gln Met Asn Ser Leu Arg Val Glu Asp
                100                 105                 110

Thr Ala Ile Tyr Tyr Cys Ala Arg Asp Arg Arg Ser Gly Ser Ser Pro
                115                 120                 125

Val Pro Leu Asp Val Trp Gly Gln Gly Thr Thr Val Thr Val Ser Ser
```

```
                130                 135                 140
Ala Ser Thr Lys Gly Pro Ser Val Phe Pro Leu Ala Pro Ser Lys
145                 150                 155                 160

Ser Thr Ser Gly Gly Thr Ala Ala Leu Gly Cys
                165                 170

<210> SEQ ID NO 37
<211> LENGTH: 274
<212> TYPE: PRT
<213> ORGANISM: Artificial Sequence
<220> FEATURE:
<223> OTHER INFORMATION: HC variable region
<221> NAME/KEY: VARIANT
<222> LOCATION: 274
<223> OTHER INFORMATION: Xaa = unknown amino acid

<400> SEQUENCE: 37

Met Glu Thr Asp Thr Leu Leu Leu Trp Val Leu Leu Leu Trp Val Pro
1               5                   10                  15

Gly Ser Thr Gly Asp Gln Val Gln Leu Gln Glu Ser Gly Ala Gly Leu
            20                  25                  30

Val Lys Pro Ser Glu Thr Leu Ser Leu Thr Cys Ala Val Ser Gly Gly
        35                  40                  45

Pro Phe Ser Gly Ala Tyr Trp Thr Trp Ile Arg Gln Thr Pro Gly Lys
    50                  55                  60

Gly Leu Glu Trp Ile Gly Glu Ala Gly Arg Ser Gly Thr Thr Asn Tyr
65                  70                  75                  80

Asn Pro Ser Leu Lys Ser Arg Val Thr Ile Ser Leu Asp Thr Ser Lys
                85                  90                  95

Ser Gln Phe Ser Leu Lys Leu Thr Ser Val Thr Ala Ala Asp Thr Ala
            100                 105                 110

Val Tyr Phe Cys Gly Arg Arg Gln Ile Met Ser Leu Ser Asn Leu Tyr
        115                 120                 125

Lys Arg Pro Val Asp Ser Trp Gly Arg Gly Thr Pro Val Ile Val Ser
    130                 135                 140

Ser Ala Ser Thr Lys Gly Pro Ser Val Phe Pro Leu Ala Pro Ser Ser
145                 150                 155                 160

Lys Ser Thr Ser Gly Gly Thr Ala Ala Leu Gly Cys Leu Val Lys Asp
                165                 170                 175

Tyr Phe Pro Glu Pro Val Thr Val Ser Trp Asn Ser Gly Ala Leu Thr
            180                 185                 190

Ser Gly Val His Thr Phe Pro Ala Val Leu Gln Ser Ser Gly Leu Tyr
        195                 200                 205

Ser Leu Ser Ser Val Val Thr Val Pro Ser Ser Ser Leu Gly Thr Gln
    210                 215                 220

Thr Tyr Ile Cys Asn Val Asn His Lys Pro Ser Asn Thr Lys Val Asp
225                 230                 235                 240

Lys Arg Val Glu Pro Lys Ser Cys Asp Lys Thr His Thr Cys Pro Pro
                245                 250                 255

Cys Pro Ala Pro Glu Leu Leu Gly Gly Pro Ser Val Phe Leu Phe Pro
            260                 265                 270

Pro Xaa

<210> SEQ ID NO 38
<211> LENGTH: 279
<212> TYPE: PRT
<213> ORGANISM: Artificial Sequence
```

```
<220> FEATURE:
<223> OTHER INFORMATION: HC variable region

<400> SEQUENCE: 38

Met Glu Thr Asp Thr Leu Leu Leu Trp Val Leu Leu Trp Val Pro
1               5                   10                  15

Gly Ser Thr Gly Asp Glu Val Gln Leu Val Gln Ser Gly Gly Leu
                20                  25                  30

Val Lys Ala Gly Gly Ser Leu Lys Leu Ser Cys Gly Ala Ser Gly Phe
            35                  40                  45

Thr Phe Ser Ser Tyr Ser Met Ser Trp Val Arg Gln Ala Pro Gly Lys
        50                  55                  60

Gly Leu Glu Trp Val Ser Tyr Ile Ser Ser Gly Ser Ser Ile His
65                  70                  75                  80

Tyr Ala Asp Ser Val Lys Gly Arg Phe Thr Ile Ser Arg Asp Asn Ala
                85                  90                  95

Lys Asn Ser Leu Tyr Leu Gln Met Lys Asn Leu Arg Val Asp Asp Thr
            100                 105                 110

Gly Arg Tyr Tyr Cys Val Arg Asp Pro Arg Ser Gly Ile Ser Gly Arg
        115                 120                 125

Tyr Gly Met Asp Val Trp Gly Gln Gly Thr Thr Val Thr Val Ser Ser
    130                 135                 140

Ala Ser Thr Lys Gly Pro Ser Val Phe Pro Leu Ala Pro Ser Ser Lys
145                 150                 155                 160

Ser Thr Ser Gly Gly Thr Ala Ala Leu Gly Cys Leu Val Lys Asp Tyr
                165                 170                 175

Phe Pro Glu Pro Val Thr Val Ser Trp Asn Ser Gly Ala Leu Thr Ser
            180                 185                 190

Gly Val His Thr Phe Pro Ala Val Leu Gln Ser Ser Gly Leu Tyr Ser
        195                 200                 205

Leu Ser Ser Val Val Thr Val Pro Ser Ser Ser Leu Gly Thr Gln Thr
    210                 215                 220

Tyr Ile Cys Asn Val Asn His Lys Pro Ser Asn Thr Lys Val Asp Lys
225                 230                 235                 240

Arg Val Glu Pro Lys Ser Cys Asp Lys Thr His Thr Cys Pro Pro Cys
                245                 250                 255

Pro Ala Pro Glu Leu Leu Gly Gly Pro Ser Val Phe Leu Phe Pro Pro
            260                 265                 270

Asn Pro Arg Thr Pro Ser Ser
        275

<210> SEQ ID NO 39
<211> LENGTH: 275
<212> TYPE: PRT
<213> ORGANISM: Artificial Sequence
<220> FEATURE:
<223> OTHER INFORMATION: HC variable region

<400> SEQUENCE: 39

Met Glu Thr Asp Thr Leu Leu Leu Trp Val Leu Leu Trp Val Pro
1               5                   10                  15

Gly Ser Thr Gly Asp Glu Val Gln Leu Val Gln Ser Gly Ala Glu Val
                20                  25                  30

Lys Lys Pro Gly Ala Ser Val Lys Val Ser Cys Lys Ala Ser Gly Tyr
            35                  40                  45

Thr Phe Thr Lys Tyr Gly Ile Ser Trp Val Arg Gln Ala Pro Gly Gln
```

```
            50                  55                  60
Gly Leu Glu Trp Met Gly Trp Ile Ser Ala Phe Asn Gly Tyr Thr Arg
 65                  70                  75                  80

Tyr Gly Gln Arg Phe Gln Gly Lys Val Thr Met Thr Thr Asp Thr Ser
                 85                  90                  95

Thr Asn Thr Ala Ser Leu Glu Val Arg Thr Leu Thr Ser Asn Asp Thr
            100                 105                 110

Ala Val Tyr Tyr Cys Ala Arg Gln Tyr Pro Asp Gln Tyr Ser Ser Ser
        115                 120                 125

Gly Trp Pro Arg Leu Phe Ala Met Asp Val Trp Gly Gln Gly Thr Thr
    130                 135                 140

Val Ile Val Ser Pro Ala Ser Thr Lys Gly Pro Ser Val Phe Pro Leu
145                 150                 155                 160

Ala Pro Ser Ser Lys Ser Thr Ser Gly Gly Thr Ala Ala Leu Gly Cys
                165                 170                 175

Leu Val Lys Asp Tyr Phe Pro Glu Pro Val Thr Val Ser Trp Asn Ser
            180                 185                 190

Gly Ala Leu Thr Ser Gly Val His Thr Phe Pro Ala Val Leu Gln Ser
        195                 200                 205

Ser Gly Leu Tyr Ser Leu Ser Ser Val Val Thr Val Pro Ser Ser Ser
    210                 215                 220

Leu Gly Thr Gln Thr Tyr Ile Cys Asn Val Asn His Lys Pro Ser Asn
225                 230                 235                 240

Thr Lys Val Asp Lys Arg Val Glu Pro Lys Ser Cys Asp Lys Thr His
                245                 250                 255

Thr Cys Pro Pro Cys Pro Ala Pro Glu Leu Leu Gly Gly Pro Ser Val
            260                 265                 270

Phe Leu Phe
        275

<210> SEQ ID NO 40
<211> LENGTH: 309
<212> TYPE: PRT
<213> ORGANISM: Artificial Sequence
<220> FEATURE:
<223> OTHER INFORMATION: HC variable region

<400> SEQUENCE: 40

Met Glu Thr Asp Thr Leu Leu Leu Trp Val Leu Leu Leu Trp Val Pro
 1               5                  10                  15

Gly Ser Thr Gly Asp Glu Val Gln Leu Val Glu Ser Gly Gly Gly Leu
                20                  25                  30

Val Lys Pro Gly Gly Ser Arg Arg Leu Ser Cys Ala Ala Ser Gly Phe
            35                  40                  45

Thr Phe Ser Arg Asp Thr Met Thr Trp Val Arg Gln Ala Pro Gly Lys
        50                  55                  60

Gly Leu Glu Trp Val Ala Ser Ile Ser Ser Gly Ser Asp Ile Asn
 65                  70                  75                  80

Tyr Ala Asp Ser Val Lys Gly Arg Phe Thr Ile Ser Arg Asp Asn Gly
                 85                  90                  95

Lys Asn Ser Leu Tyr Leu His Met Asn Ser Leu Arg Ala Asp Asp Thr
            100                 105                 110

Ala Ile Tyr Tyr Cys Ala Arg Asp Pro Arg Ser Gly Ile Ser Gly Arg
        115                 120                 125

Tyr Gly Met Asp Val Trp Gly Gln Gly Thr Thr Val Thr Val Ser Ser
```

Ala Ser Thr Lys Gly Pro Ser Val Phe Pro Leu Ala Pro Ser Ser Lys
145                 150                 155                 160

Ser Thr Ser Gly Gly Thr Ala Ala Leu Gly Cys Leu Val Lys Asp Tyr
                165                 170                 175

Phe Pro Glu Pro Val Thr Val Ser Trp Asn Ser Gly Ala Leu Thr Ser
            180                 185                 190

Gly Val His Thr Phe Pro Ala Val Leu Gln Ser Ser Gly Leu Tyr Ser
        195                 200                 205

Leu Ser Ser Val Val Thr Val Pro Ser Ser Ser Leu Gly Thr Gln Thr
    210                 215                 220

Tyr Ile Cys Asn Val Asn His Lys Pro Ser Asn Thr Lys Val Asp Lys
225                 230                 235                 240

Arg Val Glu Pro Lys Ser Cys Asp Lys Thr His Thr Cys Pro Pro Cys
                245                 250                 255

Pro Ala Pro Glu Leu Leu Gly Gly Pro Ser Val Phe Leu Phe Pro Pro
            260                 265                 270

Lys Pro Lys Asp Thr Leu Met Ile Ser Arg Thr Pro Glu Val Thr Cys
        275                 280                 285

Val Val Val Asp Val Ser His Glu Asp Pro Glu Val Lys Phe Asn Trp
    290                 295                 300

Tyr Val Asp Gly Val
305

<210> SEQ ID NO 41
<211> LENGTH: 296
<212> TYPE: PRT
<213> ORGANISM: Artificial Sequence
<220> FEATURE:
<223> OTHER INFORMATION: HC variable region

<400> SEQUENCE: 41

Met Glu Thr Asp Thr Leu Leu Leu Trp Val Leu Leu Leu Trp Val Pro
1               5                   10                  15

Gly Ser Thr Gly Asp Glu Val Gln Leu Val Gln Ser Gly Gly Gly Leu
                20                  25                  30

Val Lys Ala Gly Gly Ser Leu Arg Leu Ser Cys Ala Ala Ser Gly Phe
            35                  40                  45

Thr Phe Ser Thr Tyr Ser Met Asn Trp Ile Arg Gln Ala Pro Gly Lys
        50                  55                  60

Gly Leu Glu Trp Val Ala Ser Ile Ser Ser Arg Ser Gly Ser His Ile
65                  70                  75                  80

Asn Tyr Val Asp Ser Val Lys Gly Arg Phe Thr Ile Ser Arg Asp Asn
                85                  90                  95

Ala Arg Asp Leu Leu Tyr Leu Gln Met Asn Ser Leu Arg Val Asp Asp
            100                 105                 110

Ser Ala Leu Tyr Tyr Cys Ala Arg Asp Arg Ser Gly Thr Ser Pro
        115                 120                 125

Leu Pro Leu Asp Val Trp Gly Gln Gly Thr Thr Val Thr Val Phe Ser
    130                 135                 140

Ala Ser Thr Lys Gly Pro Ser Val Phe Pro Leu Ala Pro Ser Ser Lys
145                 150                 155                 160

Ser Thr Ser Gly Gly Thr Ala Ala Leu Gly Cys Leu Val Lys Asp Tyr
                165                 170                 175

Phe Pro Glu Pro Val Thr Val Ser Trp Asn Ser Gly Ala Leu Thr Ser

```
                    180                 185                 190
Gly Val His Thr Phe Pro Ala Val Leu Gln Ser Ser Gly Leu Tyr Ser
                195                 200                 205

Leu Ser Ser Val Val Thr Val Pro Ser Ser Ser Leu Gly Thr Gln Thr
            210                 215                 220

Tyr Ile Cys Asn Val Asn His Lys Pro Ser Asn Thr Lys Val Asp Lys
225                 230                 235                 240

Arg Val Glu Pro Lys Ser Cys Asp Lys Thr His Thr Cys Pro Pro Cys
                245                 250                 255

Pro Ala Pro Glu Leu Leu Gly Gly Pro Ser Val Phe Leu Phe Pro Pro
            260                 265                 270

Lys Pro Lys Asp Thr Leu Met Ile Ser Arg Thr Pro Glu Val Thr Cys
            275                 280                 285

Val Val Val Asp Val Ser His Glu
            290                 295

<210> SEQ ID NO 42
<211> LENGTH: 295
<212> TYPE: PRT
<213> ORGANISM: Artificial Sequence
<220> FEATURE:
<223> OTHER INFORMATION: HC variable region
<221> NAME/KEY: VARIANT
<222> LOCATION: 295
<223> OTHER INFORMATION: Xaa = unknown amino acid

<400> SEQUENCE: 42

Met Glu Thr Asp Thr Leu Leu Leu Trp Val Leu Leu Leu Trp Val Pro
1               5                   10                  15

Gly Ser Thr Gly Asp Gln Gly Thr Leu Arg Glu Ser Gly Pro Gly Leu
                20                  25                  30

Val Arg Pro Ser Glu Thr Leu Ser Leu Thr Cys Gly Val Ser Gly Tyr
            35                  40                  45

Ser Ile Ser Ser Gly Tyr Tyr Trp Gly Trp Ile Arg Gln Pro Pro Gly
    50                  55                  60

Lys Gly Leu Glu Trp Ile Gly Asn Ile Tyr Arg Ser Gly Ser Thr Tyr
65                  70                  75                  80

Tyr Asn Pro Ser Leu Lys Ser Arg Val Thr Val Ser Ile Asp Thr Ser
                85                  90                  95

Lys Asn Gln Phe Ser Leu Lys Leu Asn Ser Val Thr Ala Ala Asp Thr
            100                 105                 110

Ala Val Tyr Tyr Cys Ala Arg Ser Gly Ile Lys Val Ala Asp Asp Tyr
            115                 120                 125

Tyr Tyr Glu Met Asp Val Trp Gly Gln Gly Thr Asp Asp Tyr Ser Tyr
            130                 135                 140

Ala Met Asp Val Trp Gly Gln Gly Thr Thr Val Thr Val Ser Ser Ala
145                 150                 155                 160

Ser Thr Lys Gly Pro Ser Val Phe Pro Leu Ala Pro Ser Ser Lys Ser
                165                 170                 175

Thr Ser Gly Gly Thr Ala Ala Leu Gly Cys Leu Val Lys Asp Tyr Phe
            180                 185                 190

Pro Glu Pro Val Thr Val Ser Trp Asn Ser Gly Ala Leu Thr Ser Gly
            195                 200                 205

Val His Thr Phe Pro Ala Val Leu Gln Ser Ser Gly Leu Tyr Ser Leu
            210                 215                 220

Ser Ser Val Val Thr Val Pro Ser Ser Ser Leu Gly Thr Gln Thr Tyr
```

```
            225                 230                 235                 240

Ile Cys Asn Val Asn His Lys Pro Ser Asn Thr Lys Val Asp Lys Arg
                245                 250                 255

Val Glu Pro Lys Ser Cys Asp Lys Thr His Thr Cys Pro Pro Cys Pro
                260                 265                 270

Ala Pro Glu Leu Leu Gly Gly Pro Ser Val Phe Leu Phe Pro Pro Lys
                275                 280                 285

Pro Lys Asp Thr Leu Met Xaa
                290                 295

<210> SEQ ID NO 43
<211> LENGTH: 283
<212> TYPE: PRT
<213> ORGANISM: Artificial Sequence
<220> FEATURE:
<223> OTHER INFORMATION: HC variable region

<400> SEQUENCE: 43

Met Glu Thr Asp Thr Leu Leu Leu Trp Val Leu Leu Leu Trp Val Pro
1               5                   10                  15

Gly Ser Thr Gly Asp Glu Val Gln Leu Val Glu Ser Gly Gly Gly Leu
                20                  25                  30

Val Lys Pro Gly Gly Ser Leu Arg Leu Ser Cys Val Ala Ser Gly Phe
            35                  40                  45

Thr Phe Ser Ser Tyr Ser Met Asn Trp Val Arg Gln Ala Pro Gly Lys
        50                  55                  60

Gly Leu Glu Trp Val Ser Ser Ile Ser Ser Gly Ser Ser Tyr Ile Glu
65                  70                  75                  80

Tyr Ala Asp Ser Val Lys Gly Arg Leu Thr Ile Ser Arg Asp Asn Ala
                85                  90                  95

Lys Lys Ser Leu Tyr Leu Gln Leu Asn Ser Leu Arg Ala Glu Asp Thr
            100                 105                 110

Ala Val Tyr Tyr Cys Ala Arg His Thr Ala Arg Ile Asp Ser Tyr His
        115                 120                 125

Gly Met Asp Val Trp Gly Gln Gly Thr Thr Val Thr Val Ser Ser Ala
130                 135                 140

Ser Thr Lys Gly Pro Ser Val Phe Pro Leu Ala Pro Ser Ser Lys Ser
145                 150                 155                 160

Thr Ser Gly Gly Thr Ala Ala Leu Gly Cys Leu Val Lys Asp Tyr Phe
                165                 170                 175

Pro Glu Pro Val Thr Val Ser Trp Asn Ser Gly Ala Leu Thr Ser Gly
            180                 185                 190

Val His Thr Phe Pro Ala Val Leu Gln Ser Ser Gly Leu Tyr Ser Leu
        195                 200                 205

Ser Ser Val Val Thr Val Pro Ser Ser Ser Leu Gly Thr Gln Thr Tyr
    210                 215                 220

Ile Cys Asn Val Asn His Lys Pro Ser Asn Thr Lys Val Asp Lys Arg
225                 230                 235                 240

Val Glu Pro Lys Ser Cys Asp Lys Thr His Thr Cys Pro Pro Cys Pro
                245                 250                 255

Ala Pro Glu Leu Leu Gly Gly Pro Ser Val Phe Leu Phe Pro Pro Lys
            260                 265                 270

Pro Lys Asp Thr Leu Met Ile Ser Arg Thr Pro
        275                 280
```

<210> SEQ ID NO 44
<211> LENGTH: 295
<212> TYPE: PRT
<213> ORGANISM: Artificial Sequence
<220> FEATURE:
<223> OTHER INFORMATION: HC variable region
<221> NAME/KEY: VARIANT
<222> LOCATION: 271
<223> OTHER INFORMATION: Xaa = unknown amino acid

<400> SEQUENCE: 44

```
Met Glu Thr Asp Thr Leu Leu Leu Trp Val Leu Leu Leu Trp Val Pro
1               5                   10                  15

Gly Ser Thr Gly Asp Gln Val Gln Leu Gln Glu Ser Gly Ala Gly Leu
            20                  25                  30

Leu Lys Pro Ser Glu Thr Leu Ser Leu Ser Cys Thr Val Asp Gly Glu
        35                  40                  45

Ser Phe Asn Gly Phe Phe Trp Thr Trp Ile Arg Gln Pro Pro Gly Lys
    50                  55                  60

Gly Leu Glu Trp Ile Gly Glu Ile Asn His Leu Ala Ser Thr Gly Tyr
65                  70                  75                  80

Asn Pro Ser Leu Lys Ser Arg Val Thr Ile Ser Val Asp Thr Ser Lys
                85                  90                  95

Asn Gln Phe Ser Leu Lys Leu Thr Ser Val Thr Ala Ala Asp Thr Ala
            100                 105                 110

Val Tyr Tyr Cys Ala Arg Gly Tyr Ser Tyr Gly Phe Ala Trp Pro Asn
        115                 120                 125

Tyr His Tyr Leu Asp Val Trp Gly Lys Gly Thr Thr Val Thr Val Ser
    130                 135                 140

Ser Ala Ser Thr Lys Gly Pro Ser Val Phe Pro Leu Ala Pro Ser Ser
145                 150                 155                 160

Lys Ser Thr Ser Gly Gly Thr Ala Ala Leu Gly Cys Leu Val Lys Asp
                165                 170                 175

Tyr Phe Pro Glu Pro Val Thr Val Ser Trp Asn Ser Gly Ala Leu Thr
            180                 185                 190

Ser Gly Val His Thr Phe Pro Ala Val Leu Gln Ser Ser Gly Leu Tyr
        195                 200                 205

Ser Leu Ser Ser Val Val Thr Val Pro Ser Ser Ser Leu Gly Thr Gln
    210                 215                 220

Thr Tyr Ile Cys Asn Val Asn His Lys Pro Ser Asn Thr Lys Val Asp
225                 230                 235                 240

Lys Arg Val Glu Pro Lys Ser Cys Asp Lys Thr His Thr Cys Pro Pro
                245                 250                 255

Cys Pro Ala Pro Glu Leu Leu Gly Gly Pro Ser Val Phe Leu Xaa Pro
            260                 265                 270

Pro Lys Pro Lys Asp Thr Leu Met Ile Ser Arg Thr Pro Glu Val Thr
        275                 280                 285

Cys Val Val Val Asp Val Ser
    290                 295
```

<210> SEQ ID NO 45
<211> LENGTH: 283
<212> TYPE: PRT
<213> ORGANISM: Artificial Sequence
<220> FEATURE:
<223> OTHER INFORMATION: HC variable region

<400> SEQUENCE: 45

```
Met Glu Thr Asp Thr Leu Leu Leu Trp Val Leu Leu Leu Trp Val Pro
1               5                   10                  15

Gly Ser Thr Gly Asp Glu Val Gln Leu Val Gln Ser Gly Gly Arg Leu
            20                  25                  30

Val Gln Pro Gly Gly Ser Leu Arg Leu Ser Cys Val Ala Ser Gly Phe
        35                  40                  45

Thr Phe Ser Ser His Ala Met Ser Trp Val Arg Gln Ala Pro Gly Lys
    50                  55                  60

Gly Leu Glu Trp Val Ser Gly Phe Ser Gly Ser Gly Thr Thr Lys
65                  70                  75                  80

Tyr Ala Asp Ser Val Lys Gly Arg Phe Thr Ile Ser Arg Asp Asn Ser
                85                  90                  95

Lys Lys Thr Leu Tyr Leu Gln Met Asn Ser Leu Arg Ala Glu Asp Thr
            100                 105                 110

Ala Val Tyr Tyr Cys Ala Lys Gly Phe Ser Pro Phe Arg Gly Val Gln
        115                 120                 125

Phe Pro Tyr Phe Asp Tyr Trp Gly Gln Gly Thr Leu Val Thr Val Ser
    130                 135                 140

Ser Ala Ser Thr Lys Gly Pro Ser Val Phe Pro Leu Ala Pro Ser Ser
145                 150                 155                 160

Lys Ser Thr Ser Gly Gly Thr Ala Ala Leu Gly Cys Leu Val Lys Asp
                165                 170                 175

Tyr Phe Pro Glu Pro Val Thr Val Ser Trp Asn Ser Gly Ala Leu Thr
            180                 185                 190

Ser Gly Val His Thr Phe Pro Ala Val Leu Gln Ser Ser Gly Leu Tyr
        195                 200                 205

Ser Leu Ser Ser Val Val Thr Val Pro Ser Ser Ser Leu Gly Thr Gln
    210                 215                 220

Thr Tyr Ile Cys Asn Val Asn His Lys Pro Ser Asn Thr Lys Val Asp
225                 230                 235                 240

Lys Arg Val Glu Pro Lys Ser Cys Asp Lys Thr His Thr Cys Pro Pro
                245                 250                 255

Cys Pro Ala Pro Glu Leu Leu Gly Gly Pro Ser Val Phe Leu Phe Pro
            260                 265                 270

Pro Lys Pro Arg Thr Pro Ser Ser Pro Gly Pro
        275                 280

<210> SEQ ID NO 46
<211> LENGTH: 287
<212> TYPE: PRT
<213> ORGANISM: Artificial Sequence
<220> FEATURE:
<223> OTHER INFORMATION: HC variable region

<400> SEQUENCE: 46

Met Glu Thr Asp Thr Leu Leu Leu Trp Val Leu Leu Leu Trp Val Pro
1               5                   10                  15

Gly Ser Thr Gly Asp Glu Val Gln Leu Val Glu Ser Gly Gly Gly Leu
            20                  25                  30

Val Arg Pro Gly Gly Ser Leu Arg Leu Ser Cys Ala Ala Ala Gly Phe
        35                  40                  45

Thr Phe Lys Ser Tyr Ser Met Asn Trp Val Arg Gln Ala Pro Gly Arg
    50                  55                  60

Gly Leu Glu Trp Val Ser Ser Ile Thr Ser Gly Gly Ser Lys Thr Tyr
65                  70                  75                  80
```

```
Tyr Ala Asp Val Val Lys Gly Arg Phe Thr Val Ser Arg Asp Asn Ala
                85                  90                  95

Lys Gln Ser Leu Tyr Leu Gln Met Asn Ser Leu Arg Ala Glu Asp Thr
            100                 105                 110

Ala Ile Tyr Phe Cys Ala Arg Ser Leu His Ser Thr Ser Gln Pro Ser
        115                 120                 125

Tyr Met Asp Val Trp Gly Arg Lys Ile Thr Val Ile Val Ser Ser Ala
    130                 135                 140

Ser Thr Lys Gly Pro Ser Val Phe Pro Leu Ala Pro Ser Ser Lys Ser
145                 150                 155                 160

Thr Ser Gly Gly Thr Ala Ala Leu Gly Cys Leu Val Lys Asp Tyr Phe
                165                 170                 175

Pro Glu Pro Val Thr Val Ser Trp Asn Ser Gly Ala Leu Thr Ser Gly
            180                 185                 190

Val His Thr Phe Pro Ala Val Leu Gln Ser Ser Gly Leu Tyr Ser Leu
        195                 200                 205

Ser Ser Val Val Thr Val Pro Ser Ser Ser Leu Gly Thr Gln Thr Tyr
    210                 215                 220

Ile Cys Asn Val Asn His Lys Pro Ser Asn Thr Lys Val Asp Lys Arg
225                 230                 235                 240

Val Glu Pro Lys Ser Cys Asp Lys Thr His Thr Cys Pro Pro Cys Pro
                245                 250                 255

Ala Pro Glu Leu Leu Gly Gly Pro Ser Val Phe Leu Phe Pro Pro Lys
            260                 265                 270

Pro Lys Asp Thr Leu Met Ile Ser Arg Thr Pro Glu Val Thr Cys
        275                 280                 285

<210> SEQ ID NO 47
<211> LENGTH: 290
<212> TYPE: PRT
<213> ORGANISM: Artificial Sequence
<220> FEATURE:
<223> OTHER INFORMATION: HC variable region

<400> SEQUENCE: 47

Met Glu Thr Asp Thr Leu Leu Leu Trp Val Leu Leu Leu Trp Val Pro
1               5                   10                  15

Gly Ser Thr Gly Asp Gln Val Gln Leu Gln Glu Ser Gly Pro Gly Leu
            20                  25                  30

Val Lys Pro Ser Glu Thr Leu Ser Leu Thr Cys Ser Ile Ser Gly Val
        35                  40                  45

Ser Thr Arg Asn Tyr Tyr Trp Ser Trp Ile Arg Gln Ser Pro Gly Lys
    50                  55                  60

Gly Leu Glu Trp Ile Gly Tyr Ile Phe Asn Ile Gly Thr Thr Asn Tyr
65                  70                  75                  80

Asn Pro Ser Leu Lys Ser Arg Leu Thr Ile Ser Val Asp Thr Ser Lys
                85                  90                  95

Asn Gln Phe Ser Leu Lys Ile Thr Ser Val Thr Ala Ala Asp Thr Ala
            100                 105                 110

Val Tyr Tyr Cys Ala Ser Gly Phe Glu Tyr Gly Asp Tyr Thr Phe Asp
        115                 120                 125

Tyr Trp Gly Gln Gly Thr Pro Val Thr Val Ser Ser Ala Ser Thr Lys
    130                 135                 140

Gly Pro Ser Val Phe Pro Leu Ala Pro Ser Ser Lys Ser Thr Ser Gly
145                 150                 155                 160
```

```
Gly Thr Ala Ala Leu Gly Cys Leu Val Lys Asp Tyr Phe Pro Glu Pro
            165                 170                 175

Val Thr Val Ser Trp Asn Ser Gly Ala Leu Thr Ser Gly Val His Thr
        180                 185                 190

Phe Pro Ala Val Leu Gln Ser Ser Gly Leu Tyr Ser Leu Ser Ser Val
            195                 200                 205

Val Thr Val Pro Ser Ser Leu Gly Thr Gln Thr Tyr Ile Cys Asn
        210                 215                 220

Val Asn His Lys Pro Ser Asn Thr Lys Val Asp Lys Arg Val Glu Pro
225                 230                 235                 240

Lys Ser Cys Asp Lys Thr His Thr Cys Pro Pro Cys Pro Ala Pro Glu
                245                 250                 255

Leu Leu Gly Gly Pro Ser Val Phe Leu Phe Pro Pro Lys Pro Lys Asp
            260                 265                 270

Thr Leu Met Ile Phe Arg Thr Pro Glu Val Thr Cys Val Val Val Asp
        275                 280                 285

Val Ser
    290

<210> SEQ ID NO 48
<211> LENGTH: 276
<212> TYPE: PRT
<213> ORGANISM: Artificial Sequence
<220> FEATURE:
<223> OTHER INFORMATION: HC variable region

<400> SEQUENCE: 48

Met Glu Thr Asp Thr Leu Leu Leu Trp Val Leu Leu Leu Trp Val Pro
1               5                   10                  15

Gly Ser Thr Gly Asp Gln Val Gln Leu Gln Glu Ser Gly Gly Gly Leu
            20                  25                  30

Val Lys Pro Gly Gly Ser Leu Arg Leu Ser Cys Thr Ala Ser Gly Phe
        35                  40                  45

Asn Phe Asn Lys Tyr Asn Met Asn Trp Val Arg Gln Ala Pro Gly Lys
    50                  55                  60

Gly Leu Glu Trp Val Ser Ser Ile Ser Ala Leu Ser Tyr Ile Tyr
65                  70                  75                  80

Tyr Ala Asp Ser Leu Lys Gly Arg Phe Thr Val Ser Arg Asp Asn Ala
                85                  90                  95

Lys Asn Ser Leu Phe Leu Gln Met Asn Ser Leu Arg Asp Asp Asp Thr
            100                 105                 110

Ala Val Tyr Tyr Cys Ala Arg Glu Ile Arg Arg Ala Ser Thr Trp Ser
        115                 120                 125

Ala Asp Leu Trp Gly Arg Gly Thr Leu Val Thr Val Ser Ser Ala Ser
    130                 135                 140

Thr Lys Gly Pro Ser Val Phe Pro Leu Ala Pro Ser Ser Lys Ser Thr
145                 150                 155                 160

Ser Gly Gly Thr Ala Ala Leu Gly Cys Leu Val Lys Asp Tyr Phe Pro
                165                 170                 175

Glu Pro Val Thr Val Ser Trp Asn Ser Gly Ala Leu Thr Ser Gly Val
            180                 185                 190

His Thr Phe Pro Ala Val Leu Gln Ser Ser Gly Leu Tyr Ser Leu Ser
        195                 200                 205

Ser Val Val Thr Val Pro Ser Ser Leu Gly Thr Gln Thr Tyr Ile
    210                 215                 220
```

```
Cys Asn Val Asn His Lys Pro Ser Asn Thr Lys Val Asp Lys Arg Val
225                 230                 235                 240

Glu Pro Lys Ser Cys Asp Lys Thr His Thr Cys Pro Pro Cys Pro Ala
            245                 250                 255

Pro Glu Leu Leu Gly Gly Pro Ser Val Phe Leu Phe Pro Pro Asn Pro
        260                 265                 270

Arg Thr Pro Ser
        275
```

<210> SEQ ID NO 49
<211> LENGTH: 225
<212> TYPE: PRT
<213> ORGANISM: Artificial Sequence
<220> FEATURE:
<223> OTHER INFORMATION: LC variable region

<400> SEQUENCE: 49

```
Met Glu Thr Asp Thr Leu Leu Leu Trp Val Leu Leu Leu Trp Val Pro
1               5                   10                  15

Gly Ser Thr Gly Asp Glu Ile Val Leu Thr Gln Ser Pro Ser Ser Leu
            20                  25                  30

Ser Ala Ser Val Gly Asp Arg Val Thr Ile Thr Cys Arg Ala Ser Arg
        35                  40                  45

Asp Ile Asn Thr Tyr Leu Gly Trp Phe Gln Gln Arg Pro Gly Lys Ala
    50                  55                  60

Pro Lys Ser Leu Ile Tyr Gly Ala Ser Asn Leu Gln Asn Gly Val Pro
65                  70                  75                  80

Ser Arg Phe Ser Gly Ser Gly Ser Gly Thr Tyr Phe Thr Leu Thr Ile
                85                  90                  95

Asn Gly Leu Gln Thr Glu Asp Phe Ala Thr Tyr Tyr Cys Gln Gln Tyr
            100                 105                 110

Ser Ile Tyr Pro Leu Ser Leu Gly Gly Gly Thr Lys Ala Asp Met Lys
        115                 120                 125

Arg Thr Val Ala Ala Pro Ser Val Phe Ile Phe Pro Pro Ser Asp Glu
    130                 135                 140

Gln Leu Lys Ser Gly Thr Ala Ser Val Val Cys Leu Leu Asn Asn Phe
145                 150                 155                 160

Tyr Pro Arg Glu Ala Lys Val Gln Trp Lys Val Asp Asn Ala Leu Gln
                165                 170                 175

Ser Gly Asn Ser Gln Glu Ser Val Thr Glu Gln Asp Ser Lys Asp Ser
            180                 185                 190

Thr Tyr Ser Leu Ser Ser Thr Leu Thr Leu Ser Lys Ala Asp Tyr Glu
        195                 200                 205

Lys His Lys Val Tyr Ala Cys Glu Val Thr His Gln Gly Leu Ser Ser
    210                 215                 220

Pro
225
```

<210> SEQ ID NO 50
<211> LENGTH: 235
<212> TYPE: PRT
<213> ORGANISM: Artificial Sequence
<220> FEATURE:
<223> OTHER INFORMATION: LC variable region

<400> SEQUENCE: 50

```
Met Glu Thr Asp Thr Leu Leu Leu Trp Leu Leu Leu Leu Trp Val Pro
1               5                   10                  15
```

-continued

Gly Ser Thr Gly Asp Glu Ile Val Leu Thr Gln Ser Pro Ser Thr Leu
            20                  25                  30

Ser Ala Ser Val Gly Asp Arg Val Thr Ile Thr Cys Arg Ala Ser Gln
        35                  40                  45

Ser Ile Asn Asn Trp Leu Ala Trp Tyr Gln Lys Pro Gly Lys Ala
    50                  55                  60

Pro Lys Leu Leu Ile Asn Lys Ala Ser Ser Leu Glu Ser Gly Val Pro
65              70                  75                  80

Ser Arg Phe Ser Gly Ser Gly Ser Gly Thr Glu Phe Thr Leu Thr Ile
                85                  90                  95

Thr Ser Leu Gln Pro Asp Asp Phe Ala Thr Tyr Tyr Cys Gln Gln Tyr
            100                 105                 110

Asn Ser Asn Ser Trp Thr Phe Gly Gln Gly Thr Lys Val Asp Met Lys
        115                 120                 125

Arg Thr Val Ala Ala Pro Ser Val Phe Ile Phe Pro Pro Ser Asp Glu
    130                 135                 140

Gln Leu Lys Ser Gly Thr Ala Ser Val Val Cys Leu Leu Asn Asn Phe
145                 150                 155                 160

Tyr Pro Arg Glu Ala Lys Val Gln Trp Lys Val Asp Asn Ala Leu Gln
                165                 170                 175

Ser Gly Asn Ser Gln Glu Ser Val Thr Glu Gln Asp Ser Lys Asp Ser
            180                 185                 190

Thr Tyr Ser Leu Ser Ser Thr Leu Thr Leu Ser Lys Ala Asp Tyr Glu
        195                 200                 205

Lys His Lys Val Tyr Ala Cys Glu Val Thr His Gln Gly Leu Ser Ser
    210                 215                 220

Pro Val Thr Lys Ser Phe Asn Arg Gly Glu Cys
225                 230                 235

<210> SEQ ID NO 51
<211> LENGTH: 241
<212> TYPE: PRT
<213> ORGANISM: Artificial Sequence
<220> FEATURE:
<223> OTHER INFORMATION: LC variable region

<400> SEQUENCE: 51

Met Lys Thr Asp Thr Leu Leu Leu Trp Val Leu Leu Leu Trp Val Pro
1               5                   10                  15

Gly Ser Thr Gly Asp Asp Ile Val Leu Thr Gln Ser Pro Asp Ser Leu
            20                  25                  30

Ala Val Ser Leu Gly Glu Arg Ala Thr Ile Asn Cys Lys Ser Ser Gln
        35                  40                  45

Ser Val Leu Tyr Ser Ser Asn Asn Lys Asn Tyr Leu Ala Trp Tyr Gln
    50                  55                  60

Gln Lys Pro Gly Gln Pro Pro Lys Leu Leu Ile Tyr Trp Ala Ser Thr
65              70                  75                  80

Arg Glu Ser Gly Val Pro Asp Arg Phe Ser Gly Ser Gly Ser Gly Thr
                85                  90                  95

Asp Phe Thr Leu Thr Ile Ser Ser Leu Gln Ala Glu Asp Val Ala Val
            100                 105                 110

Tyr Tyr Cys Gln Gln Tyr Tyr Ser Thr Pro Pro Thr Phe Gly Gln Gly
        115                 120                 125

Thr Lys Val Glu Ile Lys Arg Thr Val Ala Ala Pro Ser Val Phe Ile
    130                 135                 140

Phe Pro Pro Ser Asp Glu Gln Leu Lys Ser Gly Thr Ala Ser Val Val
145                 150                 155                 160

Cys Leu Leu Asn Asn Phe Tyr Pro Arg Glu Ala Lys Val Gln Trp Lys
                165                 170                 175

Val Asp Asn Ala Leu Gln Ser Gly Asn Ser Gln Glu Ser Val Thr Glu
            180                 185                 190

Gln Asp Ser Lys Asp Ser Thr Tyr Ser Leu Ser Ser Thr Leu Thr Leu
            195                 200                 205

Ser Lys Ala Asp Tyr Glu Lys His Lys Val Tyr Ala Cys Glu Val Thr
    210                 215                 220

His Gln Gly Leu Ser Ser Pro Val Thr Lys Ser Phe Asn Arg Gly Glu
225                 230                 235                 240

Cys

<210> SEQ ID NO 52
<211> LENGTH: 237
<212> TYPE: PRT
<213> ORGANISM: Artificial Sequence
<220> FEATURE:
<223> OTHER INFORMATION: LC variable region

<400> SEQUENCE: 52

Met Glu Thr Asp Thr Leu Leu Leu Trp Val Leu Leu Leu Trp Val Pro
1               5                   10                  15

Gly Ser Thr Gly Asp Leu Pro Val Leu Thr Gln Pro Ala Ser Val Ser
            20                  25                  30

Gly Ser Pro Gly Gln Ser Ile Thr Ile Ser Cys Thr Gly Thr Ser Ser
        35                  40                  45

Asp Val Gly Ala Tyr Asn Tyr Val Ser Trp Tyr Gln Gln His Pro Gly
    50                  55                  60

Lys Ala Pro Lys Leu Ile Ile Tyr Glu Val Lys Ile Arg Pro Ser Gly
65                  70                  75                  80

Val Ser Asn Arg Phe Ser Gly Ser Lys Ser Gly Asn Thr Ala Ser Leu
                85                  90                  95

Thr Ile Ser Gly Leu Gln Ala Glu Asp Glu Ala Asp Tyr Phe Cys Ser
            100                 105                 110

Ser Tyr Ser Thr Asn Ser Pro Trp Val Phe Gly Gly Gly Thr Lys Val
        115                 120                 125

Thr Val Leu Arg Gln Pro Lys Ala Ala Pro Ser Val Thr Leu Phe Pro
130                 135                 140

Pro Ser Ser Glu Glu Leu Gln Ala Asn Lys Ala Thr Leu Val Cys Leu
145                 150                 155                 160

Ile Ser Asp Phe Tyr Pro Gly Ala Val Thr Val Ala Trp Lys Ala Asp
                165                 170                 175

Ser Ser Pro Val Lys Ala Gly Val Glu Thr Thr Thr Pro Ser Lys Gln
            180                 185                 190

Ser Asn Asn Lys Tyr Ala Ala Ser Ser Tyr Leu Ser Leu Thr Pro Glu
        195                 200                 205

Gln Trp Lys Ser His Arg Ser Tyr Ser Cys Gln Val Thr His Glu Gly
    210                 215                 220

Ser Thr Val Glu Lys Thr Val Ala Pro Thr Glu Cys Ser
225                 230                 235

<210> SEQ ID NO 53
<211> LENGTH: 237

<212> TYPE: PRT
<213> ORGANISM: Artificial Sequence
<220> FEATURE:
<223> OTHER INFORMATION: LC variable region

<400> SEQUENCE: 53

Met Glu Thr Asp Thr Leu Leu Leu Trp Val Leu Leu Trp Val Pro
1               5                   10                  15

Gly Ser Thr Gly Asp Glu Ile Val Leu Thr Gln Ser Pro Gly Thr Leu
            20                  25                  30

Ser Leu Ser Pro Gly Glu Arg Ala Thr Leu Ser Cys Arg Ala Ser Gln
        35                  40                  45

Ser Val Thr Lys Asn Tyr Leu Ala Trp Tyr Gln Gln Lys Pro Gly Gln
    50                  55                  60

Ala Pro Thr Leu Val Ile Tyr Asp Ala Ser Thr Arg Ala Ser Gly Ile
65                  70                  75                  80

Pro Asp Arg Phe Ile Gly Ser Gly Ser Gly Thr Asp Phe Thr Leu Thr
                85                  90                  95

Ile Ser Arg Leu Glu Pro Glu Asp Phe Ala Val Tyr Tyr Cys His Gln
            100                 105                 110

Tyr Gly Ser Ser Pro Pro Tyr Thr Phe Gly Arg Gly Thr Lys Leu Glu
        115                 120                 125

Ile Lys Arg Thr Val Ala Ala Pro Ser Val Phe Ile Phe Pro Pro Ser
130                 135                 140

Asp Glu Gln Leu Lys Ser Gly Thr Ala Ser Val Val Cys Leu Leu Asn
145                 150                 155                 160

Asn Phe Tyr Pro Arg Glu Ala Lys Val Gln Trp Lys Val Asp Asn Ala
                165                 170                 175

Leu Gln Ser Gly Asn Ser Gln Glu Ser Val Thr Glu Gln Asp Ser Lys
            180                 185                 190

Asp Ser Thr Tyr Ser Leu Ser Ser Thr Leu Thr Leu Ser Lys Ala Asp
        195                 200                 205

Tyr Glu Lys His Lys Val Tyr Ala Cys Glu Val Thr His Gln Gly Leu
    210                 215                 220

Ser Ser Pro Val Thr Lys Ser Phe Asn Arg Gly Glu Cys
225                 230                 235

<210> SEQ ID NO 54
<211> LENGTH: 238
<212> TYPE: PRT
<213> ORGANISM: Artificial Sequence
<220> FEATURE:
<223> OTHER INFORMATION: LC variable region

<400> SEQUENCE: 54

Met Glu Thr Asp Thr Leu Leu Leu Trp Val Leu Leu Trp Val Pro
1               5                   10                  15

Gly Ser Thr Gly Asp Asp Ile Val Met Thr Gln Ser Pro Asp Ser Leu
            20                  25                  30

Ala Val Ser Leu Gly Glu Arg Ala Thr Ile Asn Cys Lys Ser Ser Gln
        35                  40                  45

Thr Val Leu Phe Thr Ser Tyr Tyr Val Ala Trp Tyr Gln Gln Lys Pro
    50                  55                  60

Gly Gln Pro Pro Lys Leu Leu Phe Ser Gly Ala Ser Ser Arg Glu Ser
65                  70                  75                  80

Gly Val Pro Asp Arg Phe Ser Ala Gly Gly Ser Gly Thr Asp Phe Tyr
                85                  90                  95

```
Leu Thr Ile Asn Ser Leu Gln Ala Glu Asp Val Ala Asp Tyr Tyr Cys
                100                 105                 110

Gln Gln Tyr His Thr Pro Pro Phe Thr Phe Gly Gly Gly Thr Lys Leu
            115                 120                 125

Glu Ile Arg Arg Thr Val Ala Ala Pro Ser Val Phe Ile Phe Pro Pro
130                 135                 140

Ser Asp Glu Gln Leu Lys Ser Gly Thr Ala Ser Val Val Cys Leu Leu
145                 150                 155                 160

Asn Asn Phe Tyr Pro Arg Glu Ala Lys Val Gln Trp Lys Val Asp Asn
                165                 170                 175

Ala Leu Gln Ser Gly Asn Ser Gln Glu Ser Val Thr Glu Gln Asp Ser
            180                 185                 190

Lys Asp Ser Thr Tyr Ser Leu Ser Ser Thr Leu Thr Leu Ser Lys Ala
        195                 200                 205

Asp Tyr Glu Lys His Lys Val Tyr Ala Cys Glu Val Thr His Gln Gly
210                 215                 220

Leu Ser Ser Pro Val Thr Lys Ser Phe Asn Arg Gly Glu Cys
225                 230                 235

<210> SEQ ID NO 55
<211> LENGTH: 235
<212> TYPE: PRT
<213> ORGANISM: Artificial Sequence
<220> FEATURE:
<223> OTHER INFORMATION: LC variable region

<400> SEQUENCE: 55

Met Glu Thr Asp Thr Leu Leu Leu Trp Val Leu Leu Leu Trp Val Pro
1               5                   10                  15

Gly Ser Thr Gly Asp Glu Thr Thr Leu Thr Gln Ser Pro Ala Thr Leu
            20                  25                  30

Ser Val Ser Pro Gly Glu Thr Ala Thr Leu Ser Cys Arg Ala Ser Gln
        35                  40                  45

Asn Val Ile Asn Asn Leu Ala Trp Tyr Gln Gln Lys Pro Gly Gln Ala
    50                  55                  60

Pro Arg Leu Leu Ile Tyr Gly Ala Ser Thr Arg Ala Thr Gly Ile Pro
65                  70                  75                  80

Ala Arg Phe Ser Gly Ser Gly Ser Gly Thr Glu Phe Thr Leu Thr Ile
                85                  90                  95

Ser Ser Met Gln Ser Glu Asp Phe Ala Val Tyr Tyr Cys Gln Gln Tyr
            100                 105                 110

Asn Asp Trp Pro Arg Ser Phe Gly Gln Gly Thr Arg Leu Asp Ile Arg
        115                 120                 125

Arg Thr Val Ala Ala Pro Ser Val Phe Ile Phe Pro Pro Ser Asp Glu
130                 135                 140

Gln Leu Lys Ser Gly Thr Ala Ser Val Val Cys Leu Leu Asn Asn Phe
145                 150                 155                 160

Tyr Pro Arg Glu Ala Lys Val Gln Trp Lys Val Asp Asn Ala Leu Gln
                165                 170                 175

Ser Gly Asn Ser Gln Glu Ser Val Thr Glu Gln Asp Ser Lys Asp Ser
            180                 185                 190

Thr Tyr Ser Leu Ser Ser Thr Leu Thr Leu Ser Lys Ala Asp Tyr Glu
        195                 200                 205

Lys His Lys Val Tyr Ala Cys Glu Val Thr His Gln Gly Leu Ser Ser
210                 215                 220
```

Pro Val Thr Lys Ser Phe Asn Arg Gly Glu Cys
225                 230             235

<210> SEQ ID NO 56
<211> LENGTH: 237
<212> TYPE: PRT
<213> ORGANISM: Artificial Sequence
<220> FEATURE:
<223> OTHER INFORMATION: LC variable region

<400> SEQUENCE: 56

Met Glu Thr Asp Thr Leu Leu Leu Trp Val Leu Leu Trp Val Pro
1               5                   10                  15

Gly Ser Thr Gly Asp Asp Ile Val Leu Thr Gln Ser Pro Gly Thr Leu
                20                  25                  30

Ser Leu Ser Pro Gly Glu Arg Ala Thr Leu Ser Cys Arg Ala Ser Gln
            35                  40                  45

Ser Val Asn Ser Ile Phe Leu Ala Trp Tyr Gln Gln Lys Pro Gly Gln
        50                  55                  60

Ala Pro Arg Leu Leu Ile Tyr Gly Ala Ser Ser Arg Ala Thr Gly Ile
65                  70                  75                  80

Pro Asp Arg Phe Ser Gly Ser Gly Ser Gly Thr Asp Phe Thr Leu Thr
                85                  90                  95

Ile Ser Arg Leu Glu Pro Glu Asp Phe Ala Val Tyr Tyr Cys Gln Gln
            100                 105                 110

Tyr His Ser Ser Pro Lys Leu Thr Phe Gly Gly Gly Thr Lys Val Glu
        115                 120                 125

Ile Lys Arg Thr Val Ala Ala Pro Ser Val Phe Ile Phe Pro Pro Ser
130                 135                 140

Gly Glu Gln Leu Lys Ser Gly Thr Ala Ser Val Val Cys Leu Leu Asn
145                 150                 155                 160

Asn Phe Tyr Pro Arg Glu Ala Lys Val Gln Trp Lys Val Asp Asn Ala
                165                 170                 175

Leu Gln Ser Gly Asn Ser Gln Glu Ser Val Thr Glu Gln Asp Ser Lys
            180                 185                 190

Asp Ser Thr Tyr Ser Leu Ser Ser Thr Leu Thr Leu Ser Lys Ala Asp
        195                 200                 205

Tyr Glu Lys His Lys Val Tyr Ala Cys Glu Val Thr His Gln Gly Leu
    210                 215                 220

Ser Ser Pro Val Thr Lys Ser Phe Asn Arg Gly Glu Cys
225                 230                 235

<210> SEQ ID NO 57
<211> LENGTH: 237
<212> TYPE: PRT
<213> ORGANISM: Artificial Sequence
<220> FEATURE:
<223> OTHER INFORMATION: LC variable region

<400> SEQUENCE: 57

Met Glu Thr Asp Thr Leu Leu Leu Trp Val Leu Leu Trp Val Pro
1               5                   10                  15

Gly Ser Thr Gly Asp Gln Ser Ala Leu Thr Gln Pro Ala Ser Val Ser
                20                  25                  30

Gly Ser Pro Gly Gln Ser Ile Thr Ile Ser Cys Thr Gly Thr Gly Ser
            35                  40                  45

Asp Ile Gly Gly Tyr Asn Phe Val Ser Trp Tyr Gln Gln Tyr Pro Gly

```
            50                  55                  60
Lys Ala Pro Lys Leu Ile Ile Tyr Glu Val Arg Ile Arg Ala Ser Gly
 65                  70                  75                  80

Val Ser Asn Arg Phe Ser Gly Ser Lys Ser Gly Asn Thr Ala Ser Leu
                 85                  90                  95

Thr Ile Ser Gly Leu Gln Ala Glu Asp Glu Ala Asp Tyr Tyr Cys Asn
            100                 105                 110

Ser Tyr Ser Ile His Ser Pro Trp Val Phe Gly Gly Thr Lys Leu
        115                 120                 125

Thr Val Leu Arg Gln Pro Lys Ala Ala Pro Ser Val Thr Leu Phe Pro
130                 135                 140

Pro Ser Ser Glu Glu Leu Gln Ala Asn Lys Ala Thr Leu Val Cys Leu
145                 150                 155                 160

Ile Ser Asp Phe Tyr Pro Gly Ala Val Thr Val Ala Trp Lys Ala Asp
                165                 170                 175

Ser Ser Pro Val Lys Ala Gly Val Glu Thr Thr Thr Pro Ser Lys Gln
            180                 185                 190

Ser Asn Asn Lys Tyr Ala Ala Ser Ser Tyr Leu Ser Leu Thr Pro Glu
            195                 200                 205

Gln Trp Glu Ser His Arg Ser Tyr Ser Cys Gln Val Thr His Glu Gly
        210                 215                 220

Ser Thr Val Glu Lys Thr Val Ala Pro Thr Glu Cys Ser
225                 230                 235
```

<210> SEQ ID NO 58
<211> LENGTH: 237
<212> TYPE: PRT
<213> ORGANISM: Artificial Sequence
<220> FEATURE:
<223> OTHER INFORMATION: LC variable region

<400> SEQUENCE: 58

```
Met Glu Thr Asp Thr Leu Leu Leu Trp Val Leu Leu Leu Trp Val Pro
 1               5                  10                  15

Gly Ser Thr Gly Asp Gln Ala Gly Leu Thr Gln Pro Ala Ser Val Ser
             20                  25                  30

Gly Ser Pro Gly Gln Ser Ile Thr Ile Ser Cys Thr Ala Ala Asn Ser
         35                  40                  45

Asp Ile Gly Asp Phe Asn Phe Val Ser Trp Tyr Gln Gln Arg Pro Asp
     50                  55                  60

Lys Ala Pro Lys Leu Met Val Tyr Glu Val Ser Ser Arg Pro Ser Gly
 65                  70                  75                  80

Val Ser Asn Arg Phe Ser Gly Ser Lys Ser Gly Asn Thr Ala Ser Leu
                 85                  90                  95

Thr Ile Ser Gly Leu Gln Ala Glu Asp Glu Ala Asp Tyr Tyr Cys Thr
            100                 105                 110

Ser Tyr Thr Ser Ser Ser Thr Phe Val Phe Gly Thr Gly Thr Lys Val
        115                 120                 125

Thr Val Leu Gly Gln Pro Lys Ala Asn Pro Thr Val Thr Leu Phe Pro
130                 135                 140

Pro Ser Ser Glu Glu Leu Gln Ala Asn Lys Ala Thr Leu Val Cys Leu
145                 150                 155                 160

Ile Ser Asp Phe Tyr Pro Gly Ala Val Thr Val Ala Trp Lys Ala Asp
                165                 170                 175

Ser Ser Pro Val Lys Ala Gly Val Glu Thr Thr Thr Pro Ser Lys Gln
```

```
                180             185             190
Ser Asn Asn Lys Tyr Ala Ala Ser Ser Tyr Leu Ser Leu Thr Pro Glu
            195                 200             205

Gln Trp Lys Ser His Arg Ser Tyr Ser Cys Gln Val Thr His Glu Gly
        210                 215                 220

Ser Thr Val Glu Lys Thr Val Ala Pro Thr Glu Cys Ser
225                 230                 235
```

<210> SEQ ID NO 59
<211> LENGTH: 236
<212> TYPE: PRT
<213> ORGANISM: Artificial Sequence
<220> FEATURE:
<223> OTHER INFORMATION: LC variable region

<400> SEQUENCE: 59

```
Thr Met Glu Thr Asp Thr Leu Leu Leu Trp Val Leu Leu Leu Trp Val
1               5                   10                  15

Pro Gly Ser Thr Gly Asp Glu Thr Thr Leu Thr Gln Ser Pro Gly Thr
            20                  25                  30

Leu Ser Leu Ser Pro Gly Glu Arg Ala Thr Leu Ser Cys Arg Ala Ser
        35                  40                  45

Gln Ser Val Ser Ser Thr Tyr Leu Ala Trp Tyr Gln Gln Lys Pro Gly
    50                  55                  60

Gln Ser Pro Arg Leu Leu Ile Tyr Gly Ala Ser Ser Arg Ala Thr Gly
65                  70                  75                  80

Ile Pro Asp Arg Phe Ser Gly Ser Gly Ser Gly Thr Gln Phe Thr Leu
                85                  90                  95

Thr Ile Asn Arg Leu Glu Pro Glu Asp Phe Ala Val Tyr Tyr Cys Gln
            100                 105                 110

Gln Phe Gly Ser Pro Trp Thr Phe Gly Gln Gly Thr Lys Val Glu Ile
        115                 120                 125

Lys Arg Thr Val Ala Ala Pro Ser Val Phe Ile Phe Pro Pro Ser Asp
    130                 135                 140

Glu Gln Leu Lys Ser Gly Thr Ala Ser Val Val Cys Leu Leu Asn Asn
145                 150                 155                 160

Phe Tyr Pro Arg Glu Ala Lys Val Gln Trp Lys Val Asp Asn Ala Leu
                165                 170                 175

Gln Ser Gly Asn Ser Gln Glu Ser Val Thr Glu Gln Asp Ser Lys Asp
            180                 185                 190

Ser Thr Tyr Ser Leu Ser Ser Thr Leu Thr Leu Ser Lys Ala Asp Tyr
        195                 200                 205

Glu Lys His Lys Val Tyr Ala Cys Glu Val Thr His Gln Gly Leu Ser
    210                 215                 220

Ser Pro Val Thr Lys Ser Phe Asn Arg Gly Glu Cys
225                 230                 235
```

<210> SEQ ID NO 60
<211> LENGTH: 235
<212> TYPE: PRT
<213> ORGANISM: Artificial Sequence
<220> FEATURE:
<223> OTHER INFORMATION: LC variable region

<400> SEQUENCE: 60

```
Met Glu Thr Asp Thr Leu Leu Leu Trp Val Leu Leu Leu Trp Val Pro
1               5                   10                  15
```

Gly Ser Thr Gly Asp Glu Thr Thr Leu Thr Gln Ser Pro Ala Thr Leu
            20                  25                  30

Ser Leu Ser Pro Gly Glu Arg Ala Thr Leu Ser Cys Arg Ala Ser Gln
        35                  40                  45

Ser Val Ser Ser Tyr Leu Ala Trp Tyr Gln His Lys Pro Gly Gln Ala
    50                  55                  60

Pro Arg Leu Leu Ile Tyr Gly Ala Ser Lys Arg Ala Thr Gly Ile Pro
65                  70                  75                  80

Ser Arg Phe Ser Gly Ser Gly Ser Gly Thr Asp Phe Ser Leu Thr Ile
                85                  90                  95

Ser Ser Leu Glu Pro Glu Asp Phe Ala Val Tyr Tyr Cys Gln His Arg
            100                 105                 110

Ser Asp Trp Arg Thr Thr Phe Gly Gln Gly Thr Arg Leu Glu Ile Lys
        115                 120                 125

Arg Thr Val Ala Ala Pro Ser Val Phe Ile Phe Pro Pro Ser Asp Glu
    130                 135                 140

Gln Leu Lys Ser Gly Thr Ala Ser Val Val Cys Leu Leu Asn Asn Phe
145                 150                 155                 160

Tyr Pro Arg Glu Ala Lys Val Gln Trp Lys Val Asp Asn Ala Leu Gln
                165                 170                 175

Ser Gly Asn Ser Gln Glu Ser Val Thr Glu Gln Asp Ser Lys Asp Ser
            180                 185                 190

Thr Tyr Ser Leu Ser Ser Thr Leu Thr Leu Ser Lys Ala Asp Tyr Glu
        195                 200                 205

Lys His Lys Val Tyr Ala Cys Glu Val Thr His Gln Gly Leu Ser Ser
    210                 215                 220

Pro Val Thr Lys Ser Phe Asn Arg Gly Glu Cys
225                 230                 235

<210> SEQ ID NO 61
<211> LENGTH: 235
<212> TYPE: PRT
<213> ORGANISM: Artificial Sequence
<220> FEATURE:
<223> OTHER INFORMATION: LC variable region

<400> SEQUENCE: 61

Met Glu Thr Asp Thr Leu Leu Leu Trp Val Leu Leu Leu Trp Val Pro
1               5                   10                  15

Gly Ser Thr Gly Asp Asp Ile Val Met Thr Gln Ser Pro Ser Thr Leu
            20                  25                  30

Ser Ala Ser Val Gly Asp Arg Val Thr Ile Thr Cys Arg Ala Ser Gln
        35                  40                  45

Ser Ile Asp Arg Trp Leu Ala Trp Tyr Gln Gln Lys Pro Gly Lys Ala
    50                  55                  60

Pro Lys Leu Leu Ile Tyr Gln Ala Ser Ser Leu Glu Arg Gly Val Pro
65                  70                  75                  80

Ser Arg Phe Ser Gly Ser Gly Ser Gly Thr Glu Phe Thr Leu Thr Ile
                85                  90                  95

Ser Ser Leu Gln Pro Asp Asp Phe Ala Thr Tyr Tyr Cys Gln Gln Tyr
            100                 105                 110

Asn Gly Tyr Pro Leu Thr Phe Gly Gly Gly Thr Lys Val Glu Ile Lys
        115                 120                 125

Arg Thr Val Ala Ala Pro Ser Val Phe Ile Phe Pro Pro Ser Asp Glu
    130                 135                 140

```
Gln Leu Lys Ser Gly Thr Ala Ser Val Val Cys Leu Leu Asn Asn Phe
145                 150                 155                 160

Tyr Pro Arg Glu Ala Lys Val Gln Trp Lys Val Asp Asn Ala Leu Gln
                165                 170                 175

Ser Gly Asn Ser Gln Glu Ser Val Thr Glu Gln Asp Ser Lys Asp Ser
            180                 185                 190

Thr Tyr Ser Leu Ser Ser Thr Leu Thr Leu Ser Lys Ala Asp Tyr Glu
        195                 200                 205

Lys His Lys Val Tyr Ala Cys Glu Val Thr His Gln Gly Leu Ser Ser
    210                 215                 220

Pro Val Thr Lys Ser Phe Asn Arg Gly Glu Cys
225                 230                 235

<210> SEQ ID NO 62
<211> LENGTH: 237
<212> TYPE: PRT
<213> ORGANISM: Artificial Sequence
<220> FEATURE:
<223> OTHER INFORMATION: LC variable region

<400> SEQUENCE: 62

Met Glu Thr Asp Thr Leu Leu Leu Trp Val Leu Leu Leu Trp Val Pro
1               5                   10                  15

Gly Ser Thr Gly Asp Asp Ile Gln Met Thr Gln Ser Pro Gly Thr Leu
            20                  25                  30

Ser Leu Ser Pro Gly Glu Arg Ala Thr Leu Ser Cys Arg Ala Ser Gln
        35                  40                  45

Ser Val Ile Ser Tyr Tyr Val Ala Trp Tyr Gln His Lys Gly Gly Gln
    50                  55                  60

Ala Pro Arg Leu Leu Ile Tyr Gly Ala Ser Ser Arg Ala Thr Gly Val
65                  70                  75                  80

Pro Asp Arg Phe Ser Gly Ser Gly Ser Gly Thr Asp Phe Thr Leu Thr
                85                  90                  95

Ile Ser Ser Leu Glu Pro Glu Asp Phe Ala Leu Tyr Tyr Cys Gln Tyr
            100                 105                 110

Tyr Gly Ser Ser Pro Leu Trp Ala Phe Gly Gln Gly Thr Lys Val Glu
        115                 120                 125

Ile Lys Arg Thr Val Ala Ala Pro Ser Val Phe Ile Phe Pro Pro Ser
    130                 135                 140

Asp Glu Gln Leu Lys Ser Gly Thr Ala Ser Val Val Cys Leu Leu Asn
145                 150                 155                 160

Asn Phe Tyr Pro Arg Glu Ala Lys Val Gln Trp Lys Val Asp Asn Ala
                165                 170                 175

Leu Gln Ser Gly Asn Ser Gln Glu Ser Val Thr Glu Gln Asp Ser Lys
            180                 185                 190

Asp Ser Thr Tyr Ser Leu Ser Ser Thr Leu Thr Leu Ser Lys Ala Asp
        195                 200                 205

Tyr Glu Lys His Lys Val Tyr Ala Cys Glu Val Thr His Gln Gly Leu
    210                 215                 220

Ser Ser Pro Val Thr Lys Ser Phe Asn Arg Gly Glu Cys
225                 230                 235

<210> SEQ ID NO 63
<211> LENGTH: 235
<212> TYPE: PRT
<213> ORGANISM: Artificial Sequence
<220> FEATURE:
```

<223> OTHER INFORMATION: LC variable region

<400> SEQUENCE: 63

Met Glu Thr Asp Thr Leu Leu Leu Trp Val Leu Leu Leu Trp Val Pro
1               5                   10                  15

Gly Ser Thr Gly Asp Glu Ile Val Leu Thr Gln Ser Pro Ala Thr Leu
            20                  25                  30

Ser Val Ser Pro Gly Gly Arg Ala Ser Leu Ser Cys Arg Ala Ser Gln
        35                  40                  45

Ser Ile Gly Asp Lys Leu Ser Trp Tyr Gln Gln Lys Pro Gly Gln Ala
    50                  55                  60

Pro Arg Leu Val Ile Tyr Gly Ala Tyr Thr Arg Ala Thr Asp Ile Ser
65                  70                  75                  80

Pro Arg Phe Ser Gly Ser Arg Ser Gly Thr Asp Phe Asn Leu Thr Ile
                85                  90                  95

Ser Arg Met Gln Ser Gly Asp Phe Ala Val Tyr Phe Cys Gln Gln Tyr
            100                 105                 110

Glu Asn Trp Pro Arg Thr Phe Gly Gln Gly Thr Lys Leu Glu Ile Lys
        115                 120                 125

Arg Thr Val Ala Ala Pro Ser Val Phe Ile Phe Pro Pro Ser Asp Glu
130                 135                 140

Gln Leu Lys Ser Gly Thr Ala Ser Val Val Cys Leu Leu Asn Asn Phe
145                 150                 155                 160

Tyr Pro Arg Glu Ala Lys Val Gln Trp Lys Val Asp Asn Ala Leu Gln
                165                 170                 175

Ser Gly Asn Ser Gln Glu Ser Val Thr Glu Gln Asp Ser Lys Asp Ser
            180                 185                 190

Thr Tyr Ser Leu Ser Ser Thr Leu Thr Leu Ser Lys Ala Asp Tyr Glu
        195                 200                 205

Lys His Lys Val Tyr Ala Cys Glu Val Thr His Gln Gly Leu Ser Ser
    210                 215                 220

Pro Val Thr Lys Ser Phe Asn Arg Gly Glu Cys
225                 230                 235

<210> SEQ ID NO 64
<211> LENGTH: 291
<212> TYPE: PRT
<213> ORGANISM: Artificial Sequence
<220> FEATURE:
<223> OTHER INFORMATION: LC variable region

<400> SEQUENCE: 64

Met Glu Thr Asp Thr Leu Leu Leu Trp Val Leu Leu Leu Trp Val Pro
1               5                   10                  15

Gly Ser Thr Gly Asp Asp Ile Gln Met Thr Gln Ser Pro Ser Ser Leu
            20                  25                  30

Ser Ala Ser Val Gly Asp Arg Val Ile Ile Thr Cys Arg Ala Ser Gln
        35                  40                  45

Ser Ile Ser Ser Ser Leu Asn Trp Tyr Gln Gln Lys Pro Gly Lys Ala
    50                  55                  60

Pro Lys Leu Leu Ile Tyr Ala Ala Val Asn Leu Glu Thr Gly Val Pro
65                  70                  75                  80

Ser Arg Phe Ser Gly Ser Gly Phe Gly Thr Asp Phe Thr Leu Ala Ile
                85                  90                  95

Ser Asn Val Gln Pro Glu Asp Phe Ala Thr Tyr Tyr Cys Gln Gln Ser
            100                 105                 110

-continued

```
Asp Thr Arg Thr Phe Gly Arg Gly Thr Lys Leu Asp Val Lys Arg Thr
            115                 120                 125
Val Ala Ala Pro Ser Val Phe Ile Phe Pro Pro Ser Asp Glu Gln Leu
        130                 135                 140
Lys Ser Gly Thr Ala Ser Val Val Cys Leu Leu Asn Asn Phe Tyr Pro
145                 150                 155                 160
Arg Glu Ala Lys Val Gln Trp Lys Val Asp Asn Ala Leu Gln Ser Gly
                165                 170                 175
Asn Ser Gln Glu Ser Val Thr Glu Gln Asp Ser Lys Asp Ser Thr Tyr
            180                 185                 190
Ser Leu Ser Ser Thr Leu Thr Leu Ser Lys Ala Asp Tyr Glu Lys His
        195                 200                 205
Lys Val Tyr Ala Cys Glu Val Thr His Gln Gly Leu Ser Ser Pro Val
210                 215                 220
Thr Lys Ser Phe Asn Arg Gly Glu Val Leu Gly Gly Arg Lys Leu Gly
225                 230                 235                 240
Arg His Gly Pro Thr Cys Leu Leu Gln Leu Ile Met Val Thr Asn Lys
                245                 250                 255
Ala Ile Ala Ser Gln Ile Ser Gln Ile Lys His Phe Phe His Cys Ile
            260                 265                 270
Leu Val Val Cys Pro Asn Ser Ser Met Tyr Leu Ile Met Ser Gly
        275                 280                 285
Ser Gly Ile
    290

<210> SEQ ID NO 65
<211> LENGTH: 8
<212> TYPE: PRT
<213> ORGANISM: human

<400> SEQUENCE: 65

Gly Phe Asn Phe Arg Ala Tyr Gly
1               5

<210> SEQ ID NO 66
<211> LENGTH: 9
<212> TYPE: PRT
<213> ORGANISM: human

<400> SEQUENCE: 66

Ile Trp Ser Ala Glu Thr Asn Arg His
1               5

<210> SEQ ID NO 67
<211> LENGTH: 13
<212> TYPE: PRT
<213> ORGANISM: human

<400> SEQUENCE: 67

Ala Lys Ala Arg Pro Gly Tyr Asp Tyr Val Val Asp Leu
1               5                   10

<210> SEQ ID NO 68
<211> LENGTH: 8
<212> TYPE: PRT
<213> ORGANISM: human

<400> SEQUENCE: 68

Gly Phe Ser Phe Ser Ser Tyr Ser
```

```
<210> SEQ ID NO 69
<211> LENGTH: 9
<212> TYPE: PRT
<213> ORGANISM: human

<400> SEQUENCE: 69

Ile Asn Ser Asp Gly Ser Thr Lys Ile
1               5

<210> SEQ ID NO 70
<211> LENGTH: 12
<212> TYPE: PRT
<213> ORGANISM: human

<400> SEQUENCE: 70

Val Arg Leu Val His Tyr Asp Trp Ser Pro Phe Val
1               5                   10

<210> SEQ ID NO 71
<211> LENGTH: 8
<212> TYPE: PRT
<213> ORGANISM: human

<400> SEQUENCE: 71

Gly Phe Thr Phe Thr Arg Phe Thr
1               5

<210> SEQ ID NO 72
<211> LENGTH: 9
<212> TYPE: PRT
<213> ORGANISM: human

<400> SEQUENCE: 72

Ile Ser Ser Gly Ser Ser Asp Ile Asn
1               5

<210> SEQ ID NO 73
<211> LENGTH: 16
<212> TYPE: PRT
<213> ORGANISM: human

<400> SEQUENCE: 73

Ala Lys Asp Pro Arg Ser Gly Ile Ser Gly Arg Tyr Gly Met Asp Val
1               5                   10                  15

<210> SEQ ID NO 74
<211> LENGTH: 8
<212> TYPE: PRT
<213> ORGANISM: human

<400> SEQUENCE: 74

Gly Phe Met Phe Glu Arg Tyr Ser
1               5

<210> SEQ ID NO 75
<211> LENGTH: 10
<212> TYPE: PRT
<213> ORGANISM: human

<400> SEQUENCE: 75

Ile Ser Ser Leu Ser Gly Ser His Ile Asn
1               5                   10
```

<210> SEQ ID NO 76
<211> LENGTH: 15
<212> TYPE: PRT
<213> ORGANISM: human

<400> SEQUENCE: 76

Ala Arg Asp Arg Arg Ser Gly Ser Ser Pro Val Pro Leu Asp Val
1               5                   10                  15

<210> SEQ ID NO 77
<211> LENGTH: 8
<212> TYPE: PRT
<213> ORGANISM: human

<400> SEQUENCE: 77

Gly Gly Pro Phe Ser Gly Ala Tyr
1               5

<210> SEQ ID NO 78
<211> LENGTH: 8
<212> TYPE: PRT
<213> ORGANISM: human

<400> SEQUENCE: 78

Ala Gly Arg Ser Gly Thr Thr Asn
1               5

<210> SEQ ID NO 79
<211> LENGTH: 18
<212> TYPE: PRT
<213> ORGANISM: human

<400> SEQUENCE: 79

Gly Arg Arg Gln Ile Met Ser Leu Ser Asn Leu Tyr Lys Arg Pro Val
1               5                   10                  15

Asp Ser

<210> SEQ ID NO 80
<211> LENGTH: 8
<212> TYPE: PRT
<213> ORGANISM: human

<400> SEQUENCE: 80

Gly Phe Thr Phe Ser Ser Tyr Ser
1               5

<210> SEQ ID NO 81
<211> LENGTH: 9
<212> TYPE: PRT
<213> ORGANISM: human

<400> SEQUENCE: 81

Ile Ser Ser Gly Gly Ser Ser Ile His
1               5

<210> SEQ ID NO 82
<211> LENGTH: 16
<212> TYPE: PRT
<213> ORGANISM: human

<400> SEQUENCE: 82

Val Arg Asp Pro Arg Ser Gly Ile Ser Gly Arg Tyr Gly Met Asp Val
1               5                   10                  15

<210> SEQ ID NO 83
<211> LENGTH: 8
<212> TYPE: PRT
<213> ORGANISM: human

<400> SEQUENCE: 83

Gly Tyr Thr Phe Thr Lys Tyr Gly
1               5

<210> SEQ ID NO 84
<211> LENGTH: 9
<212> TYPE: PRT
<213> ORGANISM: human

<400> SEQUENCE: 84

Ile Ser Ala Phe Asn Gly Tyr Thr Arg
1               5

<210> SEQ ID NO 85
<211> LENGTH: 21
<212> TYPE: PRT
<213> ORGANISM: human

<400> SEQUENCE: 85

Ala Arg Gln Tyr Pro Asp Gln Tyr Ser Ser Ser Gly Trp Pro Arg Leu
1               5                   10                  15

Phe Ala Met Asp Val
            20

<210> SEQ ID NO 86
<211> LENGTH: 8
<212> TYPE: PRT
<213> ORGANISM: human

<400> SEQUENCE: 86

Gly Phe Thr Phe Ser Arg Asp Thr
1               5

<210> SEQ ID NO 87
<211> LENGTH: 9
<212> TYPE: PRT
<213> ORGANISM: human

<400> SEQUENCE: 87

Ile Ser Ser Gly Ser Ser Asp Ile Asn
1               5

<210> SEQ ID NO 88
<211> LENGTH: 16
<212> TYPE: PRT
<213> ORGANISM: human

<400> SEQUENCE: 88

Ala Arg Asp Pro Arg Ser Gly Ile Ser Gly Arg Tyr Gly Met Asp Val
1               5                   10                  15

<210> SEQ ID NO 89
<211> LENGTH: 8
<212> TYPE: PRT
<213> ORGANISM: human

<400> SEQUENCE: 89

Gly Phe Thr Phe Ser Thr Tyr Ser
1               5

<210> SEQ ID NO 90
<211> LENGTH: 10
<212> TYPE: PRT
<213> ORGANISM: human

<400> SEQUENCE: 90

Ile Ser Ser Arg Ser Gly Ser His Ile Asn
1               5                   10

<210> SEQ ID NO 91
<211> LENGTH: 15
<212> TYPE: PRT
<213> ORGANISM: human

<400> SEQUENCE: 91

Ala Arg Asp Arg Arg Ser Gly Thr Ser Pro Leu Pro Leu Asp Val
1               5                   10                  15

<210> SEQ ID NO 92
<211> LENGTH: 9
<212> TYPE: PRT
<213> ORGANISM: human

<400> SEQUENCE: 92

Gly Tyr Ser Ile Ser Ser Gly Tyr Tyr
1               5

<210> SEQ ID NO 93
<211> LENGTH: 8
<212> TYPE: PRT
<213> ORGANISM: human

<400> SEQUENCE: 93

Ile Tyr Arg Ser Gly Ser Thr Tyr
1               5

<210> SEQ ID NO 94
<211> LENGTH: 31
<212> TYPE: PRT
<213> ORGANISM: human

<400> SEQUENCE: 94

Ala Arg Ser Gly Ile Lys Val Ala Asp Asp Tyr Tyr Tyr Glu Met Asp
1               5                   10                  15

Val Trp Gly Gln Gly Thr Asp Asp Tyr Ser Tyr Ala Met Asp Val
            20                  25                  30

<210> SEQ ID NO 95
<211> LENGTH: 8
<212> TYPE: PRT
<213> ORGANISM: human

<400> SEQUENCE: 95

Gly Phe Thr Phe Ser Ser Tyr Ser
1               5

<210> SEQ ID NO 96
<211> LENGTH: 9
<212> TYPE: PRT
<213> ORGANISM: human

<400> SEQUENCE: 96

Ile Ser Ser Gly Ser Ser Tyr Ile Glu

-continued

```
<210> SEQ ID NO 97
<211> LENGTH: 15
<212> TYPE: PRT
<213> ORGANISM: human

<400> SEQUENCE: 97

Ala Arg His Thr Ala Arg Ile Asp Ser Tyr His Gly Met Asp Val
1               5                   10                  15

<210> SEQ ID NO 98
<211> LENGTH: 8
<212> TYPE: PRT
<213> ORGANISM: human

<400> SEQUENCE: 98

Gly Glu Ser Phe Asn Gly Phe Phe
1               5

<210> SEQ ID NO 99
<211> LENGTH: 8
<212> TYPE: PRT
<213> ORGANISM: human

<400> SEQUENCE: 99

Ile Asn His Leu Ala Ser Thr Gly
1               5

<210> SEQ ID NO 100
<211> LENGTH: 18
<212> TYPE: PRT
<213> ORGANISM: human

<400> SEQUENCE: 100

Ala Arg Gly Tyr Ser Tyr Gly Phe Ala Trp Pro Asn Tyr His Tyr Leu
1               5                   10                  15

Asp Val

<210> SEQ ID NO 101
<211> LENGTH: 8
<212> TYPE: PRT
<213> ORGANISM: human

<400> SEQUENCE: 101

Gly Phe Thr Phe Ser Ser His Ala
1               5

<210> SEQ ID NO 102
<211> LENGTH: 9
<212> TYPE: PRT
<213> ORGANISM: human

<400> SEQUENCE: 102

Phe Ser Gly Ser Ser Gly Thr Thr Lys
1               5

<210> SEQ ID NO 103
<211> LENGTH: 17
<212> TYPE: PRT
<213> ORGANISM: human

<400> SEQUENCE: 103

Ala Lys Gly Phe Ser Pro Phe Arg Gly Val Gln Phe Pro Tyr Phe Asp
```

Tyr

<210> SEQ ID NO 104
<211> LENGTH: 8
<212> TYPE: PRT
<213> ORGANISM: human

<400> SEQUENCE: 104

Gly Phe Thr Phe Lys Ser Tyr Ser
1               5

<210> SEQ ID NO 105
<211> LENGTH: 9
<212> TYPE: PRT
<213> ORGANISM: human

<400> SEQUENCE: 105

Ile Thr Ser Gly Gly Ser Lys Thr Tyr
1               5

<210> SEQ ID NO 106
<211> LENGTH: 15
<212> TYPE: PRT
<213> ORGANISM: human

<400> SEQUENCE: 106

Ala Arg Ser Leu His Ser Thr Ser Gln Pro Ser Tyr Met Asp Val
1               5                   10                  15

<210> SEQ ID NO 107
<211> LENGTH: 8
<212> TYPE: PRT
<213> ORGANISM: human

<400> SEQUENCE: 107

Gly Val Ser Thr Arg Asn Tyr Tyr
1               5

<210> SEQ ID NO 108
<211> LENGTH: 8
<212> TYPE: PRT
<213> ORGANISM: human

<400> SEQUENCE: 108

Ile Phe Asn Ile Gly Thr Thr Asn
1               5

<210> SEQ ID NO 109
<211> LENGTH: 13
<212> TYPE: PRT
<213> ORGANISM: human

<400> SEQUENCE: 109

Ala Ser Gly Phe Glu Tyr Gly Asp Tyr Thr Phe Asp Tyr
1               5                   10

<210> SEQ ID NO 110
<211> LENGTH: 8
<212> TYPE: PRT
<213> ORGANISM: human

<400> SEQUENCE: 110

Gly Phe Asn Phe Asn Lys Tyr Asn

```
<210> SEQ ID NO 111
<211> LENGTH: 9
<212> TYPE: PRT
<213> ORGANISM: human

<400> SEQUENCE: 111

Ile Ser Ala Leu Ser Thr Tyr Ile Tyr
1               5

<210> SEQ ID NO 112
<211> LENGTH: 14
<212> TYPE: PRT
<213> ORGANISM: human

<400> SEQUENCE: 112

Ala Arg Glu Ile Arg Arg Ala Ser Thr Trp Ser Ala Asp Leu
1               5                   10

<210> SEQ ID NO 113
<211> LENGTH: 6
<212> TYPE: PRT
<213> ORGANISM: human

<400> SEQUENCE: 113

Arg Asp Ile Asn Thr Tyr
1               5

<210> SEQ ID NO 114
<211> LENGTH: 9
<212> TYPE: PRT
<213> ORGANISM: human

<400> SEQUENCE: 114

Gln Gln Tyr Ser Ile Tyr Pro Leu Ser
1               5

<210> SEQ ID NO 115
<211> LENGTH: 6
<212> TYPE: PRT
<213> ORGANISM: human

<400> SEQUENCE: 115

Gln Ser Ile Asn Asn Trp
1               5

<210> SEQ ID NO 116
<211> LENGTH: 9
<212> TYPE: PRT
<213> ORGANISM: human

<400> SEQUENCE: 116

Gln Gln Tyr Asn Ser Asn Ser Trp Thr
1               5

<210> SEQ ID NO 117
<211> LENGTH: 12
<212> TYPE: PRT
<213> ORGANISM: human

<400> SEQUENCE: 117

Gln Ser Val Leu Tyr Ser Ser Asn Asn Lys Asn Tyr
1               5                   10
```

<210> SEQ ID NO 118
<211> LENGTH: 9
<212> TYPE: PRT
<213> ORGANISM: human

<400> SEQUENCE: 118

Gln Gln Tyr Tyr Ser Thr Pro Pro Thr
1               5

<210> SEQ ID NO 119
<211> LENGTH: 9
<212> TYPE: PRT
<213> ORGANISM: human

<400> SEQUENCE: 119

Ser Ser Asp Val Gly Ala Tyr Asn Tyr
1               5

<210> SEQ ID NO 120
<211> LENGTH: 10
<212> TYPE: PRT
<213> ORGANISM: human

<400> SEQUENCE: 120

Ser Ser Tyr Ser Thr Asn Ser Pro Trp Val
1               5                   10

<210> SEQ ID NO 121
<211> LENGTH: 7
<212> TYPE: PRT
<213> ORGANISM: human

<400> SEQUENCE: 121

Gln Ser Val Thr Lys Asn Tyr
1               5

<210> SEQ ID NO 122
<211> LENGTH: 10
<212> TYPE: PRT
<213> ORGANISM: human

<400> SEQUENCE: 122

His Gln Tyr Gly Ser Ser Pro Pro Tyr Thr
1               5                   10

<210> SEQ ID NO 123
<211> LENGTH: 9
<212> TYPE: PRT
<213> ORGANISM: human

<400> SEQUENCE: 123

Gln Thr Val Leu Phe Thr Ser Tyr Tyr
1               5

<210> SEQ ID NO 124
<211> LENGTH: 9
<212> TYPE: PRT
<213> ORGANISM: human

<400> SEQUENCE: 124

Gln Gln Tyr His Thr Pro Pro Phe Thr
1               5

<210> SEQ ID NO 125

```
<211> LENGTH: 6
<212> TYPE: PRT
<213> ORGANISM: human

<400> SEQUENCE: 125

Gln Asn Val Ile Asn Asn
1               5

<210> SEQ ID NO 126
<211> LENGTH: 9
<212> TYPE: PRT
<213> ORGANISM: human

<400> SEQUENCE: 126

Gln Gln Tyr Asn Asp Trp Pro Arg Ser
1               5

<210> SEQ ID NO 127
<211> LENGTH: 7
<212> TYPE: PRT
<213> ORGANISM: human

<400> SEQUENCE: 127

Gln Ser Val Asn Ser Ile Phe
1               5

<210> SEQ ID NO 128
<211> LENGTH: 10
<212> TYPE: PRT
<213> ORGANISM: human

<400> SEQUENCE: 128

Gln Gln Tyr His Ser Ser Pro Lys Leu Thr
1               5                   10

<210> SEQ ID NO 129
<211> LENGTH: 9
<212> TYPE: PRT
<213> ORGANISM: human

<400> SEQUENCE: 129

Gly Ser Asp Ile Gly Gly Tyr Asn Phe
1               5

<210> SEQ ID NO 130
<211> LENGTH: 10
<212> TYPE: PRT
<213> ORGANISM: human

<400> SEQUENCE: 130

Asn Ser Tyr Ser Ile His Ser Pro Trp Val
1               5                   10

<210> SEQ ID NO 131
<211> LENGTH: 9
<212> TYPE: PRT
<213> ORGANISM: human

<400> SEQUENCE: 131

Asn Ser Asp Ile Gly Asp Phe Asn Phe
1               5

<210> SEQ ID NO 132
<211> LENGTH: 10
<212> TYPE: PRT
```

<213> ORGANISM: human

<400> SEQUENCE: 132

Thr Ser Tyr Thr Ser Ser Ser Thr Phe Val
1               5                   10

<210> SEQ ID NO 133
<211> LENGTH: 7
<212> TYPE: PRT
<213> ORGANISM: human

<400> SEQUENCE: 133

Gln Ser Val Ser Ser Thr Tyr
1               5

<210> SEQ ID NO 134
<211> LENGTH: 8
<212> TYPE: PRT
<213> ORGANISM: human

<400> SEQUENCE: 134

Gln Gln Phe Gly Ser Pro Trp Thr
1               5

<210> SEQ ID NO 135
<211> LENGTH: 6
<212> TYPE: PRT
<213> ORGANISM: human

<400> SEQUENCE: 135

Gln Ser Val Ser Ser Tyr
1               5

<210> SEQ ID NO 136
<211> LENGTH: 9
<212> TYPE: PRT
<213> ORGANISM: human

<400> SEQUENCE: 136

Gln His Arg Ser Asp Trp Arg Thr Thr
1               5

<210> SEQ ID NO 137
<211> LENGTH: 6
<212> TYPE: PRT
<213> ORGANISM: human

<400> SEQUENCE: 137

Gln Ser Ile Asp Arg Trp
1               5

<210> SEQ ID NO 138
<211> LENGTH: 9
<212> TYPE: PRT
<213> ORGANISM: human

<400> SEQUENCE: 138

Gln Gln Tyr Asn Gly Tyr Pro Leu Thr
1               5

<210> SEQ ID NO 139
<211> LENGTH: 7
<212> TYPE: PRT
<213> ORGANISM: human

```
<400> SEQUENCE: 139

Gln Ser Val Ile Ser Tyr Tyr
1               5

<210> SEQ ID NO 140
<211> LENGTH: 10
<212> TYPE: PRT
<213> ORGANISM: human

<400> SEQUENCE: 140

Gln Tyr Tyr Gly Ser Ser Pro Leu Trp Ala
1               5                   10

<210> SEQ ID NO 141
<211> LENGTH: 6
<212> TYPE: PRT
<213> ORGANISM: human

<400> SEQUENCE: 141

Gln Ser Ile Gly Asp Lys
1               5

<210> SEQ ID NO 142
<211> LENGTH: 9
<212> TYPE: PRT
<213> ORGANISM: human

<400> SEQUENCE: 142

Gln Gln Tyr Glu Asn Trp Pro Arg Thr
1               5

<210> SEQ ID NO 143
<211> LENGTH: 6
<212> TYPE: PRT
<213> ORGANISM: human

<400> SEQUENCE: 143

Gln Ser Ile Ser Ser Ser
1               5

<210> SEQ ID NO 144
<211> LENGTH: 7
<212> TYPE: PRT
<213> ORGANISM: human

<400> SEQUENCE: 144

Gln Gln Ser Asp Thr Arg Thr
1               5
```

ARENAVIRUS MONOCLONAL ANTIBODIES AND USES

CROSS REFERENCE TO RELATED APPLICATIONS

This application is a 371 of International Application No. PCT/US2017/064744, filed Dec. 5, 2017, which claims the benefit of U.S. Provisional Application Ser. No. 62/430,225 filed on Dec. 5, 2016, each of which is incorporated herein by reference in its entirety.

STATEMENT REGARDING FEDERALLY SPONSORED RESEARCH OR DEVELOPMENT

This invention was made, in part, with support provided by the United States government under Grant Nos. U19 AI109762, 1 R01 AI104621, R43 AI120472, and NIAID Project No. 272200900049C-0-0-1 from the National Institutes of Health. The Government may have certain rights in this invention.

FIELD OF THE INVENTION

The present invention relates to novel arenavirus monoclonal antibodies, to compositions comprising the arenavirus monoclonal antibodies, and methods comprising the same.

INCORPORATION OF SEQUENCE LISTING

Biological sequence information for this application is included in an ASCII text file having the file name "TU-439-SEQ-R1.txt", created on Aug. 28, 2019, and having a file size of 121,021 bytes, which is incorporated herein by reference.

BACKGROUND

Lassa virus (LASV) and several other members of the Arenaviridae are classified as Biosafety Level 4 and NIAID Biodefense Category A agents. The present invention will fill a vital biodefense need for rapid multiagent immunodiagnostic assays for arenaviruses and for effective therapeutics against arenaviral disease, and will provide a major advance for public health management of an important family of viral pathogens. Several arenaviruses, chiefly Lassa virus (LASV) in West Africa, cause hemorrhagic fever (HF) disease in humans and pose serious public health concerns in their endemic regions. The global endemicity of the prototypic arenavirus lymphocytic choriomeningitis virus (LCMV) is not a causative agent of HF, but mounting evidence indicates that LCMV is a neglected human pathogen of clinical significance that can cause neurologic disease in the fetus, child and adult stages. In addition, LCMV poses a special threat in immune-compromised individuals, as tragically illustrated by recent cases of transplant-associated infections by LCMV with a fatal outcome in the United States and Australia. Moreover, the high seroprevalence of LCMV within different urban populations across the world, including the US, has raised the question of whether LCMV may contribute to the many cases of undiagnosed aseptic meningitis reported yearly.

Lassa fever. The most prevalent arenaviral disease is Lassa fever (LF), an often-fatal hemorrhagic fever named for the Nigerian town in which the first described cases occurred in 1969 (Buckley and Casals, 1970). Parts of Guinea, Sierra Leone, Nigeria, and Liberia are endemic for the etiologic agent, LASV (Birmingham and Kenyon, 2001). Although detailed surveillance of LASV is hampered by many factors, including the lack of a widely available diagnostic test, it is clear that the public health impact is immense. There are as many as 300,000 cases of Lassa per year in West Africa and 5,000 deaths (see the CDC website at www(dot)cdc(dot)gov/ncidod/dvrd/spb/mnpages/dispages/lassaf(dot)htm). In some parts of Sierra Leone, 10-16% of all patients admitted to hospitals have Lassa fever. Case fatality rates for Lassa fever have typically been reported as 15% to 20%, and as high as 45% during epidemics, with a recent multi-year study in Sierra Leone reporting a 69% rate (Schaffer et al., 2014). LASV has been associated with severe nosocomial outbreaks involving health care workers and laboratory personnel (Fisher-Hoch et al., 1995). The mortality rate for women in the last month of pregnancy is always high, about 90%, and LASV infection causes high rates of fetal death at all stages of gestation (Walls, 1985). Mortality rates for Lassa appear to be higher in non-Africans, which is of concern because Lassa is the most commonly exported hemorrhagic fever (Haas et al., 2003; Holmes et al., 1990).

Old and New World arenaviruses. Arenaviruses are enveloped viruses with a bi-segmented negative strand (NS) RNA genome. Each genomic RNA segment, L (ca. 7.3 kb) and S (ca. 3.5 kb), uses an ambisense coding strategy to direct the synthesis of two polypeptides in opposite orientation, separated by a non-coding intergenic region. The S RNA encodes the viral glycoprotein precursor (GPC) and the nucleoprotein (NP). GPC is co- and post-translationally processed to yield the two mature virion surface glycoproteins GP1 and GP2 that together with the stable signal peptide (SSP) form the GP complex that decorates the virus surface and directs virus cell entry via receptor-mediated endocytosis. The L RNA encodes the viral RNA dependent RNA polymerase (L polymerase), and the small RING finger protein Z that has functions of a bona fide matrix protein. The structure of arenavirus GP2 appears to be a class I fusion protein, which is common to envelope glycoproteins of myxoviruses, retroviruses and filoviruses (Gallaher, DiSimone, and Buchmeier, 2001). When viewed by transmission electron microscopy, the enveloped spherical virions (diameter: 110-130 nm) show grainy particles that are ribosomes acquired from the host cells (Murphy and Whitfield, 1975), hence the basis for the family name of the Latin word "arena," which means "sandy." The arenaviruses are divided into the Old World or lymphocytic choriomeningitis virus (LCMV)/LASV complex and the New World or Tacaribe complex (Bowen, Peters, and Nichol, 1997). There is considerable diversity amongst members of the Arenaviridae (FIG. 1), and even within the same virus species (Bowen et al., 2000). In addition to LASV, other arenaviruses that cause severe illness in humans and are classified as BSL-4 and NIAID category A agents include the New World arenaviruses Machupo virus (MACV, Bolivian hemorrhagic fever), Junin virus (JUNV, Argentine hemorrhagic fever), Guanarito virus (GUAV, Venezuelan hemorrhagic fever) and Sabiá virus (SABV, Brazilian hemorrhagic fever). Arenaviruses are zoonotic; each virus is associated with a specific species of rodent (Bowen, Peters, and Nichol, 1997). The LCMV/LASV complex viruses are associated with Old World rats and mice (family Muridae, subfamily Murinae). Tacaribe complex viruses are generally associated with New World rats and mice (family Muridae, subfamily Sigmodontinae); however, the reservoir of Tacaribe virus itself appears to be a bat (Bowen, Peters, and Nichol, 1996). The reservoir of LASV is the "multimammate rat" of the genus *Mastomys*

(Monath et al., 1974). *Mastomys* rats are ubiquitous in sub-Saharan Africa (Demby et al., 2001) and are known to be peridomestic, often living in human homes; however, many questions regarding the taxonomy, geographic distribution and ecobiology of *Mastomys* species are unanswered. As with the natural hosts of other arenaviruses, *Mastomys* show no symptoms of LASV infection, but shed the virus in saliva, urine and feces. Eradication of the widely distributed rodent reservoirs of LASV and other arenaviruses is impractical and ecologically undesirable.

Arenaviruses cause chronic infections of rodents across the world with human infections mostly occurring through mucosal exposure or by direct contact of abraded skin with infectious materials. Arenaviruses are easily transmitted to humans from rodents via direct contact with rodent excreta or by contact with or ingestion of excreta-contaminated materials (Bausch et al., 2001; Demby et al., 2001). In the case of *Mastomys* species, infection may also occur when the animals are caught, prepared as a food source and eaten. Most arenaviruses, including LASV, are readily transmitted between humans, thus making nosocomial infection another matter of great concern. Human-to-human transmission can occur via exposure to blood or body fluids. LASV can also be transmitted to sexual partners of convalescent men via semen up to six weeks post-infection.

Natural history of Lassa fever. Signs and symptoms of Lassa fever, which occur 1-3 weeks after virus exposure, are highly variable, but typically begin with the insidious onset of fever and other nonspecific symptoms such as headache, generalized weakness, and malaise, followed within days by sore throat, retrosternal pain, conjunctival injection, abdominal pain, and diarrhea. LASV infects endothelial cells, resulting in increased capillary permeability, which can produce diminished effective circulating volume (Peters et al., 1989). Severe cases progress to facial and neck swelling, shock and multiorgan system failure. Frank bleeding, usually mucosal (gums, etc.), occurs in less than a third of cases, but confers a poor prognosis. Neurological problems have also been described, including hearing loss, tremors, and encephalitis. Patients who survive begin to defervesce 2-3 weeks after onset of the disease. Temporary or permanent unilateral or bilateral deafness that occurs in a third of Lassa patients during convalescence is not associated with the severity of the acute disease (Cummins et al., 1990; Rybak, 1990; Hartnet et al., 2015; Anderson et al., 2015; Branco et al., October 2011; Grove et al., 2011; Branco et al., 2010; Branco et al., August 2011).

Potential for use of arenaviruses as bioweapons. In addition to high case fatality rates, arenaviruses have many features that enhance their potential as bioweapons. Arenaviruses have relatively stable virions, do not require passage via insect vectors, are spread easily by human-to-human contact, and may be capable of aerosol spread or other simple means of dispersal. The high prevalence of Lassa fever in western Africa coupled with the ease of travel to and from this area and endemic areas for MACV, JUNV, GUAV, SABV and other highly pathogenic arenaviruses permits easy access to these viruses for use as a bioweapon. A cluster of hemorrhagic fever cases in the United States caused by any arenavirus would be a major public health incident. Because febrile illnesses are common, and the use of reliable arenavirus diagnostic tests is not commonplace, an initial cluster of undiagnosed cases would greatly increase the impact of the attack and permit wider dissemination via human-to-human contact. The potential use of LASV and other arenaviruses as a biological weapon directed against civilian or military targets potentiated the commercial development of effective diagnostics, which the VHFC has accomplished, through the marketing of immunodiagnostic tests for the rapid detection of LASV infections (ReLASV Rapid Diagnostic Test [RDT]™, RePanLASV RDT™) and companion ELISA diagnostics for the detection of antigenemia and the immunoglobulin (Ig) M (IgM) and G (IgG) response to infection (www(dot)zalgenlabs(dot)com/products).

Treatment/prevention of arenavirus infections. There are no Food and Drug Administration (FDA)-approved arenavirus vaccines and current anti-arenaviral therapy is limited to an off-label use of the antiviral drug ribavirin that is only partially effective and can cause significant side effects. Ribavirin may be effective in the treatment of Lassa fever only if administered early in the course of illness (Johnson et al., 1987; McCormick et al., 1986). Ribavirin administered to patients with a high virus load (and therefore a high risk for mortality) within the first six days of illness reduced the case-fatality rate from 55% to 5% (McCormick et al., 1986). Several anecdotal reports suggest that this drug can also be effective against other arenaviral hemorrhagic fevers (Barry et al., 1995; Kilgore et al., 1997; Weissenbacher et al., 1986a; Weissenbacher et al., 1986b). The efficacy of prophylactic treatments for Lassa fever is unknown, although it has been suggested that people with high-risk exposures be treated with oral ribavirin. Control of LCMV infection is mediated mainly by cellular immune responses, and significant titers of neutralizing antibodies to LCMV appear usually only after the patients have clinically recovered. However, passive antibody transfer has been shown to confer protection in animal models of LCMV infection (Enria et al., 1984; Frame et al., 1984; Jahrling, 1983; Jahrling and Peters, 1984; Jahrling, Peters, and Stephen, 1984; Weissenbacher et al., 1986a). Thus, antibody-based therapy may provide a safer alternative for treatment of LCMV based on predetermined correlates of protection. Previous studies of passive transfer of serum to treat Argentine hemorrhagic fever (AHF) and Lassa fever provide a strong rationale for the methods disclosed herein. Although passive transfer of serum has proven effective against the New and Old World virus, this approach is not scalable to protect large populations in the case of a hypothetical release of these viruses. Another issue is the safety of transfused serum or plasma, in particular those living in regions where circulating unknown pathogens are of concern. Recombinant, neutralizing, human antibodies have never been tested as potential therapeutics in arenavirus-induced HFs, but these limitations can be overcome. No arenavirus vaccine is currently available, although vaccines against LASV and JUNV are in development. Effective diagnostic assays are absolutely essential for development and field testing arenaviral vaccines.

Antibody-based therapy to combat human viral infections. Viral antigenic variability can pose significant obstacles to the development of effective vaccines to combat human viral infections as illustrated in the cases of HIV and influenza virus. Notably, recent findings have shown that some infected individuals generate broadly neutralizing monoclonal antibodies (BNhMAbs) that target a conserved domain within the stem region of the viral surface envelope (Env) glycoprotein of HIV-1 or and are able to block infection by many phylogenetically distinct isolates. Likewise, a number of BNhMAbs have been shown to target a conserved domain within the proximal membrane stalk domain of influenza virus hemagglutinin (HA) and several BNhMAbs such as MAb F16 and MAb 5A7 proved to be protective when passively administered in mouse models of influenza virus infection. Antibodies typically exhibit desirable pharmacological characteristics including long serum half-lives, high potency, and limited off-target toxicity. Hence, the recent developments in the area of BNhMAbs have raised great interest in exploring their development as viable antiviral therapy. In addition, because BNhMAbs often recognize conserved epitopes within the region of the viral glycoproteins that mediate fusion between viral and cellular membranes, they can also facilitate the identification and structural characterization of highly conserved viral epitopes, knowledge that can be harnessed for the generation of universal vaccines and broad-spectrum antiviral drugs against these viral pathogens. As with HIV-1 and influenza, arenavirus cell entry requires a pH-dependent fusion event that is mediated by the fusogenic domain of GP2. The identification and characterization of LCMV GP-specific BNhMAbs will facilitate the development of a novel antibody-based therapy to treat LASV and LCMV induced disease in humans. In addition, this work may generate valuable information for the design of immunogens to facilitate the development of universal arenavirus vaccines, as well as broad-spectrum anti-arenaviral drugs targeting the conserved structural and functional motifs identified by BNhMAbs.

Need for the invention. The work described herein combines the use of state-of-the-art arenavirus reverse genetics with the access to a unique collection of LASV GP-specific human monoclonal antibodies (hMAbs) that have been shown to cross-react and neutralize different strains of LCMV, including isolates from human cases of LASV and LCMV induced disease, as well as WE strain that causes a LF-like disease in non-human primates. The present disclosure provides an antibody-based therapy to treat human cases of LCMV-induced disease. Unlike vaccines that depend on the host's ability to mount an effective immune response, this novel approach can provide protection in immunosuppressed individuals, including cases of LASV and LCMV infection associated with severe clinical symptoms in individuals undergoing transplantation procedures. Moreover, a detailed characterization of the conserved epitopes within LCMV GPC recognized by these BNhMAbs may help to design immunogens aimed at developing a vaccine able to confer protection against all LASV and LCMV strains that have been linked to disease in humans. In addition, information obtained from the identification and characterization of LASV BNhMAbs will help to identify broad-spectrum anti-LASV and LCMV drugs via targeting conserved epitopes identified by these BNhMAbs. The experimental approach described herein involves the use of unique reagents and assays to identify and characterize LASV and LCMV BNhMAbs and their targets.

There is an ongoing need to address LASV and LCMV infections from natural sources, as well as weaponized versions of these viruses. There also is a need for neutralizing antibodies to LASV and LCMV for diagnostic and analytical uses. The materials (e.g., antibodies and fragments thereof) and methods described herein address these needs.

SUMMARY

A single-cycle infectious, GFP-expressing, rLCMV has been generated in which the GP is replaced by GFP (rLCMVΔGP/GFP). Genetic complementation with plasmids or stable cell lines expressing arenavirus GPs of interest results in production of the corresponding GP-pseudotyped rLCMVΔGP/GFP that are used to evaluate neutralizing antibody responses to different LCMV strains using a novel GFP-based microneutralization assay. A tri-segmented LCMV platform has been developed within the backone of ARM or Cl-13 LCMV strains that allows expression of an arenavirus GP of choice and an appropriate reporter gene (e.g. fluorescent and luciferase proteins) together for facile identification of LCMV BNhMAbs and monitoring the emergence of BNhMAb LCMV escape mutants. Reverse genetics approaches have been developed that allow generation of rLCM viruses within the backbone of the immunosuppressive Cl-13 LCMV strain expressing GPs of interest that can be used to characterize the therapeutic value in vivo of these BNhMAbs. Highly specific anti-idiotypic antibodies were generated to individually detect and characterize the PK, concentration, and clearance from the circulation of each MAb used in combination therapy to enhance neutralization potency while minimizing the emergence of escape mutants. A panel of anti-idiotype antibodies (anti-ids) to 37.2D specifically detected this BNhMAb when spiked into human serum and did not capture or detect any other arenaviral BNhMAb tested to date, or any other IgG specificity present in human serum on both ELISA and SPR based studies.

Disclosed herein are compositions comprising arenavirus monoclonal antibodies (e.g., fully human monoclonal antibodies), as well as therapeutic, diagnostic, and preventative methods using the antibodies. Preventative methods include preparation of vaccines, as well as factors (e.g. small molecules, peptides) that inhibit Old World arenavirus infectivity, including LASV and LCMV. Diagnostic and therapeutic antibodies including neutralizing antibodies for the prevention and treatment of infection by LASV and other arenaviruses are also disclosed, as well as new tools and methods for the design, production, and use of arenavirus monoclonal antibodies, including expression in engineered bacterial- and mammalian-based systems.

One embodiment of the materials and methods described herein relates to monoclonal antibodies and fragments thereof effective against LASV.

Another embodiment of the materials and methods described herein relates to monoclonal antibodies or fragments thereof effective against LCMV.

Another embodiment of the materials and methods described herein relates to methods of producing forms of monoclonal antibodies effective against LASV and/or LCMV.

Another embodiment of the materials and methods described herein relates to expression vectors comprising polynucleotides encoding forms of the LASV or LCMV GP-specific hMAbs.

An embodiment of the materials and methods described herein relates to diagnostic uses of antibodies or fragments thereof, such as neutralizing antibodies, specific for LASV or LCMV.

Another embodiment of the materials and methods described herein relates to diagnostics comprising the antibodies or fragments thereof specific for LASV or LCMV, including labeled antibodies or fragments thereof of the invention.

Another embodiment of the materials and methods described herein is directed to kits comprising the antibodies of the invention.

The following non-limiting embodiments are provided to illustrate certain aspects and feature of the materials and methods described herein.

Embodiment 1 is an antigen-binding composition comprising a neutralizing antibody or neutralizing antigen-binding antibody fragment thereof specific to glycoprotein 1

(GP1), glycoprotein 2 (GP2), glycoprotein precursor (GPC), or full-length glycoprotein (GP) of Lassa virus (LASV), wherein the antibody or antibody fragment comprises a heavy chain variable region ($V_H$) and a light chain variable region ($V_L$), the $V_H$ and $V_L$ each comprising complementarity determining regions CDR1, CDR2 and CDR3 selected from the group consisting of:

(a) a $V_H$ CDR1 of SEQ ID NO: 65, a $V_H$ CDR2 of SEQ ID NO: 66, a $V_H$ CDR3 of SEQ ID NO: 67, a $V_L$ CDR1 of SEQ ID NO: 113, a $V_L$ CDR2 of sequence Gly Ala Ser, and a $V_L$ CDR3 of SEQ ID NO: 114 (from MAb 10.4B);

(b) a $V_H$ CDR1 of SEQ ID NO: 68, a $V_H$ CDR2 of SEQ ID NO: 69, a $V_H$ CDR3 of SEQ ID NO: 70, a $V_L$ CDR1 of SEQ ID NO: 115, a $V_L$ CDR2 of sequence Lys Ala Ser, and a $V_L$ CDR3 of SEQ ID NO: 116 (from MAb 19.7E);

(c) a $V_H$ CDR1 of SEQ ID NO: 71, a $V_H$ CDR2 of SEQ ID NO: 72, a $V_H$ CDR3 of SEQ ID NO: 73, a $V_L$ CDR1 of SEQ ID NO: 117, a $V_L$ CDR2 of sequence Trp Ala Ser, and a $V_L$ CDR3 of SEQ ID NO: 118 (from MAb 2.9D);

(d) a $V_H$ CDR1 of SEQ ID NO: 74, a $V_H$ CDR2 of SEQ ID NO: 75, a $V_H$ CDR3 of SEQ ID NO: 76, a $V_L$ CDR1 of SEQ ID NO: 119, a $V_L$ CDR2 of sequence Glu Val Lys, and a $V_L$ CDR3 of SEQ ID NO: 120 (from MAb 25.6A);

(e) a $V_H$ CDR1 of SEQ ID NO: 77, a $V_H$ CDR2 of SEQ ID NO: 78, a $V_H$ CDR3 of SEQ ID NO: 79, a $V_L$ CDR1 of SEQ ID NO: 121, a $V_L$ CDR2 of sequence Asp Ala Ser, and a $V_L$ CDR3 of SEQ ID NO: 122 (from MAb 36.1F);

(f) a $V_H$ CDR1 of SEQ ID NO: 80, a $V_H$ CDR2 of SEQ ID NO: 81, a $V_H$ CDR3 of SEQ ID NO: 82, a $V_L$ CDR1 of SEQ ID NO: 123, a $V_L$ CDR2 of sequence Gly Ala Ser, and a $V_L$ CDR3 of SEQ ID NO: 124 (from MAb 36.9F);

(g) a $V_H$ CDR1 of SEQ ID NO: 83, a $V_H$ CDR2 of SEQ ID NO: 84, a $V_H$ CDR3 of SEQ ID NO: 85, a $V_L$ CDR1 of SEQ ID NO: 125, a $V_L$ CDR2 of sequence Gly Ala Ser, and a $V_L$ CDR3 of SEQ ID NO: 126 (from MAb 37.2D);

(h) a $V_H$ CDR1 of SEQ ID NO: 86, a $V_H$ CDR2 of SEQ ID NO: 87, a $V_H$ CDR3 of SEQ ID NO: 88, a $V_L$ CDR1 of SEQ ID NO: 127, a $V_L$ CDR2 of sequence Gly Ala Ser, and a $V_L$ CDR3 of SEQ ID NO: 128 (from MAb 37.2G);

(i) a $V_H$ CDR1 of SEQ ID NO: 89, a $V_H$ CDR2 of SEQ ID NO: 90, a $V_H$ CDR3 of SEQ ID NO: 91, a $V_L$ CDR1 of SEQ ID NO: 129, a $V_L$ CDR2 of sequence Glu Val Arg, and a $V_L$ CDR3 of SEQ ID NO: 130 (from MAb 37.7H);

(j) a $V_H$ CDR1 of SEQ ID NO: 92, a $V_H$ CDR2 of SEQ ID NO: 93, a $V_H$ CDR3 of SEQ ID NO: 94, a $V_L$ CDR1 of SEQ ID NO: 131, a $V_L$ CDR2 of sequence Glu Val Ser, and a $V_L$ CDR3 of SEQ ID NO: 132 (from MAb 8.9F);

(k) a $V_H$ CDR1 of SEQ ID NO: 95, a $V_H$ CDR2 of SEQ ID NO: 96, a $V_H$ CDR3 of SEQ ID NO: 97, a $V_L$ CDR1 of SEQ ID NO: 133, a $V_L$ CDR2 of sequence Gly Ala Ser, and a $V_L$ CDR3 of SEQ ID NO: 134 (from MAb NE13);

(l) a $V_H$ CDR1 of SEQ ID NO: 98, a $V_H$ CDR2 of SEQ ID NO: 99, a $V_H$ CDR3 of SEQ ID NO: 100, a $V_L$ CDR1 of SEQ ID NO: 135, a $V_L$ CDR2 of sequence Gly Ala Ser, and a $V_L$ CDR3 of SEQ ID NO: 136 (from MAb 12.1F);

(m) a $V_H$ CDR1 of SEQ ID NO: 101, a $V_H$ CDR2 of SEQ ID NO: 102, a $V_H$ CDR3 of SEQ ID NO: 103, a $V_L$ CDR1 of SEQ ID NO: 137, a $V_L$ CDR2 of sequence Gln Ala Ser, and a $V_L$ CDR3 of SEQ ID NO: 138 (from MAb 9.8A);

(n) a $V_H$ CDR1 of SEQ ID NO: 104, a $V_H$ CDR2 of SEQ ID NO: 105, a $V_H$ CDR3 of SEQ ID NO: 106, a $V_L$ CDR1 of SEQ ID NO: 139, a $V_L$ CDR2 of sequence Gly Ala Ser, and a $V_L$ CDR3 of SEQ ID NO: 140 (from MAb 18.5C);

(o) a $V_H$ CDR1 of SEQ ID NO: 107, a $V_H$ CDR2 of SEQ ID NO: 108, a $V_H$ CDR3 of SEQ ID NO: 109, a $V_L$ CDR1 of SEQ ID NO: 141, a $V_L$ CDR2 of sequence Gly Ala Tyr, and a $V_L$ CDR3 of SEQ ID NO: 142 (from MAb 8.11G); and (p) a $V_H$ CDR1 of SEQ ID NO: 110, a $V_H$ CDR2 of SEQ ID NO: 111, a $V_H$ CDR3 of SEQ ID NO: 112, a $V_L$ CDR1 of SEQ ID NO: 143, a $V_L$ CDR2 of sequence Ala Ala Val, and a $V_L$ CDR3 of SEQ ID NO: 144 (from MAb 25.10C).

Embodiment 2 is the composition of Embodiment 1, wherein the composition comprises two or more of said antibodies or antigen-binding antibody fragments.

Embodiment 3 is the composition of any one of Embodiments 1 and 2, wherein the composition comprises:

(1) an antibody or antigen-binding antibody fragment comprising a $V_H$ CDR1 of SEQ ID NO: 83, a $V_H$ CDR2 of SEQ ID NO: 84, a $V_H$ CDR3 of SEQ ID NO: 85, a $V_L$ CDR1 of SEQ ID NO: 125, a $V_L$ CDR2 of sequence Gly Ala Ser, and a $V_L$ CDR3 of SEQ ID NO: 126 (from MAb 37.2D);

(2) an antibody or antigen-binding antibody fragment comprising a $V_H$ CDR1 of SEQ ID NO: 92, a $V_H$ CDR2 of SEQ ID NO: 93, a $V_H$ CDR3 of SEQ ID NO: 94, a $V_L$ CDR1 of SEQ ID NO: 131, a $V_L$ CDR2 of sequence Glu Val Ser, and a $V_L$ CDR3 of SEQ ID NO: 132 (from MAb 8.9F); and (3) an antibody or antigen-binding antibody fragment comprising a $V_H$ CDR1 of SEQ ID NO: 98, a $V_H$ CDR2 of SEQ ID NO: 99, a $V_H$ CDR3 of SEQ ID NO: 100, a $V_L$ CDR1 of SEQ ID NO: 135, a $V_L$ CDR2 of sequence Gly Ala Ser, and a $V_L$ CDR3 of SEQ ID NO: 136 (from MAb 12.1F).

Embodiment 4 is the composition of any one of Embodiments 1 to 3, wherein the antibody is selected from the group consisting of a monoclonal antibody, and a recombinantly produced antibody.

Embodiment 5 is the composition of any one of Embodiments 1 to 4, wherein the antibody comprises a human monoclonal antibody.

Embodiment 6 is the composition of any one of Embodiments 1 to 3, wherein the antigen-binding antibody fragment is selected from the group consisting of a Fab, a Fab', and a F(ab')$_2$ fragment.

Embodiment 7 is a nucleic acid (e.g., a cDNA) having a sequence that encodes for a $V_H$ of the antibody or the antibody fragment of a composition of Embodiment 1.

Embodiment 8 is the nucleic acid of Embodiment 7, wherein the nucleic acid includes a nucleic acid sequence selected from the group consisting of SEQ ID NO: 1 through SEQ ID NO: 16.

Embodiment 9 is a nucleic acid 9 e.g., a cDNA) having a sequence that encodes for a $V_L$ of the antibody or the antibody fragment of Embodiment 1.

Embodiment 10 is the nucleic acid of Embodiment 9, wherein the nucleic acid includes a nucleic acid sequence selected from the group consisting of SEQ ID NO: 17 through SEQ ID NO: 32.

Embodiment 11 is an expression vector that contains the nucleic acid sequence of any one of Embodiments 7 to 10.

Embodiment 12 is an antigen-binding composition comprising a neutralizing antibody or neutralizing antigen-binding antibody fragment thereof specific to glycoprotein 1 (GP1), glycoprotein 2 (GP2), glycoprotein precursor (GPC), or full-length glycoprotein (GP) of Lassa virus (LASV), wherein the antibody or antibody fragment comprises a heavy chain variable region ($V_H$) and a light chain variable region ($V_L$) selected from the group consisting of:

(a) a $V_H$ of SEQ ID NO: 33 and a $V_L$ of SEQ ID NO: 49 (from MAb 10.4B);

(b) a $V_H$ of SEQ ID NO: 34 and a $V_L$ of SEQ ID NO: 50 (from MAb 19.7E);

(c) a $V_H$ of SEQ ID NO: 35 and a $V_L$ of SEQ ID NO: 51 (from MAb 2.9D);

(d) a $V_H$ of SEQ ID NO: 36 and a $V_L$ of SEQ ID NO: 52 (from MAb 25.6A);

(e) a $V_H$ of SEQ ID NO: 37 and a $V_L$ of SEQ ID NO: 53 (from MAb 36.1F);

(f) a $V_H$ of SEQ ID NO: 38 and a $V_L$ of SEQ ID NO: 54 (from MAb 36.9F);

(g) a $V_H$ of SEQ ID NO: 39 and a $V_L$ of SEQ ID NO: 55 (from MAb 37.2D);

(h) a $V_H$ of SEQ ID NO: 40 and a $V_L$ of SEQ ID NO: 56 (from MAb 37.2G);

(i) a $V_H$ of SEQ ID NO: 41 and a $V_L$ of SEQ ID NO: 57 (from MAb 37.7F);

(j) a $V_H$ of SEQ ID NO: 42 and a $V_L$ of SEQ ID NO: 58 (from MAb 8.9F);

(k) a $V_H$ of SEQ ID NO: 43 and a $V_L$ of SEQ ID NO: 59 (from MAb NE13);

(l) a $V_H$ of SEQ ID NO: 44 and a $V_L$ of SEQ ID NO: 60 (from MAb 12.1F);

(m) a $V_H$ of SEQ ID NO: 45 and a $V_L$ of SEQ ID NO: 61 (from MAb 9.8A);

(n) a $V_H$ of SEQ ID NO: 46 and a $V_L$ of SEQ ID NO: 62 (from MAb 18.5C);

(o) a $V_H$ of SEQ ID NO: 47 and a $V_L$ of SEQ ID NO: 63 (from MAb 8.11G); and (p) a $V_H$ of SEQ ID NO: 48 and a $V_L$ of SEQ ID NO: 64 (from MAb 25.10C).

Embodiment 13 is the composition of Embodiment 12, wherein the composition comprises two or more of said antibodies or antigen-binding antibody fragments.

Embodiment 14 is the composition of any one of Embodiments 12 and 13, wherein the composition comprises:

(1) an antibody or antigen-binding antibody fragment comprising a $V_H$ of SEQ ID NO: 39 and a $V_L$ of SEQ ID NO: 55 (from MAb 37.2D);

(2) an antibody or antigen-binding antibody fragment comprising a $V_H$ of SEQ ID NO: 42 and a $V_L$ of SEQ ID NO: 58 (from MAb 8.9F); and (3) an antibody or antigen-binding antibody fragment comprising a $V_H$ of SEQ ID NO: 44 and a $V_L$ of SEQ ID NO: 60 (from MAb 12.1F).

Embodiment 15 is the composition of any one of Embodiments 12 to 14, wherein the the antibody is selected from the group consisting of a monoclonal antibody, and a recombinantly produced antibody.

Embodiment 16 is the composition of any one of Embodiments 12 to 15, wherein the composition comprises a human monoclonal antibody.

Embodiment 17 is the composition of any one of Embodiments 12 to 14, wherein the antigen-binding antibody fragment is selected from the group consisting of a Fab, a Fab', and a F(ab')$_2$ fragment.

Embodiment 18 is a nucleic acid (e.g., a cDNA) having a sequence that encodes for a $V_H$ of the antibody or the antibody fragment of Embodiment 12.

Embodiment 19 is a nucleic acid (e.g., a cDNA) having a sequence that encodes for a $V_L$ of the antibody or the antibody fragment of Embodiment 12.

Embodiment 20 is an expression vector that contains the nucleic acid sequence of any one of Embodiments 18 to 19.

Embodiment 21 is a vaccine for preventing or treating infection of a patient by Lassa virus or other arenaviridae comprising the antibody or antibody fragment of any one of Embodiments 1 to 6 and 12 to 17.

Embodiment 22 is the vaccine of Embodiment 21, which is cross-protective against infection by other arenaviridae.

Embodiment 23 is the vaccine of any one of Embodiments 21 to 22, which is cross-protective against infection by a lymphocytic choriomeningitis virus.

Embodiment 24 is a pharmaceutical composition for treating or preventing infection by a Lassa virus or other arenaviridae comprising the antibody or antibody fragment of any one of Embodiments 1 to 6 and 12 to 17 and a pharmaceutically acceptable carrier.

Embodiment 25 is the antibody or antibody fragment of any one of Embodiments 1 to 6 and 12 to 17 for use in treating or preventing infection by a Lassa virus or other arenaviridae.

Embodiment 26 is the antibody or antibody fragment of any one of Embodiments 1 to 6 and 12 to 17 for use in treating or preventing a lymphocytic choriomeningitis virus infection.

Embodiment 27 is use of the antibody or antibody fragment of any one of Embodiments 1 to 6 and 12 to 17 for treating or preventing infection by a Lassa virus or other arenaviridae.

Embodiment 28 is use of the antibody or antibody fragment of any one of Embodiments 1 to 6 and 12 to 17 for treating or preventing a lymphocytic choriomeningitis virus infection.

Embodiment 29 is use of the antibody or antibody fragment of any one of Embodiments 1 to 6 and 12 to 17 for the preparation of a medicament for treating or preventing infection by a Lassa virus or other arenaviridae.

Embodiment 30 is use of the antibody or antibody fragment of any one of Embodiments 1 to 6 and 12 to 17 for the preparation of a medicament for treating or preventing a lymphocytic choriomeningitis virus infection.

Embodiment 31 is diagnostic kit for detecting infection of a subject by Lassa virus or other arenaviridae comprising at least one antibody or antibody fragment of any one of Embodiments 1 to 6 and 12 to 17 bound to a detectable labelling group.

Embodiment 32 is an antibody or antibody fragment of any one of Embodiments 1 to 6 and 12 to 17 bound to a detectable labelling group.

Embodiment 33 is a method of detecting infection by a Lassa virus or other arenaviridae comprising contacting a biological sample from a subject with at least one antibody or antibody fragment of any one of Embodiments 1 to 6 and 12 to 17 bound to a detectable labelling group; and detecting a complex between the antibody or antibody fragment and a Lassa virus or other arenaviridae present in the sample.

Embodiment 34 is a method of treating or preventing infection by a Lassa virus or other arenaviridae in a subject comprising administering the antibody or antibody fragment of any one of Embodiments 1 to 6 and 12 to 17 to the subject.

Embodiment 35 is a method of treating or preventing a lymphocytic choriomeningitis virus infection in a subject comprising administering the antibody or antibody fragment of any one of Embodiments 1 to 6 and 12 to 17 to the subject.

Other embodiments and advantages of the materials and methods described herein are set forth in part in the description, which follows, and in part, may be understood by a person of ordinary skill in the art from this description, or from the practice or use of the materials and methods described herein.

DESCRIPTION OF THE FIGURES

FIG. 6 illustrates the effect of antibodies on rVSV-LASV GP infection and fusion. Antibody-mediated neutralization of (A) rVSV-LASV GP or (B) rVSV-VSV-G. The antibody 9.7A is non-neutralizing and in the same competition group as 37.7H (GPC-B); 13.4E binds to a linear epitope in the T-loop of GP2; 12.1F binds to the GP1 subunit of LASV. Error bars indicate the standard deviation of at least six (two biological replicates, each having three or more technical replicates). (C) Antibody-mediated inhibition of rVSV-LASV GP fusion at the cell surface. Error bars indicate the standard error of the mean of six (except 37.7H, where N=9). (D) Fab 37.7H reduces binding of a LAMP1-Fc fusion protein to LASV GPCysR4. Error bars indicate the standard deviation of six and three technical replicates.

FIG. 7 provides a sequence alignment prepared using CLUSTAL OMEGA™ (1.2.4) multiple sequence alignment (from EMBL-EBI, a part of the European Molecular Biology Laboratory) for the heavy chain variable region amino acid sequences, with CDRs highlighted in bold typeface: CDR1 (marked with +), CDR 2 (marked with ^), and CDR3 (marked with #). The sequences shown include 10.4B (SEQ ID NO: 33), 19.7E (SEQ ID NO: 34), 2.9D (SEQ ID NO: 35), 25.6A (SEQ ID NO: 36), 36.1F (SEQ ID NO: 37), 36.9F (SEQ ID NO: 38), 37.2D (SEQ ID NO: 39), 37.2G (SEQ ID NO: 40), 37.7H (SEQ ID NO: 41), 8.9F (SEQ ID NO: 42), NE13 (SEQ ID NO: 43), 12.1F (SEQ ID NO: 44), 9.8A (SEQ ID NO: 45), 18.5C (SEQ ID NO: 46), 8.11G (SEQ ID NO: 47), and 25.10C (SEQ ID NO: 48).

FIG. 8 provides a sequence alignment prepared using CLUSTAL OMEGA™ (1.2.4) multiple sequence alignment for the light chain variable region amino acid sequences, with CDRs highlighted in bold typeface: CDR1 (marked with +), CDR 2 (marked with ^), and CDR3 (marked with #). The sequences shown include 10.4B (SEQ ID NO: 49), 19.7E (SEQ ID NO: 50), 2.9D (SEQ ID NO: 51), 25.6A (SEQ ID NO: 52), 36.1F (SEQ ID NO: 53), 36.9F (SEQ ID NO: 54), 37.2D (SEQ ID NO: 55), 37.2G (SEQ ID NO: 56), 37.7H (SEQ ID NO: 57), 8.9F (SEQ ID NO: 58), NE13 (SEQ ID NO: 59), 12.1F (SEQ ID NO: 60), 9.8A (SEQ ID NO: 61), 18.5C (SEQ ID NO: 62), 8.11G (SEQ ID NO: 63), and 25.10C (SEQ ID NO: 64).

DETAILED DESCRIPTION

General Techniques

Figure 1:
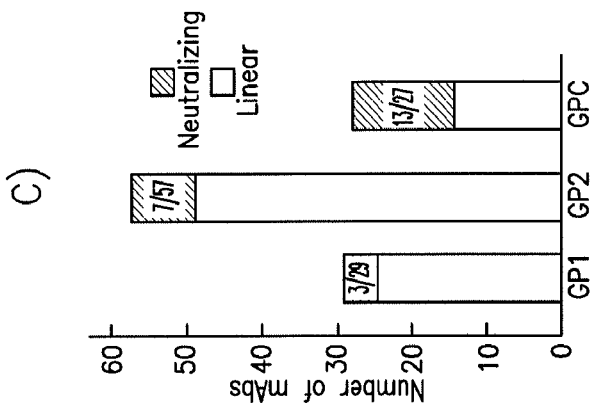
FIG. 1 depicts (A) Schematic representation of LASV GP; (B) Arenavirus GP complex; and (C) Recognition of different LASV GP species by LASV hMAbs. (A) LASV GP is synthesized as the precursor protein GPC. Signal peptidase (Spase) cleaves the small stable signal peptide (SSP) that remains associated with GP1 and GP2 to form the GP complex (FIG. 1, Panel B). The cellular protease SK1/S1P cleaves GPC into GP1 and GP2. Construct rGPe corresponds to a recombinant LASV GPC ectodomain lacking GP2 and with a non-cleavable linker replacing the SK1/S1P cleavage recognition site. Constructs expressing recombinant SSP-GP1 (rGP1) and SSP fused to GP2 (rGP2) were also generated. (B) GP-1 forms the globular head subunit that interact with the cellular receptor whereas GP2 mediates the fusion of the viral envelop with the cell membrane. SSP remains associated with both GP1 and GP2 and plays critical roles in the biology of the GP complex. (C) 293T cells were transfected with pCAGGS expressing plasmids encoding LASV rGP1, rGP2 and GPC and the reactivity of LASV hMAbs evaluated at 48 h post-transfection by immunofluorescence. The distribution of LASV GP-specific hMAbs by subunit specificity, neutralizing activity and reactivity to linear epitopes is indicated.
Figure 1:
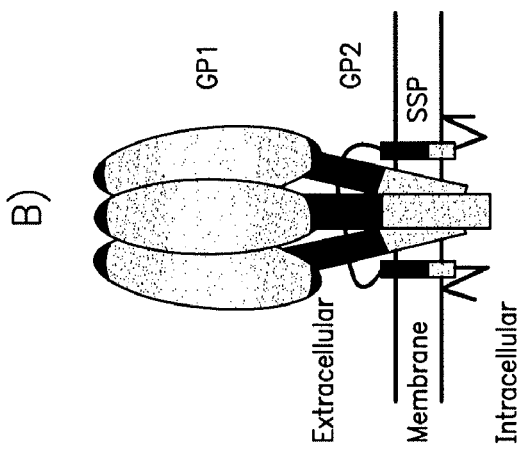
Figure 1:
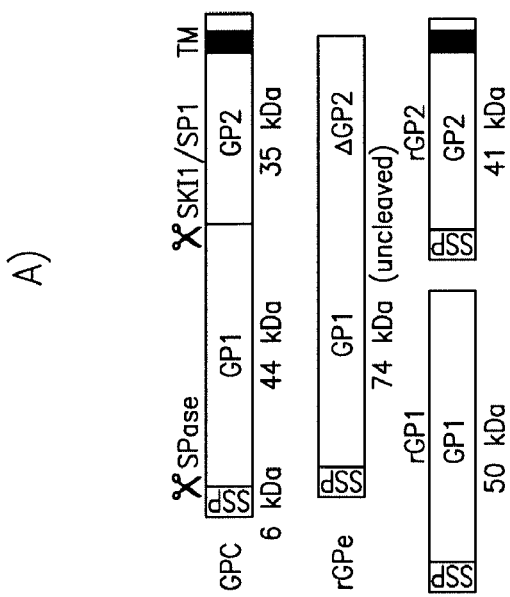

The practice of the materials and methods described herein will employ, unless otherwise indicated, conventional techniques of molecular biology (including recombinant techniques), microbiology, cell biology, biochemistry, and immunology, which are all within the normal skill of the art. Such techniques are fully explained in the literature, such as, for example, *Molecular Cloning: A Laboratory Manual*, second edition (Sambrook, et al., 1989) Cold Spring Harbor Press; *Methods in Molecular Biology*, Humana Press; *Cell Biology: A Laboratory Notebook* (I. E. Cellis, ed., 1998) Academic Press; *Animal Cell Culture* (R. I. Freshney, ed., 1987); *Introduction to Cell and Tissue Culture* (J. P. Mather and P. E. Roberts, 1998) Plenum Press; *Cell and Tissue Culture: Laboratory Procedures* (A. Doyle, J. B. Griffiths, and D. G. Newell, eds., 1993-8) J. Wiley and Sons; *Methods in Enzymology* (Academic Press, Inc.); *Handbook of Experimental Immunology* (D. M. Weir and C. C. Blackwell, eds.); *Gene Transfer Vectors for Mammalian Cells* (J. M. Miller and M. P. Cabs, eds., 1987); *Current Protocols in Molecular Biology* (F. M. Ausubel, et aL, eds., 1987); *PCR: The Polymerase Chain Reaction*, (Mullis, et al., eds., 1994); *Current Protocols in Immunology* (J. E. Coligan et al., eds., 1991); *Short Protocols in Molecular Biology* (Wiley and Sons, 1999); *Immunobiology* (C. A. Janeway and P. Travers, 1997); *Antibodies* (P. Finch, 1997); *Antibodies: a practical approach* (D. Catty., ed., IRL Press, 1988-1989); *Monoclonal antibodies: a practical approach* (P. Shepherd and C. Dean, eds., Oxford University Press, 2000); *Using antibodies: a laboratory manual* (E. Harlow and D. Lane (Cold Spring Harbor Laboratory Press, 1999); *The Antibodies* (M. Zanetti and J. D. Capra, eds., Harwood Academic Publishers, 1995).

As used herein, the singular form "a", "an", and "the" includes plural references unless indicated otherwise. For example, "a" monoclonal antibody includes one or more monoclonal antibodies.

Generally, monoclonal antibodies specific for LASV, monoclonal antibodies specific for LCMV, the polynucleotides encoding the antibodies, and methods for using these antibodies in prevention, diagnosis, detection, and treatment are described herein. Specifically, human monoclonal antibodies specific for LASV, human monoclonal antibodies specific for LCMV, and combinations thereof for development and production of diagnostics, vaccines, therapeutics, and screening tools are provided. Generally, B cell clones producing specific IgG to GP of any Lassa virus isolate or strain may be utilized to derive the antibodies described herein.

Polynucleotides

The term polynucleotide is used broadly and refers to polymeric nucleotides of any length (e.g., oligonucleotides, genes, small inhibiting RNA, fragments of polynucleotides encoding a protein, etc.). By way of example and not limitation, the polynucleotides of the invention may comprise a sequence encoding all or part of the ectodomain and part of the transmembrane domain. The polynucleotide of the invention may be, for example, linear, circular, supercoiled, single-stranded, double-stranded, branched, partially double-stranded or partially single-stranded. The nucleotides comprised within the polynucleotide may be naturally occurring nucleotides or modified nucleotides.

Functional equivalents of these polynucleotides are also intended to be encompassed by this invention. By way of example and not limitation, functionally equivalent polynucleotides are those that possess one or more of the following characteristics: the ability to generate antibodies (including, but not limited to, viral neutralizing antibodies) capable of recognizing LASV GP or the ability to generate antibodies specific to LASV GP that show neutralizing activity against LASV lineages I-IV, and proposed new lineages (e.g. lineage V from Mali, lineage VI from Togo and Benin.

Polynucleotide sequences that are functionally equivalent may also be identified by methods known in the art. A variety of sequence alignment software programs are available to facilitate determination of homology or equivalence. Non-limiting examples of these programs are BLAST family programs including BLASTN, BLASTP, BLASTX, TBLASTN, and TBLASTX (BLAST is available from the National Institutes of Health website), FASTA™, COMPARE™, DOTPLOT™, BESTFIT™, GAP™, FRAMEALIGN™, CLUSTALW™, and PILEUP™. Other similar analysis and alignment programs can be purchased from various providers such as DNA Star's MEGALIGN™, or the alignment programs in GENEJOCKEY™. Alternatively, sequence analysis and alignment programs can be accessed through the world wide web at sites such as the CMS Molecular Biology Resource at San Diego Supercomuter Center (SDSC) website; and the Swiss Institute of Bioinformatics SIB Bioinformatics Resource Portal website ExPASy Proteomics Server. Any sequence database that contains DNA or protein sequences corresponding to a gene or a segment thereof can be used for sequence analysis. Commonly employed databases include but are not limited to GenBank, EMBL, DDBJ, PDB, SWISS-PROT, EST, STS, GSS, and HTGS.

Parameters for determining the extent of homology set forth by one or more of the aforementioned alignment programs are well established in the art. They include but are not limited to p value, percent sequence identity and the percent sequence similarity. P value is the probability that the alignment is produced by chance. For a single alignment, the p value can be calculated according to Karlin et al. (1990) *Proc. Natl. Acad. Sci.* (*USA*) 87: 2246. For multiple alignments, the p value can be calculated using a heuristic approach such as the one programmed in BLAST. Percent sequence identify is defined by the ratio of the number of nucleotide or amino acid matches between the query sequence and the known sequence when the two are optimally aligned. The percent sequence similarity is calculated in the same way as percent identity except one scores amino acids that are different but similar as positive when calculating the percent similarity. Thus, conservative changes that occur frequently without altering function, such as a change from one basic amino acid to another or a change from one hydrophobic amino acid to another are scored as if they were identical.

The term "analog" includes any polypeptide having an amino acid residue sequence substantially identical to a polypeptide of the invention in which one or more residues have been conservatively substituted with a functionally similar residue and which displays the functional aspects of the polypeptides as described herein. Examples of conservative substitutions include the substitution of one non-polar (hydrophobic) residue such as isoleucine, valine, leucine or methionine for another; the substitution of one polar (hydrophilic) residue for another such as between arginine and lysine, between glutamine and asparagine, between glycine and serine; the substitution of one basic residue such as lysine, arginine or histidine for another; and the substitution of one acidic residue, such as aspartic acid or glutamic acid or another.

The phrase "conservative substitution" also includes the use of a chemically derivatized residue in place of a non-derivatized residue. "Chemical derivative" refers to a subject polypeptide having one or more amino acid residues chemically derivatized by reaction of a functional side group. Examples of such derivatized amino acids include for example, those amino acids in which free amino groups have been derivatized to form amine hydrochlorides, p-toluene sulfonyl groups, carbobenzoxy groups, t-butyloxycarbonyl groups, chloroacetyl groups or formyl groups. Also, the free carboxyl groups of amino acids may be derivatized to form salts, methyl and ethyl esters or other types of esters or hydrazides. Also, the free hydroxyl groups of certain amino acids may be derivatized to form 0-acyl or 0-alkyl derivatives. Also, the imidazole nitrogen of histidine may be derivatized to form N-imbenzylhistidine. Also included as chemical derivatives are those proteins or peptides which contain one or more naturally occurring amino acid derivatives of the twenty standard amino acids. For example, 4-hydroxyproline may be substituted for proline, 5-hydroxylysine may be substituted for lysine, 3-methylhistidine may be substituted for histidine, homoserine may be substituted for serine, and ornithine may be substituted for lysine. Polypeptides of the present invention also include any polypeptide having one or more additions and/or deletions of residues relative to the sequence of any one of the polypeptides whose sequence is described herein.

Two polynucleotide or polypeptide sequences are said to be "identical" if the sequence of nucleotides or amino acids in the two sequences is the same when aligned for maximum correspondence as described below. Comparisons between two sequences are typically performed by comparing the sequences over a comparison window to identify and compare local regions of sequence similarity. A "comparison window" as used herein, refers to a segment of at least about 20 contiguous positions, usually 30 to about 75 contiguous positions, or 40 to about 50 contiguous positions, in which a sequence may be compared to a reference sequence of the same number of contiguous positions after the two sequences are optimally aligned.

Optimal alignment of sequences for comparison may be conducted using the MEGALIGN™ program in the LASERGENE™ suite of bioinformatics software (DNASTAR, Inc., Madison, Wis.), using default parameters. This program embodies several alignment schemes described in the following references: Dayhoff, M. O. (1978) "A model of evolutionary change in proteins—Matrices for detecting distant relationships" in Dayhoff, M. O. (ed.) *Atlas of Protein Sequence and Structure*, National Biomedical Research Foundation, Washington D.C. Vol. 5, Suppl. 3, pp. 345-358 (1978); Hem J., "Unified Approach to Alignment and Phylogenes" pp. 626-645 *Methods in Enzymology* vol. 183, Academic Press, Inc., San Diego, Calif. (1990); Higgins, D. G. and Sharp, P. M., 1989, *CABIOS* 5:151-153; Myers, E. W. and Muller W., 1988, *CABIOS* 4:11-17; Robinson, E. D., 1971, *Comb. Theor.* 11:105; Santou, N., Nes, M., 1987, *Mol. Biol. Evol.* 4:406-425; Sneath, P. H. A. and Sokal, R. R., 1973, *Numerical Taxonomy the Principles and Practice of Numerical Taxonomy*, Freeman Press, San Francisco, Calif.; Wilbur, W. J. and Lipman, D. J., 1983, *Proc. Natl. Acad. Sci. USA* 80:726-730.

Preferably, the "percentage of sequence identity" is determined by comparing two optimally aligned sequences over a window of comparison of at least 20 positions, wherein the portion of the polypeptide sequence in the comparison window may comprise additions or deletions (i.e., gaps) of 20 percent or less, usually 5 to 15 percent, or 10 to 12 percent, as compared to the reference sequence (which does not comprise additions or deletions) for optimal alignment of the two sequences. The percentage is calculated by determining the number of positions at which the identical amino acid residue occurs in both sequences to yield the number of matched positions, dividing the number of matched positions by the total number of positions in the reference sequence (i.e., the window size) and multiplying the results by 100 to yield the percentage of sequence identity.

Expression Vectors

Expression vectors comprising at least one polynucleotide encoding an antibody or antibody fragment protein also are described herein. Expression vectors are well known in the art and include, but are not limited to viral vectors or plasmids. Viral-based vectors for delivery of a desired polynucleotide and expression in a desired cell are well known in the art. Exemplary viral-based vehicles include, but are not limited to, recombinant retroviruses (see, e.g., PCT Publication Nos. WO 90/07936; WO 94/03622; WO 93/25698; WO 93/25234; WO 93/11230; WO 93/10218; WO 91/02805; U.S. Pat. Nos. 5,219,740 and 4,777,127), alphavirus-based vectors (e.g., Sindbis virus vectors, Semliki forest virus), Ross River virus, adeno-associated virus (AAV) vectors (see, e.g., PCT Publication Nos. WO 94/12649, WO 93/03769; WO 93/19191; WO 94/28938; WO 95/11984 and WO 95/00655), vaccinia virus (e.g., Modified Vaccinia virus Ankara (MVA) or fowlpox), Baculovirus recombinant system and herpes virus.

Nonviral vectors, such as plasmids, are also well known in the art and include, but are not limited to, yeast- and bacteria-based plasmids.

Methods of introducing the vectors into a host cell and isolating and purifying the expressed protein are also well known in the art (e.g., *Molecular Cloning: A Laboratory Manual*, second edition, Sambrook, et al., 1989, Cold Spring Harbor Press). Examples of host cells include, but are not limited to, mammalian cells such as NS0 and CHO cells.

By way of example, vectors comprising the polynucleotides described herein may further comprise a tag polynucleotide sequence to facilitate protein isolation and/or purification. Examples of tags include but are not limited to the myc-epitope, S-tag, his-tag, HSV epitope, V5-epitope, FLAG and CBP (calmodulin binding protein). Such tags are commercially available or readily made by methods known to the art.

The vector may further comprise a polynucleotide sequence encoding a linker sequence. Generally, the linking sequence is positioned in the vector between the antibody polynucleotide sequence and the polynucleotide tag sequence. Linking sequences can encode random amino acids or can contain functional sites. Examples of linking sequences containing functional sites include but are not limited to, sequences containing the Factor Xa cleavage site, the thrombin cleavage site, or the enterokinase cleavage site.

By way of example, and not limitation, an antibody specific for LASV may be generated as described herein using mammalian expression vectors in mammalian cell culture systems or bacterial expression vectors in bacterial culture systems. By way of example, and not limitation, an antibody specific for LCMV may be generated as described herein using mammalian expression vectors in mammalian cell culture systems or bacterial expression vectors in bacterial culture systems.

Antibodies

Examples of antibodies disclosed herein, include, but are not limited to, antibodies specific for LASV or LCMV, antibodies that cross react with native Lassa virus antigens and/or native lymphocytic choriomeningitis virus antigens, and neutralizing antibodies. By way of example, a characteristic of a neutralizing antibody includes the ability to block or prevent infection of a host cell. The antibodies may be characterized using methods well known in the art.

The antibodies useful in the compositions and methods described herein can encompass monoclonal antibodies, polyclonal antibodies, antibody fragments (e.g., Fab, Fab', F(ab')2, Fv, Fc, etc.), chimeric antibodies, bi-specific antibodies, heteroconjugate antibodies, single-chain fragments (e.g. ScFv), mutants thereof, fusion proteins comprising an antibody portion, humanized antibodies, and any other modified configuration of the immunoglobulin molecule that comprises an antigen recognition site of the required specificity, including glycosylation variants of antibodies, amino acid sequence variants of antibodies, and covalently modified antibodies. The antibodies may be murine, rat, human, or of any other origin (including chimeric or humanized antibodies).

Methods of preparing monoclonal and polyclonal antibodies are well known in the art. Polyclonal antibodies can be raised in a mammal, for example, by one or more injections of an immunizing agent and, if desired an adjuvant. Examples of adjuvants include, but are not limited to, keyhole limpet hemocyanin (KLH), serum albumin, bovine thryoglobulin, soybean trypsin inhibitor, complete Freund adjuvant (CFA), and MPL-TDM adjuvant. The immunization protocol can be determined by one of skill in the art.

The antibodies may alternatively be monoclonal antibodies. Monoclonal antibodies may be produced using hybridoma methods (see, e.g., Kohler, B. and Milstein, C. (1975) *Nature* 256:495-497 or as modified by Buck, D. W., et al., *In Vitro*, 18:377-381(1982).

If desired, the antibody of interest may be sequenced and the polynucleotide sequence may then be cloned into a vector for expression or propagation. The sequence encoding the antibody of interest may be maintained in the vector in a host cell, and the host cell can then be expanded and frozen for future use. In an alternative embodiment, the polynucleotide sequence may be used for genetic manipulation to "humanize" the antibody or to improve the affinity, or other characteristics of the antibody (e.g., genetically manipulate the antibody sequence to obtain greater affinity to LASV and/or LCMV glycoprotein and/or greater efficacy in inhibiting the fusion of LASV and/or LCMV to the host cell).

The antibodies may also be humanized by methods known in the art (See, for example, U.S. Pat. Nos. 4,816, 567; 5,807,715; 5,866,692; 6,331,415; 5,530,101; 5,693, 761; 5,693,762; 5,585,089; and 6,180,370). In yet another alternative, human antibodies may be obtained by using mice that have been engineered to express specific human immunoglobulin proteins.

In another alternative embodiment, antibodies may be made recombinantly and expressed using any method known in the art. By way of example, antibodies may be made recombinantly by phage display technology. See, for example, U.S. Pat. Nos. 5,565,332; 5,580,717; 5,733,743; and 6,265,150; and Winter et at., *Annu. Rev. Immunol.* 12:433-455 (1994). Alternatively, phage display technology (McCafferty et al., *Nature* 348:552-553 (1990)) can be used to produce human antibodies and antibody fragments in vitro. Phage display can be performed in a variety of formats; for review, see Johnson, Kevin S. and Chiswell, David J., *Current Opinion in Structural Biology* 3:564-571 (1993). By way of example, LASV and/or LCMV glycoprotein as described herein may be used as an antigen for the purposes of isolating recombinant antibodies by these techniques.

Antibodies may be made recombinantly by first isolating the antibodies and antibody producing cells from host animals, obtaining the gene sequence, and using the gene sequence to express the antibody recombinantly in host cells (e.g., CHO cells). Another method that may be employed is to express the antibody sequence in plants (e.g., tobacco) or transgenic milk. Methods for expressing antibodies recombinantly in plants or milk have been disclosed. See, for example, Peeters, et al. *Vaccine* 19:2756 (2001); Lonberg, N. and D. Huszar *Int. Rev. Immunol* 13:65 (1995); and Pollock, et al., *J. Immunol. Methods* 231:147 (1999). Methods for making derivatives of antibodies (e.g. humanized and single-chain antibodies, etc.) are known in the art.

The antibodies described herein can be bound to a carrier by conventional methods for use in, for example, isolating or purifying LASV and/or LCMV glycoprotein or detecting LASV and/or LCMV glycoproteins, antigens, or particles in a biological sample or specimen. Alternatively, by way of example, the neutralizing antibodies of the invention may be administered as a therapeutic treatment to a subject infected with or suspected of being infected with LASV or LCMV. A "subject," includes but is not limited to humans, simians, farm animals, sport animals, and pets. Veterinary uses are also encompassed by methods described herein. For diagnostic purposes, the antibodies can be labeled, e.g., bound to a detectable labelling group such as a fluorescent dye (e.g., a ALEXA FLUOR® dye), a quantum dot label (e.g., a QDOT® label), R-phycoerythrin, streptavidin, biotin, an enzyme (e.g., Glucose Oxidase, Horseradish Peroxidase or Alkaline Phosphatase), a radioiosotope (e.g., iodine-125, indium-111), and the like. Such labelling techniques are well known in the antibody art.

Antibody DNA Sequences

Sixteen neutralizing antibodies against LASV were identified, which are designated herein as 10.4B, 19.7E, 2.9D, 25.6A, 36.1F, 36.9F, 37.2D, 37.2G, 37.7H, 8.9F, NE13, 12.1F, 9.8A, 18.5C, 8.11G, and 25.10C. Nucleotide sequences (cDNA) encoding portions of heavy chain (HC) and light chain (LC) of each antibody are shown below. The illustrated nucleotide sequences encode portions of the HC and LC encompassing the variable regions thereof, i.e., the $V_H$ and $V_L$ regions, respectively, along with portions of vector sequences.

```
(10.4B V_H)
                                                                  SEQ ID NO: 1
        tgcgcgttac ngatccaagc tgtgaccggc gcctacctga gatcaccggt gctagcacca      60
tggagacaga cacactcctg ctatgggtac tgctgctctg ggttccaggt tccactggtg     120
accaggtgca gctggtacag tctggggagg gcgtggtcca gcctgggagg tccctgagag     180
tctcctgtgt tacgtctgga ttcaatttca gagcctacgg catgcactgg gtccgccaga     240
ttccaggcaa gggactggag tgggtggcag atatttggtc tgccgagact aatagacact     300
atgcagattc cgtgaagggc cgattcacca tctccagaga caactccaag agcacactgt     360
atctgcaaat gaacagcctg agagccgagg acacgggcgt atatttctgt gccaaagcgc     420
gaccaggcta tgattatgtc gttgacttat ggggccaggg aacgctggtc atcgtctcct     480
cagcttccac caagggccca tcggtcttcc cctggcgcc ctgctccagg agcacctctg       540
ggggcacagc ggccctgggc tgcctggtca aggactactt ccccgaaccg gtgacggtgt     600
cgtggaactc aggcgccctg accagcggcg tgcacacctt cccggctgtc ctacagtcct     660
caggactcta                                                            670

(19.7E V_H)
                                                                  SEQ ID NO: 2
        atccagctgt gaccggcgcc tacctgagat caccggtgct agcaccatgg agacagacac       60
actcctgcta tgggtactgc tgctctgggt tccaggttcc actggtgacg aggtgcagct     120
```

-continued

| | |
|---|---|
| ggtggagtct gggggaggct tagttcggcc tgggggtcc ctgagactct cctgtgcagc | 180 |
| ctctggattc tccttcagta gctactcgat gcactgggtc cgccatgttc ctgggaaggg | 240 |
| gctggtgtgg gtctcatata ttaatagtga tgggagtact aaaatctacg cggactccgt | 300 |
| gaagggccga ttctccatct ccagagacaa tgccaagaac aagctctatc tgcaaatgga | 360 |
| cagtttgaga gtcgaggaca cggctgtata ttcgtgtgta aggcttgtac attacgactg | 420 |
| gtccccattc gtgtggggcc agggaaccct ggtcaccgtc tcctcagcct ccaccaaggg | 480 |
| cccatcggtc ttccccctgg caccctcctc aagagcacc tctggggca gcggccct | 540 |
| gggctgcctg gtcaaggact acttccccga accggtgacg gtgtcgtgga actcaggcgc | 600 |
| cctgaccagc ggcgtgcaca ccttcccggc tgtcctacag tcctcaggac tctactccct | 660 |
| cagcagcgtg gtgaccgtgc cctccagcag cttgggcacc cagacctaca tctgcaacgt | 720 |
| gaatcacaag cccagcaaca ccaaggtgga caagaaagtt gagcccaat cttgtgacaa | 780 |
| aactcacaca tgcccaccgt gcccagcacc tgaactcct | 819 |

(2.9D V<sub>H</sub>)

SEQ ID NO: 3

| | |
|---|---|
| gtcactgcac ctcggttcta tcgattggct agcaccatgg agacagacac actcctgcta | 60 |
| tgggtactgc tgctctgggt tccaggttcc actggtgacg aggtgcagct ggtggagtct | 120 |
| ggggaggcc tggtcaagcc tgggggtcc cttagactct cctgtgcagc ctctggattc | 180 |
| accttcacta gatttacttt gacctgggtc cgccaggctc cagggaaggg gctggagtgg | 240 |
| gtctcatcca ttagtagtgg gagtagtgac ataaactacg cagactcagt gaagggccga | 300 |
| ttcaccatat ccagagacaa cgccaggaac tccctgttcc tgcaaatgag cagcctgaga | 360 |
| gtcgacgaca cggctgtgta ttactgtgcg aaagatcccc ggtcggggat ctctggtcgc | 420 |
| tacgggatgg acgtctgggg ccaagggacc acggtcatcg tctcctcagc ttccaccaag | 480 |
| ggcccatcgg tcttccccct ggcgccctgc tccaggagca cctctggggg cacagcggcc | 540 |
| ctgggctgcc tggtcaagga ctacttcccc gaaccggtga cggtgtcgtg gaactcaggc | 600 |
| gccctgacca gcggcgtgca caccttcccg gctgtcctac agtcctcagg actctactcc | 660 |
| ctcagcagcg tggtgaccgt gccctccagc agcttgggca cccagaccta catctgcaac | 720 |
| gtgaatcaca agcccagcaa caccaaggtg gacaagagag ttgagcccaa atcttgtgac | 780 |
| aaaactcaca catgcccacc gtgcccagca cctgaactcc tggggggacc gtcagtcttc | 840 |
| ctcttccccc caaaacccaa ggacaccctc atgatctccc ggacccctga ggtcacatgc | 900 |
| gtggtggtgg acgtgagcca | 920 |

(25.6A V<sub>H</sub>)

SEQ ID NO: 4

| | |
|---|---|
| acctcggttc ttcgattggc tagcaccatg gagacagaca cactcctgct atgggtactg | 60 |
| ctgctctggg ttccaggttc cactggtgac caggtgcagc tgcaggagtc aggaggaggc | 120 |
| ctggtcaagg ctgggggtc cctgagactc tcctgtgcag cctctggatt catgttcgag | 180 |
| agatatagcc ttcactgggt ccgtcagact ccaggcaagg gctggagtg gtctcatcc | 240 |
| attagtagtc ttagtggcag tcacataaac tacgcagact cagtgaaggg ccgattcacc | 300 |
| atctccagag acaacgccaa gaattcactg tctctgcaaa tgaacagcct gagagtcgaa | 360 |
| gacacggcta tatattattg tgcgagagat cgacgttcgg ggagttcccc cgtccccttg | 420 |
| gacgtctggg gccaagggac cacggtcacc gtctcctctg cctccaccaa gggcccatcg | 480 |
| gtcttccccc tggcaccctc ctccaagagc acctctgggg gcacagcggc cctgggctgc | 540 |

-continued (36.1F V_H)

SEQ ID NO: 5

```
gtcactgccc tcggttctat cgattggcta gcaccatgga gacagacaca ctcctgctat    60
gggtactgct gctctgggtt ccaggttcca ctggtgacca ggtgcagctg caggagtcgg   120
gcgcgggact ggtgaagcct tcggagaccc tgtccctcac ctgcgctgtc tcaggtggac   180
ccttcagcgg tgcctactgg acgtggatcc gccaaactcc agggaagggg ctggagtgga   240
ttggagaggc cggtcggagt ggaaccacca actacaatcc gtccctcaag agtcgagtca   300
ccatatcact ggacacgtcc aagagccagt ttccctgaa gctgacttcc gtgaccgccg    360
cggacacggc tgtttacttc tgtgggagac gccaaataat gtctttgagt aatctttata   420
agagacccgt tgactcttgg ggccggggaa ccccggtcat cgtctcctca gcctccacca   480
agggcccatc ggtcttcccc ctggcaccct cctccaagag cacctctggg gcacagcgg    540
ccctgggctg cctggtcaag gactacttcc ccgaaccggt gacggtgtcg tggaactcag   600
gcgccctgac cagcggcgtg cacaccttcc cggctgtcct acagtcctca ggactctact   660
ccctcagcag cgtggtgacc gtgccctcca gcagcttggg cacccagacc tacatctgca   720
acgtgaatca caagcccagc aacaccaagg tggacaagag agttgagccc aaatcttgtg   780
acaaaactca cacatgccca ccgtgcccag cacctgaact cctgggggga ccgtcagtct   840
tcctcttccc cccaa                                                    855
```

(36.9F V_H)

SEQ ID NO: 6

```
gtcactgccc tcggttctat cgattggcta gcaccatgga gacagacaca ctcctgctat    60
gggtactgct gctctgggtt ccaggttcca ctggtgacga ggtgcagctg gtgcagtctg   120
gaggaggcct ggtcaaggcg ggggggtccc tgaaactctc ctgtggagcc tctggattca   180
ccttcagtag ttatagcatg agctgggtcc gccaggctcc agggaagggg ctggagtggg   240
tctcatacat tagtagtggt gggagttcta tacactacgc agactcagtg aagggccgat   300
tcaccatctc cagagacaac gccaagaatt cactgtatct gcaaatgaag aacctgaggg   360
tcgacgacac gggtcggtat tattgtgtga gagatccccg atcggggatc tctggtcggt   420
acggtatgga cgtctggggt caagggacca cggtcaccgt ctcctcagcc tccaccaagg   480
gcccatcggt cttccccctg gcaccctcct ccaagagcac ctctggggc acagcggccc    540
tgggctgcct ggtcaaggac tacttccccg aaccggtgac ggtgtcgtgg aactcaggcg   600
ccctgaccag cggcgtgcac accttcccgg ctgtcctaca gtcctcagga ctctactccc   660
tcagcagcgt ggtgaccgtg ccctccagca gcttgggcac ccagacctac atctgcaacg   720
tgaatcacaa gcccagcaac accaaggtgg acaagagagt tgagcccaaa tcttgtgaca   780
aaactcacac atgcccaccg tgcccagcac ctgaactcct gggggaccg tcagtcttcc    840
tcttcccccc aaacccaagg acaccctcat gatc                               874
```

(37.2D V_H)

SEQ ID NO: 7

```
tcactgccct cggttctatc gattggctag caccatggag acagacacac tcctgctatg    60
ggtactgctg ctctgggttc caggttccac tggtgacgaa gtgcagctgg tgcagtctgg   120
agctgaggtg aagaagcctg ggcttcagt gaaggtgtcc tgcaaggcct ctggttacac    180
ctttacgaaa tacggaatca gctgggtgcg acaggcccct ggacaagggc ttgagtggat   240
gggatggatc agcgcgttta atggttacac aaggtatggt cagagattcc agggcaaagt   300
caccatgacc acagacacat ccacgaacac agcctctttg gaggtgagga ccctgacatc   360
taacgacacg gccgtctatt actgtgcgag acaatatccc gaccaatata gtagcagcgg   420
```

```
ttggccccgc ctcttcgcca tggacgtctg gggccaaggg accacggtca tcgtctcccc      480
agcctccacc aagggcccat cggtcttccc cctggcaccc tcctccaaga gcacctctgg      540
gggcacagcg ccctgggct gcctggtcaa ggactacttc cccgaaccgg tgacggtgtc       600
gtggaactca ggcgccctga ccagcggcgt gcacaccttc ccggctgtcc tacagtcctc      660
aggactctac tccctcagca gcgtggtgac cgtgccctcc agcagcttgg gcacccagac      720
ctacatctgc aacgtgaatc acaagcccag caacaccaag gtggacaaga gagttgagcc      780
caaatcttgt gacaaaactc acacatgccc accgtgccca gcacctgaac tcctgggggg      840
accgtcagtc ttcctcttc                                                   859

(37.2G V_H)
                                                          SEQ ID NO: 8
tcactgccct cggttctatc gattggctag caccatggag acagacacac tcctgctatg       60
ggtactgctg ctctgggttc caggttccac tggtgacgag gtgcagctgg tggagtctgg      120
gggaggcctg gtcaagccgg gggggtcccg agactctcc tgtgctgcct ctggattcac       180
cttcagtaga gataccatga cctgggtccg ccaggctcca gggaaggggc tggagtgggt      240
cgcatccata agtagtggta gcagtgacat aaactacgca gactcagtga agggccgatt      300
caccatctcc agagacaacg caagaactc actgtatctg cacatgaaca gcctgagagc       360
cgacgacacg gctatatatt actgtgcgag agatccccgg tcgggaatct ctggtcggta      420
tggtatggac gtctggggcc aagggaccac ggtcaccgtc tcctcagcct ccaccaaggg      480
cccatcggtc ttccccctgg caccctcctc aagagcacc tctgggggca gcggccct        540 gggctgcctg gtcaaggact acttccccga accggtgacg gtgtcgtgga actcaggcgc      600
cctgaccagc ggcgtgcaca ccttcccggc tgtcctacag tcctcaggac tctactccct      660
cagcagcgtg gtgaccgtgc cctccagcag cttgggcacc cagacctaca tctgcaacgt      720
gaatcacaag cccagcaaca ccaaggtgga caagagagtt gagcccaaat cttgtgacaa      780
aactcacaca tgcccaccgt gcccagcacc tgaactcctg ggggaccgt cagtcttcct       840 cttcccccca aaacccaagg acaccctcat gatctcccgg acccctgagg tcacatgcgt      900
ggtggtggac gtgagccacg aagaccctga ggtcaagttc aactggtacg tggacggcgt      960

(37.7H V_H)
                                                          SEQ ID NO: 9
gtcactgcac ctcggttcta tcgattggct agcaccatgg agacagacac actcctgcta       60
tgggtactgc tgctctgggt tccaggttcc actggtgacg aggtgcagct ggtgcagtct      120
ggaggaggcc tggtcaaggc ggggggtcc ctgaggctct cctgtgcagc ctccggattc       180
acattcagca cctacagtat gaactggatc cgccaggctc agggaaggg gctggagtgg      240 gtcgcttcca ttagtagtcg aagtggcagt cacataaact acgtagactc agtgaaggga      300
cgattcacca tctccagaga caacgccagg gacttattgt atctgcaaat gaacagcctg      360
agagtcgacg actcggctct ctattactgt gcgagagatc gccgttcggg gacttctccc      420
ctccccttgg acgtctgggg ccaagggacc acggtcaccg tcttctcagc ctccaccaag      480
ggcccatcgg tcttccccct ggcaccctcc tccaagagca cctctggggg cacagcggcc      540
ctgggctgcc tggtcaagga ctacttcccc gaaccggtga cggtgtcgtg gaactcaggc      600
gccctgacca gcggcgtgca caccttcccg gctgtcctac agtcctcagg actctactcc      660
ctcagcagcg tggtgaccgt gccctccagc agcttgggca cccagaccta catctgcaac      720
gtgaatcaca agcccagcaa caccaaggtg gacaagagag ttgagcccaa atcttgtgac      780
aaaactcaca catgcccacc gtgcccagca cctgaactcc tggggggacc gtcagtcttc      840
```

-continued

```
ctcttccccc caaaacccaa ggacaccctc atgatctccc ggaccnctga ggtcacatgc      900
gtggtggtgg acgtgagcca cgaa                                            924
```

(8.9F V<sub>H</sub>)

SEQ ID NO: 10
```
cctcggttct atcgattggc tagcaccatg gagacagaca cactcctgct atgggtactg      60
ctgctctggg ttccaggttc cactggtgac cagggcacct tgagggagtc tggtccagga     120
ctggtgaggc cttcggagac cctgtccctc acctgcggtg tctctggtta ttccatcagt     180
agtggttact actggggctg gatccggcag ccccagggaa aggggctgga gtggattggg     240
aatatctatc gtagtgggag cacctactac aacccgtccc tcaagagtcg agtcaccgtc     300
tcaatagaca cgtccaaaaa ccagttctcc ctgaagttga attctgtgac cgccgcagac     360
acggccgtgt attactgtgc gagatcgggt ataaaagtgg ctgacgacta ttactacgaa     420
atggacgtct ggggccaagg gaccgacgac tactcttacg ctatggacgt ctggggccaa     480
gggaccacgg tcaccgtctc ctcagcctcc accaagggcc catcggtctt ccccctggca     540
ccctcctcca agagcacctc tgggggcaca gcggccctgg gctgcctggt caaggactac     600
ttccccgaac cggtgacggt gtcgtggaac tcaggcgccc tgaccagcgg cgtgcacacc     660
ttcccggctg tcctacagtc ctcaggactc tactccctca gcagcgtggt gaccgtgccc     720
tccagcagct tgggcaccca gacctacatc tgcaacgtga atcacaagcc cagcaacacc     780
aaggtggaca gagagttga gcccaaatct tgtgacaaaa ctcacacatg cccaccgtgc     840
ccagcacctg aactcctggg gggaccgtca gtcttcctct ccccccaaa cccaaggac      900
accctcatga t                                                          911
```

(NE13 V<sub>H</sub>)

SEQ ID NO: 11
```
actgcacctc ggttctatcg attggctagc accatggaga cagacacact cctgctatgg      60
gtactgctgc tctgggttcc aggttccact ggtgacgagg ttcagctggt ggagtctggg     120
ggaggcctgg tcaagcctgg ggggtccctg agactctcct gtgtagcctc tggattcacc     180
ttcagttcct atagcatgaa ctgggtccgc caggctccag gaaggggct ggagtgggtc     240
tcatccatta gtagtggtag tagttacata gagtacgcag actcagtgaa gggccgactc     300
accatctcca gagacaacgc caagaagtca ctgtatctgc aactgaacag cctgagagcc     360
gaggacacgg ctgtgtatta ctgtgcgaga cacacagctc gaatcgactc ttaccacggt     420
atggacgtct ggggccaagg gaccacagtc accgtctcct cagcctccac caagggccca     480
tcggtcttcc ccctggcacc ctcctccaag agcacctctg ggggcacagc ggccctgggc     540
tgcctggtca aggactactt ccccgaaccg gtgacggtgt cgtggaactc aggcgccctg     600
accagcggcg tgcacacctt cccggctgtc ctacagtcct caggactcta ctccctcagc     660
agcgtggtga ccgtgccctc agcagcttg gcacccaga cctacatctg caacgtgaat     720
cacaagccca gcaacaccaa ggtggacaag agagttgagc ccaaatcttg tgacaaaact     780
cacacatgcc caccgtgccc agcacctgaa ctcctggggg gaccgtcagt cttcctcttc     840
cccccaaaac ccaaggacac cctcatgatc tcccggaccc c                         881
```

(12.1F V<sub>H</sub>)

SEQ ID NO: 12
```
gtcactgcac ctcggttcta tcgattggct agcaccatgg agacagacac actcctgcta      60
tgggtactgc tgctctgggt tccaggttcc actggtgacc aggtgcagct gcaggagtcg     120
ggcgcaggac tgttgaagcc ttcggagacc ctgtccctca gttgcactgt cgatggtgag     180
tccttcaatg gtttcttctg gacgtggatc cgccagcccc cagggaaggg tctggagtgg     240
```

-continued

```
attggagaaa tcaatcatct tgcaagcacc ggctacaacc cgtccctcaa gagtcgagtc      300
accatttcag tagacacgtc caagaaccag ttctctttga agttgacctc tgtgaccgcc      360
gcggacacgg ctgtgtatta ctgtgcgaga ggatacagct atggttttgc atggcccaac      420
taccactatt tggacgtctg gggcaaaggg accacggtca ccgtctcctc agcctccacc      480
aagggcccat cggtcttccc cctggcaccc tcctccaaga gcacctctgg gggcacagcg      540
gccctgggct gcctggtcaa ggactacttc cccgaaccgg tgacggtgtc gtggaactca      600
ggcgccctga ccagcggcgt gcacaccttc ccggctgtcc tacagtcctc aggactctac      660
tccctcagca gcgtggtgac cgtgccctcc agcagcttgg gcacccagac ctacatctgc      720
aacgtgaatc acaagcccag caacaccaag gtggacaaga gagttgagcc caaatcttgt      780
gacaaaactc acacatgccc accgtgccca gcacctgaac tcctgggggg accgtcagtc      840
ttcctcttnc ccccaaaacc caaggacacc ctcatgatct cccggacccc tgaggtcaca      900
tgcgtggtgg tggacgtgag c                                                921
```

(9.8A V$_H$)

SEQ ID NO: 13
```
ttctatcgat ttggctagca ccatggagac 9.8A agacacactc ctgctatggg tactgctgct       60
ctgggttcca ggttccactg gtgacgaggt gcagctggtg cagtctggag gacgcttggt      120
acagcctggg gggtccctga gactctcctg tgtagcctct ggattcacct ttagcagcca      180
tgccatgagc tgggtccgcc aggctccagg gaagggctg gagtgggtct caggttttag       240
tggtagtagt ggtaccacaa gtacgcagag ctccgtgaag gccggttca ccatctccag       300 agacaattcc aagaaaacgc tgtatctgca aatgaacagc ctgagagccg aggacacggc      360
cgtatattac tgtgcgaaag gcttctcccc atttcgggga gtacaattcc ctactttga      420 ctactggggc cagggaacgc tggtcaccgt ctcctcagcc tccaccaagg gcccatcggt      480
cttccccctg gcaccctcct ccaagagcac ctctgggggc acagcggccc tgggctgcct     540
ggtcaaggac tacttccccg aaccggtgac ggtgtcgtgg aactcaggcg ccctgaccag      600
cggcgtgcac accttccggg ctgtcctaca gtcctcagga ctctactccc tcagcagcgt      660
ggtgaccgtg ccctccagca gcttgggcac ccagacctac atctgcaacg tgaatcacaa      720
gcccagcaac accaaggtgg acaagagagt tgagcccaaa tcttgtgaca aaactcacac      780
atgcccaccg tgcccagcac ctgaactcct ggggggaccg tcagtcttcc tcttcccccc      840
aaaacccagg acaccctcat gatctcccgg accc                                  874
```

(18.5C V$_H$)

SEQ ID NO: 14
```
gtccactgca cctcggttct atcgattggc tagcaccatg gagacagaca cactcctgct       60
atgggtactg ctgctctggg ttccaggttc cactggtgac gaggttcagc tggtggagtc      120
tgggggaggc ctggtcaggc cggggggtc ccttagactc tcctgtgcag ccgctggatt      180
cactttcaag agttatagca tgaattgggt ccgccaggct ccaggagggg gcctggagtg      240
ggtctcatct atcactagtg gtggtagtaa gacatactat gcagacgtag tgaagggccg      300
attcaccgtc tccagagaca acgccaagca gtcgctctat ctgcaaatga acagcctgag      360
agccgaggac acggctatat acttctgtgc gagatcccta catagtacca gccagcctag      420
ctacatggac gtctgggca gaaagatcac ggtcatcgtc tcctcagcct ccaccaaggg      480
cccatcggtc ttcccctgg caccctcctc aagagcacc tctgggggca gcggccct       540 gggctgcctg gtcaaggact acttccccga accggtgacg gtgtcgtgga actcaggcgc      600
cctgaccagc ggcgtgcaca ccttcccggc tgtcctacag tcctcaggac tctactccct      660
cagcagcgtg gtgaccgtgc cctccagcag cttgggcacc cagacctaca tctgcaacgt      720
```

```
gaatcacaag cccagcaaca ccaaggtgga caagagagtt gagcccaaat cttgtgacaa      780
aactcacaca tgcccaccgt gcccagcacc tgaactcctg gggggaccgt cagtcttcct      840 cttccccca aaacccaagg acaccctcat gatctcccgg accctgagg tcacatgc        898
```

(8.11G V<sub>H</sub>)

SEQ ID NO: 15

```
tgcacctcgg ttctatcgat tggctagcac catggagaca gacacactcc tgctatgggt       60
actgctgctc tgggttccag gttccactgg tgaccaggtg cagctgcagg agtcgggtcc     120
aggactggtg aagccttcgg agaccctgtc cctcacctgc agtatttctg gtgtgtccac     180
cagaaattat tattggagct ggatccgcca gtccccaggg aagggactgg agtggattgg     240
atatatcttt aacattggga ccaccaacta caatccgtcc ctcaagagtc gactcaccat     300
atctgtagac acgtcgaaga accagttctc cctgaagatc acctctgtga ccgctgcgga     360
cacggccgtc tattactgtg cgagtggatt tgagtacggt gactatacct tcgactactg     420
gggccaggga accccggtca ccgtctcctc agcctccacc aagggcccat cggtcttccc     480
cctggcaccc tcctccaaga gcacctctgg gggcacagcg gccctgggct gcctggtcaa     540
ggactacttc cccgaaccgg tgacggtgtc gtggaactca ggcgccctga ccagcggcgt     600
gcacaccttc ccggctgtcc tacagtcctc aggactctac tccctcagca gcgtggtgac     660
cgtgccctcc agcagcttgg gcacccagac ctacatctgc aacgtgaatc acaagcccag     720
caacaccaag gtggacaaga gagttgagcc caaatcttgt gacaaaactc acacatgccc     780
accgtgccca gcacctgaac tcctgggggg accgtcagtc ttcctcttcc cccaaaacc     840 caaggacacc ctcatgatct tccggacccc tgaggtcaca tgcgtggtgg tggacgtgag     900
cca                                                                  903
```

(25.10C V<sub>H</sub>)

SEQ ID NO: 16

```
ctcggttcta tcgattggct agcaccatgg agacagacac actcctgcta tgggtactgc       60
tgctctgggt tccaggttcc actggtgacc aggtgcagct gcaggagtct gggggaggcc     120
tggtcaagcc tggggggtcc ctgagactct cctgtacagc ctctggattc aacttcaata     180
aatataacat gaactgggtc cgccaggctc agggaagggg ctggagtggg tctcatccat     240 tagtgctct tagcacttac atctattatg cagactcgct gaagggccga ttcaccgtct     300
ccagagacaa cgccaagaac tcactgtttc tgcaaatgaa cagcctgaga gacgacgaca     360 cggctgtttta ttactgtgcg agagaaatac gacgtgccag tacctggtcc gccgacctct     420
ggggccgtgg cactctggtc actgtctcct cagcctccac caagggccca tcggtcttcc     480
ccctggcacc ctcctccaag agcacctctg gggcacagc ggccctgggc tgcctggtca     540
aggactactt ccccgaaccg gtgacggtgt cgtggaactc aggcgccctg accagcggcg     600
tgcacacctt cccggctgtc ctacagtcct caggactcta ctccctcagc agcgtggtga     660
ccgtgccctc agcagcttgg gcacccagac ctacatctg caacgtgaat cacaagccca     720
gcaacaccaa ggtggacaag agagttgagc ccaaatcttg tgacaaaact cacacatgcc     780
caccgtgccc agcacctgaa ctcctggggg gaccgtcagt cttcctcttc cctccaaacc     840
caaggacacc ctcatgatct                                                860
```

(10.4B V<sub>L</sub>)

SEQ ID NO: 17

```
agctgtgacc ggcgcctacc tgagatcacc ggtgctagca ccatggagac agacacactc       60
ctgctatggg tactgctgct ctgggttcca ggttccactg gtgacgaaat tgtgttgaca     120
cagtctccat cctcactgtc tgcgtctgta ggagacagag tcaccatcac ttgtcgggcg     180
```

-continued

```
agtcgggaca tcaatactta tttaggttgg tttcagcaga gaccagggaa agcccctaag        240
tccctgatct atggtgcatc taatttgcaa aatggggtcc catcaaggtt cagcggcagt        300
ggatctggga cgtattttac tctcaccatc aacggcctgc agactgaaga ctttgcgact        360
tattattgcc aacaatatag catctacccg ctcagtctcg gcggagggac caaggcggac        420
atgaagcgaa ctgtggctgc accatctgtc ttcatcttcc cgccatctga tgagcagttg        480
aaatctggaa ctgcctctgt tgtgtgcctg ctgaataact tctatcccag agaggccaaa        540
gtacagtgga aggtggataa cgccctccaa tcgggtaact cccaggagag tgtcacagag        600
caggacagca aggacagcac ctacagcctc agcagcaccc tgacgctgag caaagcagac        660
tacgagaaac acaaagtcta cgcctgcgaa gtcacccatc agggcctgag ctcgcc          716
```

(19.7E V$_L$)

SEQ ID NO: 18
```
tcagctgtga ccggcgccta cctgagatca ccggtgctag caccatggag acagacacac         60
tcctgctatg gctcctgctg ctctgggttc caggttccac tggtgacgaa attgtgttga        120
cacagtctcc ttccaccctg tctgcatctg tgggagacag agtcaccatc acttgccggg        180
ccagtcagag tattaataat tggttggcct ggtatcagga aaaccagggg aaagccccta        240
agctcctgat aaataaggcg tctagtttag aaagtggggt cccatcaagg ttcagcggca        300
gtggatctgg gacagaattc actctcacca tcaccagcct gcagcctgat gattttgcaa        360
cttattactg ccaacaatat aatagtaatt cgtggacgtt cggccaaggg accaaggtgg        420
acatgaaacg aactgtggct gcaccatctg tcttcatctt cccgccatct gatgagcagt        480
tgaaatctgg aactgcctct gttgtgtgcc tgctgaataa cttctatccc agagaggcca        540
aagtacagtg gaaggtggat aacgccctcc aatcgggtaa ctcccaggag agtgtcacag        600
agcaggacag caaggacagc acctacagcc tcagcagcac cctgacgctg agcaaagcag        660
actacgagaa acacaaagtc tacgcctgcg aagtcaccca tcagggcctg agctcgcccg        720
tcacaaagag cttcaacagg ggagagtgtt agagggagc agctcgacat gataagatac        780
attgatgagt ttgggacaac cacaactaga atgcagtgaa aaaaatgctt tatttgtgaa        840
atttgtgatg ctattgcttt tattgtgaaa tttgtgatgc tattgcttta tttgtaacca        900
ttataa                                                                  906
```

(2.9D V$_L$)

SEQ ID NO: 19
```
actgcacctc ggttctatcg attggctagc accatgaaga cagacacact cctgctatgg         60
gtactgctgc tctgggttcc aggttccact ggtgacgaca ttgtgctgac ccagtctcca        120
gactccctgg ctgtgtctct gggcgagagg gccaccatca actgcaagtc cagccagagt        180
gttttataca gctccaacaa taagaactac ttagcttggt accagcagaa gccaggacag        240
cctcctaagc tgctcattta ctgggcatct acccgggaat ccggggtccc tgaccgattc        300
agtggcagcg gtctgggac agatttcact ctcaccatca gcagcctgca ggctgaagat        360
gtggcagttt attactgtca gcaatattat agtactcctc cgacgttcgg ccaagggacc        420
aaggtggaaa tcaaacgaac tgtggctgca ccatctgtct tcatcttccc gccatctgat        480
gagcagttga atctggaac tgcctctgtt gtgtgcctgc tgaataactt ctatcccaga        540
gaggccaaag tacagtggaa ggtggataac gccctccaat cgggtaactc ccaggagagt        600
gtcacagagc aggacagcaa ggacagcacc tacagcctca gcagcaccct gacgctgagc        660
aaagcagact acgagaaaca caaagtctac gcctgcgaag tcacccatca gggcctgagc        720
tcgcccgtca caaagagctt caacagggga gagtgttagg cggccgcaag cttggccgcc        780
```

```
atggcccaac ttgtttattg cagcttataa tggttacaaa taaagcaata gcatcacaaa      840
tttcacaaat aaagcatttt tttcactgca ttctagttgt ggtttgtcca actc            894
```

(25.6A V<sub>L</sub>)

SEQ ID NO: 20
```
ctcggttcta tcgattggct agcaccatgg agacagacac actcctgcta tgggtactgc      60
tgctctgggt tccaggttcc actggtgacc tgcctgtgct gactcagcct gcctccgtgt      120
ctgggtctcc tggacagtcg atcaccatct cctgcactgg aaccagcagt gacgttggtg      180
cttataacta tgtctcctgg taccaacagc acccaggcaa agcccccaaa ctcataattt      240
atgaagtcaa gattcggccg tcaggggtgt ctaatcgttt ctctggctcc aagtctggca      300
acacggcctc cctgaccatc tctgggctcc aggctgagga cgaggctgat tattttgca      360
gctcatattc aaccaacagc ccttgggtgt tcggcggagg gacgaaggtg accgtcctac      420
gtcagcccaa ggctgccccc tcggtcactc tgttcccacc ctcctctgag gagcttcaag      480
ccaacaaggc cacactggtg tgtctcataa gtgacttcta cccgggagcc gtgacagtgg      540
cctggaaggc agatagcagc cccgtcaagg cgggagtgga gaccaccaca ccctccaaac      600
aaagcaacaa caagtacgcg gccagcagct acctgagcct gacgcctgag cagtggaagt      660
cccacagaag ctacagctgc caggtcacgc atgaagggag caccgtggag aagacagtgg      720
cccctcagaa atgttcatga gcggccgcaa gcttggccgc catggcccaa cttgtttatt      780
gcagcttata atggttacaa ataaagcaat agcatcacaa atttcacaaa taaagcattt      840
ttttcactgc attctagttg tggtttgtcc aaactcatca atgtatctta tcatgtctgg      900
atc                                                                   903
```

(36.1F V<sub>L</sub>)

SEQ ID NO: 21
```
tccaggtcac tgcacctcgg ttctatcgat tggctagcac catggagaca gacacactcc      60
tgctatgggt actgctgctc tgggttccag gttccactgg tgacgaaatt gtgctgacac      120
agtctccagg caccctgtct ttgtctccag gggaaagagc caccctctcc tgcagggcca      180
gtcagagtgt tactaaaaac tacttagcct ggtaccagca gaaacctggc caggctccca      240
ccctcgtcat ctatgatgca tccaccaggg ccagtggcat cccagacagg ttcattggca      300
gtgggtctgg gacagacttc actctcacca tcagcagact ggagcctgaa gattttgcag      360
tatattactg ccaccagtat ggcagctcac ctccgtacac ttttggccgg gggaccaagc      420
tggagatcaa acgaactgtg gctgcaccat ctgtcttcat cttcccgcca tctgatgagc      480
agttgaaatc tggaactgcc tctgttgtgt gcctgctgaa taacttctat cccagagagg      540
ccaaagtaca gtggaaggtg gataacgccc tccaatcggg taactcccag gagagtgtca      600
cagagcagga cagcaaggac agcacctaca gcctcagcag caccctgacg ctgagcaaag      660
cagactacga gaaacacaaa gtctacgcct gcgaagtcac ccatcagggc ctgagctcgc      720
ccgtcacaaa gagcttcaac aggggagagt gttaggcggc cgcaagcttg gccgccatgg      780
cccaacttgt ttattgcagc ttataatggt tacaaataaa gcaatagcat cacaaatttc      840
acaaataaag catttttttc actgcattct agttgtgggt tgtccaaact catcaatgta      900
```

(36.9F V<sub>L</sub>)

SEQ ID NO: 22
```
aggtcactgc acctcggttc tatcgattgg ctagcaccat ggagacagac acactcctgc      60
tatgggtact gctgctctgg gttccaggtt ccactggtga cgacatcgtg atgacccagt      120
ctccagactc cctggctgtg tctctgggcg agagggccac catcaactgc aagtccagcc      180
agactgtttt gttcacctcc tattacgtag cttggtatca acaaaagcca gggcagccgc      240
```

-continued

```
ctaagttgct cttttccggg gcctcttctc gggaatccgg ggtccctgac cgattcagtg     300
ccggcgggtc tgggacagat ttctatctca ccatcaacag cctgcaggct gaagatgtgg     360
cagattacta ttgtcagcaa tatcatactc ctcctttcac tttcggcgga gggaccaagc     420
tggagatcag acgaactgtg gctgcaccat ctgtcttcat cttcccgcca tctgatgagc     480
agttgaaatc tggaactgcc tctgttgtgt gcctgctgaa taacttctat cccagagagg     540
ccaaagtaca gtggaaggtg gataacgccc tccaatcggg taactcccag agagtgtca     600 cagagcagga cagcaaggac agcacctaca gcctcagcag caccctgacg ctgagcaaag     660
cagactacga gaaacacaaa gtctacgcct gcgaagtcac catcagggc ctgagctcgc      720 ccgtcacaaa gagcttcaac aggggagagt gttaggcggc cgcaagcttg gccgccatgg     780
cccaacttgt ttattgcagc ttataatggt tacaaataaa gcaatagcat cacaaatttc     840
acaaataaag cattttttc actgcattct agttgtggtt tgtccaaact catcaatgta      900
tcttatcatg tctggatcgg ga                                              922
```

(37.2D V_L)

SEQ ID NO: 23

```
tcactgcacc tcggttctat cgattggcta gcaccatgga gacagacaca ctcctgctat     60
gggtactgct gctctgggtt ccaggttcca ctggtgacga acgcactc acgcagtctc       120 cagccaccct gtctgtgtct caggggaaa cagccaccct ctcctgcagg gccagtcaaa      180
atgttatcaa caacttagcc tggtaccagc agaaacctgg ccaggctccc aggctcctca     240
tttatggtgc atccaccagg gccactggta tcccagccag gttcagtggc agtgggtctg     300
ggacagagtt cactctcacc atcagcagca tgcagtctga agattttgca gtttattact     360
gtcagcaata taatgactgg cctcgaagtt ttggccaggg gaccaggctg gacatcagac     420
gaactgtggc tgcaccatct gtcttcatct cccgccatc tgatgagcag ttgaaatctg      480
gaactgcctc tgttgtgtgc ctgctgaata acttctatcc agagaggcc aaagtacagt     540 ggaaggtgga taacgccctc caatcgggta actcccagga gagtgtcaca gagcaggaca     600
gcaaggacag cacctacagc ctcagcagca cctgacgct gagcaaagca gactacgaga     660 acacaaagt ctacgcctgc gaagtcaccc atcagggcct gagctcgccc gtcacaaaga      720
gcttcaacag gggagagtgt taggcggccg caagcttggc cgccatggcc caacttgttt     780
attgcagctt ataatggtta caaataaagc aatagcatca caaatttcac aaataaagca     840
tttttttcac tgcattct                                                   858
```

(37.2G V_L)

SEQ ID NO: 24

```
tccaggtcac tgccctcggt tctatcgatt ggctagcacc atggagacag acacactcct     60
gctatgggta ctgctgctct gggttccagg ttccactggt gacgacattg tgctgaccca     120
gtctccaggc accctgtctt tgtctccagg ggaaagagcc accctctcct gcagggccag     180
tcagagtgtg aacagcatct cttagcctgg taccagcag aaacctggcc aggctcccag      240
gctcctcatc tatggtgcat ccagcagggc cactggcatc cagacaggt tcagtggcag     300 tgggtctggg acagacttca ctctcaccat cagcagactg gagcctgagg attttgcagt    360
gtattactgt cagcagtatc atagctcacc taagctcact ttcggcggag ggaccaaggt     420
ggagatcaaa cgaactgtgg ctgcaccatc tgtcttcatc ttcccgccat ctggtgagca     480
gttgaaatct ggaactgcct ctgttgtgtg cctgctgaat aacttctatc cagagaggc     540 caaagtacag tggaaggtgg ataacgccct caatcgggt aactcccagg agagtgtcac      600
agagcaggac agcaaggaca gcacctacag cctcagcagc ccctgacgc tgagcaaagc     660 agactacgag aaacacaaag tctacgcctg cgaagtcacc catcagggcc tgagctcgcc    720
```

-continued

```
cgtcacaaag agcttcaaca ggggagagtg ttaggcggcc gcaagcttgg ccgccatggc    780
ccaacttgtt tattgcagct tataatggtt acaaataaag caatagcatc acaaatttca    840
caaataaagc attttttca ctgcattcta gttgtggttt gtccaaactc atcaatgtat     900
cttatcatgt ctggatcggg aattaattcg gcgcagcacc atggcctgaa ataacctc     958
```

(37.7H V_L)

SEQ ID NO: 25

```
tcactgcacc tcggttctat cgattggcta gcaccatgga gacagacaca ctcctgctat    60
gggtactgct gctctgggtt ccaggttcca ctggtgacca gtctgccctg actcagcctg    120
cctccgtgtc tgggtctcct ggacagtcga tcaccatctc ctgcactgga accggcagtg    180
acattggtgg ttataacttt gtctcctggt accaacagta tcccggcaaa gcccccaaac    240
tcattattta tgaggtccgt attcgggcct caggggtttc caatcgcttc tctggctcca    300
agtctggcaa cacggcctcc ctgaccatct ctggactcca ggctgaggac gaggctgatt    360
attactgcaa ctcatattca atccacagcc tttgggtgtt cggcggaggg accaagttga    420
ccgtcctgcg tcagcccaag gctgccccct cggtcactct gttcccaccc tcctctgagg    480
agcttcaagc caacaaggcc acactggtgt gtctcataag tgacttctac ccgggagccg    540
tgacagtggc ctggaaggca gatagcagcc ccgtcaaggc gggagtggag accaccacac    600
cctccaaaca aagcaacaac aagtacgcgg ccagcagcta cctgagcctg acgcctgagc    660
agtgggagtc cacagaagc tacagctgcc aggtcacgca tgaagggagc accgtggaga    720
agacagtggc ccctacagaa tgttcatgag cggccgcaag cttggccgcc atggcccaac    780
ttgttattg cagcttataa tggttacaaa taaagcaata gcatcacaaa tttcacaaat    840
aaagcatttt tttcactgca ttctagttgt ggtttgtcca aactcatcaa tgtatcttat    900
catgtctgga tcgggaatta attcggcgca gcaccatggc ctgaaatacc ctctgaaaga    960
ggaacttggt taggtaccttctgaggcgga agaaccatc tgtggaatgt gtgtc    1015
```

(8.9F V_L)

SEQ ID NO: 26

```
cactgccctc ggttctatcg attggctagc accatggaga cagacacact cctgctatgg    60
gtactgctgc tctgggttcc aggttccact ggtgaccagg cagggctgac tcagcctgcc    120
tccgtgtctg gtctcctgg acagtcgatc accatctcct gcactgcagc aacagtgac    180
attggtgatt ttaactttgt ctcctggtac aacagcgcc cagacaaagc ccccaaactc    240
atggtttatg aggtcagcag tcggccctca ggggtttcta tcgcttctc tggctccaag    300
tctggcaaca cggcctccct gaccatctct gggctccagg ctgaggacga ggctgattat    360
tactgcacct catatacaag cagcagcact tttgtcttcg gaactgggac caaggtcacc    420
gtcctaggtc agcccaaggc caaccccact gtcactctgt tcccgccctc ctctgaggag    480
cttcaagcca caaggccac actggtgtgt ctcataagtg acttctaccc gggagccgtg    540
acagtggcct ggaaggcaga tagcagcccc gtcaaggcgg gagtggagac caccacaccc    600
tccaaacaaa gcaacaacaa gtacgcggcc agcagctacc tgagcctgac gcctgagcag    660
tggaagtccc acagaagcta cagctgccag gtcacgcatg aagggagcac cgtggagaag    720
acagtggccc ctacagaatg ttcatgagcg gccgcaagct tggccgccat ggcccaactt    780
gtttattgca gcttataatg gttacaaata aagcaatagc atcacaaatt tcacaaataa    840
agcatttttt tcactgcatt ctagttgtgg tttgtccaaa ctcatcaatg tatcttatca    900
tgtctggatc                                                          910
```

-continued (NE13 V_L)

SEQ ID NO: 27

```
ctcccaggtc actgcacctc ggttctatcg attggctagc accatggaga cagacacact      60
cctgctatgg gtactgctgc tctgggttcc aggttccact ggtgacgaaa cgacactcac     120
gcagtctcca ggcaccctgt ctttgtctcc aggggaaaga gccaccctct cctgcagggc     180
cagtcagagt gttagcagca cctacttagc ctggtaccag cagaaacctg gccagtctcc     240
caggctcctc atttatggtg catccagtag ggccactggc atcccagaca ggttcagtgg     300
cagtgggtct gggacacagt tcactctcac catcaacaga ctggagcctg aagattttgc     360
agtgtattac tgtcagcagt ttggtagccc gtggacattc ggccaaggga ccaaggtgga     420
aatcaaacga actgtggctg caccatctgt cttcatcttc ccgccatctg atgagcagtt     480
gaaatctgga actgcctctg ttgtgtgcct gctgaataac ttctatccca gagaggccaa     540
agtacagtgg aaggtggata acgccctcca atcgggtaac tcccaggaga gtgtcacaga     600
gcaggacagc aaggacagca cctacagcct cagcagcacc ctgacgctga gcaaagcaga     660
ctacgagaaa cacaaagtct acgcctgcga agtcacccat cagggcctga gctcgcccgt     720
cacaaagagc ttcaacaggg gagagtgtta ggcggccgca agcttggccg ccatggccca     780
acttgtttat tgcagcttat aatggttaca ataaagcaa tagcatcaca aatttcacaa     840
ataaagcatt ttttcactg cattctagtt gtggtttgtc caaactcatc aatgtatctt     900
atcatgtc                                                               908
```

(12.1F V_L)

SEQ ID NO: 28

```
gtcactgcac ctcggttcta tcgattggct agcaccatgg agacagacac actcctgcta      60
tgggtactgc tgctctgggt tccaggttcc actggtgacg aaacgacact cacgcagtct     120
ccagccaccc tgtctttgtc tccaggggag agagccaccc tcctgtag gccagtcag       180
agtgttagca gctacttagc ctggtaccaa cacaaacctg gccaggctcc caggctcctc     240
atctatggtg catcaaagag ggccactggc atcccgtcca ggttcagtgg cagtgggtct     300
gggacagact tcagtctcac catcagcagc ctagagcctg aagattttgc agtttactac     360
tgtcagcacc gaagcgactg gcggactacc ttcggccaag gcacgact ggagattaaa       420
cgaactgtgg ctgcaccatc tgtcttcatc ttcccgccat ctgatgagca gttgaaatct     480
ggaactgcct ctgttgtgtg cctgctgaat aacttctatc ccagagaggc caaagtacag     540
tggaaggtgg ataacgccct ccaatcgggt aactcccagg agagtgtcac agagcaggac     600
agcaaggaca gcacctacag cctcagcagc accctgacgc tgagcaaagc agactacgag     660
aaacacaaag tctacgcctg cgaagtcacc catcagggcc tgagctcgcc cgtcacaaag     720
agcttcaaca ggggagagtg ttaggcggcc gcaagcttgg ccgccatggc caacttgtt      780
tattgcagct tataatggtt acaaataaag caatagcatc acaaatttca caaataaagc     840
attttttttca ctgcattcta gttgtggttt gtccaaactc atcaatgtat cttatcatgt     900
ctggatcggg aaattaatcg gcgcagcacc at                                    932
```

(9.8A V_L)

SEQ ID NO: 29

```
ggttctatcg attggctagc accatggaga cagacacact cctgctatgg gtactgctgc      60
tctgggttcc aggttccact ggtgacgaca tcgtgatgac ccagtctcct tccaccctgt     120
ctgcatctgt aggagacaga gtcaccatca cttgccgggc cagtcagagt attgataggt     180
ggttggcctg gtatcagcag aaaccaggga agcccctaa gctcctgatc tatcaggcat     240
ctagtttaga aagaggggtc ccatcaaggt tcagcggcag tggatctggg acagaattca     300
```

-continued

```
ctctcaccat cagcagcctg cagcccgatg attttgcaac ttattactgc caacagtata    360
atggttaccc tctcactttc ggcggaggga ccaaggtgga gatcaaacga actgtggctg    420
caccatctgt cttcatcttc ccgccatctg atgagcagtt gaaatctgga actgcctctg    480
ttgtgtgcct gctgaataac ttctatccca gagaggccaa agtacagtgg aaggtggata    540
acgccctcca atcgggtaac tcccaggaga gtgtcacaga gcaggacagc aaggacagca    600
cctacagcct cagcagcacc ctgacgctga gcaaagcaga ctacgagaaa cacaaagtct    660
acgcctgcga agtcacccat cagggcctga gctcgcccgt cacaaagagc ttcaacaggg    720
gagagtgtta ggcggccgca agcttggccg ccatggccca acttgtttat tgcagcttat    780
aatggttaca ataaagcaa tagcatcaca aatttcacaa ataaagcatt ttttttcactg    840
cattctagtt gtggtttgtc caaactcatc aatgtatctt atcatgtctg gatcg         895
```

(18.5C V$_L$)

SEQ ID NO: 30
```
tccaggtcca ctgcacctcg gttctatcga ttggctagca ccatggagac agacacactc     60
ctgctatggg tactgctgct ctgggttcca ggttccactg gtgacgacat ccagatgacc    120
cagtctccag gcaccctgtc tttgtctcca ggggaaagag ccaccctctc ctgcagggcc    180
agtcagagtg ttatcagtta ctacgtagcc tggtaccagc acaaaggtgg ccaggctccc    240
aggctcctca tttatggtgc atccagcagg gccactggcg tcccagacag gttcagtggc    300
agtgggtctg ggacagactt cactctcacc atcagcagcc tggagcctga agattttgca    360
ctgtattact gtcagtacta tgggagctca cctctgtggg cgttcggcca agggaccaag    420
gtggaaatca aacgaactgt ggctgcacca tctgtcttca tcttcccgcc atctgatgag    480
cagttgaaat ctggaactgc ctctgttgtg tgcctgctga ataacttcta tcccagagag    540
gccaaagtac agtggaaggt ggataacgcc ctccaatcgg gtaactccca ggagagtgtc    600
acagagcagg acagcaagga cagcacctac agcctcagca gcaccctgac gctgagcaaa    660
gcagactacg agaaacacaa agtctacgcc tgcgaagtca cccatcaggg cctgagctcg    720
cccgtcacaa agagcttcaa caggggagag tgttaggcgg ccgcaagctt ggccgccatg    780
gccc                                                                 784
```

(8.11G V$_L$)

SEQ ID NO: 31
```
cggttctatc gattggctag caccatggag acagacacac tcctgctatg ggtactgctg     60
ctctgggttc caggttccac tggtgacgaa attgtgctga ctcagtctcc agccaccctg    120
tctgtgtctc caggggtag gcctccctc tcctgccggg ccagtcagag tattggcgac    180
aagttatcct ggtatcagca gaaacctggg caggctccca ggctcgtcat ctatggtgca    240
tataccaggg ccactgatat ctcacccagg ttcagtggca gtaggtctgg gacagacttc    300
aatctcacca tcagcagaat gcagtctgga gactttgcag tttatttctg tcagcagtat    360
gaaaactggc ctcggacttt tggccagggg accaagctgg agatcaaacg aactgtggct    420
gcaccatctg tcttcatctt cccgccatct gatgagcagt tgaaatctgg aactgcctct    480
gttgtgtgcc tgctgaataa cttctatccc agagaggcca agtacagtg aaggtggat    540
aacgccctcc aatcgggtaa ctcccaggag agtgtcacag agcaggacag caaggacagc    600
acctacagcc tcagcagcac cctgacgctg agcaaagcag actacgagaa acacaaagtc    660
tacgcctgcg aagtcaccca tcagggcctg agctcgcccg tcacaaagag cttcaacagg    720
ggagagtgtt aggcggccgc aagcttggcc gccatggccc aacttgttta ttgcagctta    780
taatggttac aataaagcaa atagcatcac aaatttcaca aataaagcat tttttttcact    840
gcatt                                                                845
```

(25.10C V_L)

SEQ ID NO: 32

```
cctcggttct atcgattggc tagcaccatg gagacagaca cactcctgct atgggtactg    60
ctgctctggg ttccaggttc cactggtgac gacatccaga tgacccagtc tccatcctcc   120
ctgtctgcat ctgttggaga cagagtcatc atcacttgcc gggcaagtca gagcatcagc   180
agctctttaa attggtatca gcagaaacca gggaaagccc ctaagctcct gatctatgct   240
gcagtcaatt tggagactgg ggtcccgtca aggttcagtg gcagtggatt tgggacagat   300
ttcactctcg ccatcagcaa tgtgcaacct gaagattttg caacttacta ctgtcaacag   360
agcgatactc ggacttttgg ccgggggacc aagctggacg tcaaacgaac tgtggctgca   420
ccatctgtct tcatcttccc gccatctgat gagcagttga atctggaac tgcctctgtt    480 gtgtgcctgc tgaataactt ctatcccaga gaggccaaag tacagtggaa ggtggataac   540
gccctccaat cgggtaactc ccaggagagt gtcacagagc aggacagcaa ggacagcacc   600
tacagcctca gcagcaccct gacgctgagc aaagcagact acgagaaaca caaagtctac   660
gcctgcgaag tcacccatca gggcctgagc tcgcccgtca caaagagctt caacagggga   720
gaagtgttag gcggccgcaa gcttggccgc catggcccaa cttgtttatt gcagcttata   780
atggttacaa ataaagcaat agcatcacaa atttcacaaa taaagcattt ttttcactgc   840
attctagttg tggtttgtcc aaactcatca atgtatctta tcatgtctgg atcgggaatt   900
```

Antibody Amino Acid Sequences

The V_H and V_L amino acid sequences of the antibodies and complementarity determining regions (CDR) of the V_H and V_L sequences are shown and discussed below.

(10.4B V_H)

SEQ ID NO: 33

METDTLLLWVLLLWVPGSTGDQVQLVQGGGVVQPGRSLRV

SCVTSGFNFRAYGMHWVRQIPGKGLEWVADIWSAETNRHYADSVKGRFTISRDNSKSTLY

LQMNSLRAEDTGVYTCAKARPGYDYVVDLWGQGTLVTVSSASTKGPSVFPLAPCSRSTSG

GTAALGCLVKDYFTEPVTVSWNSGALTSGVHTFPAVLQSSGL (19.7E V_H)

SEQ ID NO: 34

METDTLLLWVLLLWVPGSTGLEVQLVESGGGLVRPGGSLRLSCAA

SGESFSSYSMHWIVRHVPGKGLVWVSYINSDGSTKIYADSVKGRFSISRDNAKNKLYLQMD

SLRVEDTAVYSCVRLNHYDWSPFVWGQGTLVTVSSASTKGPSVFPLAPSSKSTSGGTAAL

GCLVKDYFPEPVTVSWNSGALTSGVHTFPAVLQSSGLYSLSSVVTVPSSSLGTQTYICNV

NHKPSNIKVDKKVEPQSCDKTHTCPPCPAPELL (2.9D V_H)

SEQ ID NO: 35

METDTLLLWVLLLWVPGSTGDEVQLVESGGGLVKPGGSLRLSCAASGF

TFTRFTLTWVRQAPGKGLEWVSSISSGSSDINYADSVKGRFTISRDNARNSLFLQMSSLR

VDDTAVYYCAKDPRSGISGRYGMDVWGQGTTVIVSSASTKGPSVFPLAPCSRSTSGGTAA

LGCLVKDYFPEPVTVSWNSGALTSGVHTFPAVLQSSGLYSLSSVVTVPSSSLGTQTYICN

VNHKPSNTKVDKRVEPKSCDKTHTCPPCPAPELLGGPSVFLFPPKPKDTLMISRTPEVTC

VVVDVS (25.6A V_H)

SEQ ID NO: 36

METDTLLLWVLLLWVPGSTGDQVQLQESGGGLVKAGGSLRLSCAASGFMFE

RYSLHWVRQTPGKGLEWVSSISSLSGSHINYADSVKGRFTISRDNAKNSLSLQMNSLRVE

DTAIYYCARDRRSGSSPVPLDVWGQGTTVTVSSASTKGPSVFPLAPSSKSTSGGTAALGC (36.1F V_H)

SEQ ID NO: 37

METDTLLLWVLLLWVPGSTGDQVQLQESGAGLVKPSETLSLTCAVSGGP

FSGAYWTWIRQTPGKGLEWIGEAGRSGTTNYNPSLKSRVTISLDTSKSQFSLKLTSVTAA

DTAVYFCGRRQIMSLSNLYKRPVDSWGRGTPVIVSSASTKGPSVFPLAPSSKSTSGGTAA

LGCLVKDYFPEPVTVSWNSGALTSGVHTFPAVLQSSGLYSLSSVVTVPSSSLGTQTYICN

VNHKPSNTKVDKRVEPKSCDKTHTCPPCPAPELLGGPSVFLFPPX (36.9F V_H)

SEQ ID NO: 38

METDTLLLWVLLLWVPGSTGDEVQNQSGGGLVKAGGSLKLSCGASGFT

FSSYSMSWVRQAPGKGLEWVSYISSGGSSIHYADSVKGRFTISRDNAKNSLYLQMKNLRV

DDTGRYYCVRDPRSGISGRYGMDVWGQGTTVTVSSASTKGPSVFPLAPSSKSTSGGTAAL

GCLVKDYEPEPVTVSWNSGALTSGVHTFPAVLQSSGLYSLSSVVTVPSSSLGTQTYICNV

NHKPSNTKVDKRVEPKSCDKTHTCPPCPAPELLGGPSVFLFPPNPRTPS*S (37.2D V_H)

SEQ ID NO: 39

METDTLLLNVLLLWVPGSTGDEVQLVQSGAEVKKPGASVKVSCKASGYT

FTKYGISWVRQAPGQGLEWMGWISAFNGYTRYGQRFQGKVTMTTDTSTNTASLEVRTLTS

NDTAVYYCARQYPDQYSSSGWPRLFAMDVWGQGTTVIVSPASTKGPSVFPLAPSSKSTSG

GTAALGCLVKDYFPEPVTVSWNSGALTSGVHTYPAVLQSSGLYSLSSVVTVPSSSLGTQT

YICNVNHKPSNTKVDKRVEPKSCDKTHTCPPCPAPELLGGPSVFLF (37.2G V_H)

SEQ ID NO: 40

METDILLLWVLThLWVPGSTaIDEVQ.LVESGGGLVKPGGSRRLSCAASGFT
FSRDTMTWVRQAPGKGLEWVASISSGSSDINYADSVKGRFTISRDNGKNSLYLHMNSLRA
DDTAITYCARDPRSGISGRYGMDVWGQGTTVTVSSASTKGPSVFPLAPSSKSTSGGTAAI
GCLVKDYFPEPVTVSWNSGALTSGVHTFPAVLOSGLYSLSSVVTVPSSSLGTQTYICNV
NHKPSNTKVDKRVEPKSCDKIHTCPPCPAPELLGGPSVFIETTKPKDTLMISRIPEVICV
VVDV-SHEDPEVKFNWYVDGV (37.7H V_H)

SEQ ID NO: 41

METDTLLLWVLLLWVPGSTGDEVQLVQSGGGLVKAGGSLRLSCAASGF
TFSTYSMNWIRCAPGKGLEWVASISSRSGSHINTVDSVKGRFTISRDNARDLLYIL
RVDDSALTYCARDBESGTSPLPLDVWGQGITVTVFSASTKGPSVFPLAPSSKSTSGGTAA
LGCLVKIDYFIPEPVTVSWNSGALTSGVHTFPAVLQSSGLYSLSSVVTVPSSSIGTQTYICN
VNHKPSNiKVDKRVEPXSCDKIHTCPPCPAPELLGGPSVFLYPPKPKDILMISRTPEVTC
VVVDVEHE (8.9F V_H)

SEQ ID NO: 42

METDTLLLWVLLLWVPGSTGDQGTLRESGPGLVRPSETLSLTCGVEGYSIS
SGYYWGNIRQPPGIKGLEVVIGNIYRSGSTYYNPSLKSRVTVSIDISKNUSLKLNSVTAAD
TAVYYCARSGIKVA-nDYTTEMDVWGQGTDDYSYAMDVWGQGITVTVSSASTKGPSVFPLA
PSSKSTSGGTAALGCLVKIDYFIPEPVTVSWNSGALTSGVHTFPAVLQSSGLYSLSSVVTVP
SSSLGTQTYICNVNHKPSNIKVDKRVEPKSCDKTHTCPPCPAPELLGGPSVFLYPPKPKID
TLMX (NE13 V_H)

SEQ ID NO: 43

METDTLLLWVLLLWVPGSTGDEVQLVESGGGLVKPGGSLRLSCVASGFT
FSSYSMNWVRQAPGKGLEWVSSISSGSSYIEYADSVKGRLTISRDNAKKSLYLQLNSLRA
FEDTAVYYCARHTARIDSYEGMDVWGOGTTVTVSSASTKGPSVFPLAPSSKSTSGGTAALG
CLVKDYYPEPVTVEWNSGALTSGVHTFPAVLQSSGLYSLSSVVTVPSSSLGTQTYICNVN
HKPSNTKVDKRVEPKSCDKTHTCPPCPAPELLGGPSVFLFPPKPKDTLMISRTP (12.1F V_H)

SEQ ID NO: 44

METDILLLWVLLLWVPGSTGDQVQLQESGAGLLKPSETLSLSCTVDGE
SYNGFFWTWIRQPPGKGLEWIGEINHLASTGYNPSLKSRVTISVDTSKNQFSLKLTSVTA
ADTAVYYCARGYSYGFAWPNYHYLDVWGKGTTVTVSSASTKGPSVFPLAPSSKSTSGGTA

-continued

ALGCLVKDYFPFPVTVSWNSGALTSGVHTFPAVLQSSGLYSLSSVVTVPSSSLGTQTYIC
NVNHKIPSNIKVDKRVEPKSCDKIHTCPPCPAPELLGGPSVFLXDPKPKDTLMISRTPEVT
CVVVDVS (9.8A $V_H$)

SEQ ID NO: 45
METDTLLLWVLLLWVPGSTGDEVQLVQSGGRLVQPGGSLRLSCVASGFTFSSH
AMSWVRQAPGKGLEWVSGFSGSSGTTKYADSVKGRFTISRDNSKKTLYLQMNSLRAEDTA
VYYCAKGFSPFRGVQFPYFDYWGQGTLVTVSSASTKGPSVFPLAPSSKSTSGGTAALGCL
VKDYFPEPVTVSWNSGALTSGVHTFPAVLQSSGLYSLSSVVTVPSSSLGTQTYICNVNHK
PSNTKVDKRVEPKSCDKTHTCPPCPAPELLGGPSVFLFPPKPRTPS*SPGP (18.5C $V_H$)

SEQ ID NO: 46
METDTLLLWVLLLWVPGSTGDEVQLVESGGGLVRPGGSLRLSCAAAGF
TFKSYSMNWVRQAPGRGLEWVSSITSGGSKTYYADVVKGRFTVSRDNAKQSLYLQMNSLR
AEDTAIYYCARSLHSTSUSYMOVWGRKITVTVESASTKGPSVFPLAPSSKSTSGGTAAL
GCLVKDYFPEPVTVSWNSGALTSGVILITFRANIQSSGLYSLSSVVTVPSSSLGTQTYICNV
NHKPSNTKVDKRVEPKSCDKTH7CPPCPAPET.LGGPSVFmFTPKPKDTLMISRTFEVTC (8.11G $V_H$)

SEQ ID NO: 47
METDTLLLWVLLLWVPGSTGDQVQLQESGPGLVKPSETLSLTCSISGVST
RNYYWSWIRQSPGKGLEWIGYIFNIGTTNYNPSLKSRLTISVDTSKNQFSLKITSVTAAD
TAVYYCASGFEYGDYTFDYWGQGTPVTVSSASTKGPSVFPLAPSSKSTSGGTAALGCLVK
DYYPEPVTVEWNSGALTSGVhTFPAVLQ.SSGLYSLSSVVTVPSSSLGTQTYICNVNHKPS
NTKVDKRVEPKSCDKTHTCPPCPAPELLGGPSVTLEPPKPKDTLMTFRTPEVTCTN'S (25.10C $V_H$)

SEQ ID NO: 48
METDTLLLWVLLLWA/PGSTGDWQLQESGGCLVKTGGSLRLSCTABCFNFNK
YNMNWVRQAPGKCLEWVSSTSALSTYTYYKf1SLKGRFTVSRDNAKNST.FLQMNSLRDD-
nT
AVYYCAREIRRSTWSADLWGRGILVTVSSASTKGPSVFPLAPSSKSTSGGTAALGCLVK
DYFPEPVTVSWNSGALTSGVHTFPAVLQSSGLYSLSSVVTVPSSSLGTQTYICNVNHKPS
NTKVDKRVEPKSCDKTHTCPPCPAPELLGGPSVFLFPPNPRTPS (10.4B $V_L$)

SEQ ID NO: 49
METDTLLLWLLLLWVPGSTGDEIVLIQSPSSISASVGDRVTITCRA
SRDINTYLGRPCKAPKSLIYGASNLQNCVPSRFSCSGSGTYFTLTINCLQTEDFAT
YYCQQYSTYPLSLGGGTKADMKRYVAAPSVFIFPPSDET,KSGTASVVCLLNNEYPREAK
VQWKVDNALQSGNSQESVTEQDSKDSTYSLSSTLTLSKADYEKHKVYACEVTHQCLSSP (19.7E $V_L$)

SEQ ID NO: 50
METDTLLLWLLLLWA/PGSTGDETVLIQSPSTLSASVGDRVTITCRA
SQSINNWLAWYQEKPGKAPKLLINKASSLESGVPSRFSGSGSGTEFTLTITSLQPDDFAT
TYCOONSNSWIFGQGTKVDMKRTVAAPSVFIFIPPSDEQLKSGTASVVCLLNNFYPREAK
VQWKVDNALQSCNSQESVIEQDSKDSTYSLSSILTLSKADYEKEKVYACEVTHQCLSSPV
TKSFNRGEC (2.9D $V_L$)

SEQ ID NO: 51
MKTDTLLLWVLLLWVPCSTGDDiVLTQSPDSLAVSLCERATINCKESQS
VLYSSNNKNYIARYQQKPCUPKLLIYWASTRESCVPDRFSGSGSGTDFTLTISSLQAED
VAVYYCXYYSTPPTFCQGTKVEIKRTVAAPSVFIFPPSDEQLKSGTASVVCLLNNEYPR
EAKVQWKVDNALOGNSQESVTEODSKDSTYSLSSILTLSKADYEKHKVYACEVTHQGLS
SP+32SENRGEC (25.6A $V_L$)

SEQ ID NO: 52
METDTILLWVLLLWVPGSTGDIEWLT&PASVSGSPGQSITISCIGTSSDVGA
YNYVSWYQQHPGKAPKITIYEVKIRPSGVENRFSGSKSaiNTASLTISG1QAEDEADYFCS
SYSINSPWVFGGGTKVTVLB.QPKALAPSVTLEPPSSEELQANKATLVCLISDFYPGAVTVA
WKADSSEWKAGVETTITSKQSNNKYAASSYLSLIPEQWKSHRSYSCQVIHEGSTVEKTVA
PTECS*

(36.1F $V_L$)

SEQ ID NO: 53
METDTLLLWVLLLWVPGSTGDEIVLIQSPGILSLSPGERATLSCRAS
QSVIKNYLAWYQQKPGQAPTLVIYDASTRASGIPDRFIGSGSGTDFTLTISRLEPEDFAV
YYCILIQYGSSPPYTFGRGTT+21TETKRIVAAPSVFiYPPSDEQLKSGTASVWLLNNFYPREA
KVQWKVDNAIQSGNSQESVIEQDSKDSTYSLSSTLILSKADYEKHKVYACEVTHQGLSSP
VIKSFNRGEC*

(36.9F $V_L$)

SEQ ID NO: 54
METDILLT.WVLThWVPGSTaDDiVNIQSPDSLAVSLGERATINCKSSQ
TVLFTSYYVAWYQQKPGQPPKLLFSGASSRESGVPDRFSAGGSGTDFYLTINSLQAEDVA
DYYCQOYHIPPPFTFGGGIKLEIRRIVAAPSVFIFPIPSDEQLKSGTASVVCLLNNFYPREA
KVQWKVDNALQSGNSQESVIEQDSKDSTYSLSSTLILSKADYEKHKVYACEVTHQGLSSP
VIKSENRGEC.*

(37.2D $V_L$)

SEQ ID NO: 55
METDILLLWVLLLWVPGSTGDETTLTOPATLSVSPGETATLSCRASQN
WINNIAWYQQKPGQAPRLLIYGABTRATGIPARYSGSGSGTEFTLTISSMQSEDFAVYC
QQYNDWPBEFGQGTRLDIRRTVAAPSVFIFPPSDEQLKSGTASVVCLLNNFYPREAKVQW
KVDNALOGNSQESVIEODSKDSTYSLSSILTLSKADYEKHKVYACEVIHQGLSSPVIKS
FNRGEC*

(37.2G V_L)

SEQ ID NO: 56

METDTLLLWVLLLWVPGSTGETIVLIQSPGILSLSPGERATLSCRAS
QSVNSIFIAWYQQKPGQAPRLLIYGASSRATGIPDRYSGSGSGTDFTLTISRLEPEDFAV
YYCQQESSPKITFGGGIKVEIKRIVAAPSVFIFPPSGEQLKSGTASVWLLNNFYPREA
KVQWKVDNAIQSGNSQESVIEQDSKDSTYSLSSTLILSKADYEKHKVYACEVTHQGLSSP
VTKSFNRGEC*

(37.7H V_L)

SEQ ID NO: 57

METDTILLWVELLWVPGSTGDQSALT&PASVSGSPGQSITISCTGIGSD
IGGYNEVSWNWPGKAPKLIIIEVRTRASGVSNRYSGSKSGNTASLTISGLQAEDEADY
YCNSYSTESPWVEGGGTKLIVERUKAAPSVTLFPPSSFEL(ANKATLVCLISDFYPGAY
TVAWKADSSPVKAGVETTTPSKQSNNKYAASSYLSTPEQWESHRSYSCQVTHEGSTVEK
TVAPTECS*

(8.9F V_L)

SEQ ID NO: 58

METDTLLLWVLLLWVPGSTGDQAGETQPASVSGSPGQSITISCTAANSD

IGDFNFVSWYQQRPDKAPKLMVYEVSSRPSGVSNRFSGSKSGNTASLTISGLQAEDEADY

YCTSYTSSSTFVFGTGTKVTVLGQPKANPTVTLFPPSSEELQANKATLVCLISDFYPGAV

TVAWKADSSPVKAGVETTTPSKQSNNKYAASSYLSLTPEQWKSHRSYSCQVTHEGSTVEK

TVAPTECS*

(NE13 V_L)

SEQ ID NO: 59

TMETDTLLLWVLLLWVPGSTGDETTLTQSPGTLSLSPGERATLSGRA

SQSVSSTYLAWYQQKPGQSPRLLIYGASSRATGIPDRFSGSGSGTQFTLTINRLEPEDFA

VYYCQQFGSPWTFGQGTKVEIKRTVAAPSVFIFPPSDEQLKSGTASVVCLLNNFYPREAK

VQMKVDNALQSGNSQESVTEQDSKDSTYSLSSTLTLSKADYEKHKVYACEVTHQGLSSPV

TKSFNRGEC*

(12.1F V_L)

SEQ ID NO: 60

METDTLLLWVLLLWVPGSTGDETTLTQPATLSLSPGERATLSCRSQ

SVSSYLAWYQHKPGQAPRLLIYGASKRATGIPSRFSGSGSGTDFSLTISSLEPEDFAVYY

CQHRSDWRTTFGQGTRLEIKRTVAAPSVFIFPPSDEQLKSGTASVVCLLNNFYPREAKVQ

WKVDNALQSGNSQESVTEQDSKDSTYSLSSTLTLSKADYEKHKVYACEVTHQGLSSPVTK

SFNRGEC*

(9.8A V_L)

SEQ ID NO: 61

METDTLLLWVLLLWVPGSTGDDIVMTQSPSTLSASVGDRVTITCRASQSIDRW

LAWYQQKPGKAPKLLIYQASSLERGVPSRFSGSGSGTEFTLTISSLQPDDFATYYCQQYN

GYPLTFGGGTKVEIKRTVAAPSVFIFPPSDEQLKSGTASVVCLLNNFYPREAKVQWKVDN

ALQSGNSQESVTEQDSKDSTYSLSSTLTLSKADYEKHKVYACEVTHQGLSSPVTKSFNRG

EC*

(18.5C V_L)

SEQ ID NO: 62

METDTLLLWVLLLWVPGSTGDDIQMTQSPGTLSLSPGERATLSCRA

SQSVISYYVAWYQHKGGQAPRLLIYGASSRATGVPDRFSGSGSGTDFTLTISSLEPEDFA

LYYCQYYGSSPLWAFGQGTKVEIKRTVAAPSVFIFPPSDEQLKSGTASVVGLLNNFYPRE

AKVQWKVDNALQSGNSQESVTEQDSKDSTYSLSSTLTLSKADYEKHKVYACEVTHQGLSS

PVTKSFNRGEC*

(8.11G V_L)

SEQ ID NO: 63

METDTLLLWVLLLWVPGSTGDEIVLTQPATLSVSPGGRASLSCRASQSIGD

KLSYYQQKPGQAPRLVIYGAYTRATDISPRFSGSRSGTDFNLTISRMQSGDFAVYFCQQY

-continued

```
ENWPRTFGQGTKLEIKRTVAAPSVFIFPPSDEQLKSGTASVVCLLNNFYPREAKVQWKVD

NALQSGNSQESVTEQDSKDSTYSLSSTLTLSKADYEKHKVYACEVTHQGLSSPVTKSFNR

GEC*

(25.10C V_L)
                                                         SEQ ID NO: 64
METDTLLLWVLLLWVPGSTGDDIQTQSPSSLSASVGDRVIITCRASQSIS

SSLNWYQQKPGKAPKLLIYAAVNLETGVPSRFSGSGFGTDFTLAISNVQPEDFATYYCQQ

SDTRTFGRGTKLDVKRTVAAPSVFIFPPSDEQLKSGTASVVCLLNNFYPREAKVQWKVDN

ALQSGNSQESVTEQDSKDSTYSLSSTLTLSKADYEKHKVYACEVTHQGLSSPVTKSFNRG

EVLGGRKLGRHGPTCLLQLIMVTNKAIASQISQIKHFFHCILVVVCPNSSMYLIMSGSGI
```

FIG. 7 provides a sequence alignment prepared using CLUSTAL OMEGA™ (1.2.4) multiple sequence alignment (from EMBL-EBI, a part of the European Molecular Biology Laboratory) for the heavy chain variable region amino acid sequences, with CDRs highlighted in bold typeface: CDR1 (marked with +), CDR 2 (marked with ^), and CDR3 (marked with #).

FIG. 8 provides a sequence alignment prepared using CLUSTAL OMEGA™ (1.2.4) multiple sequence alignment for the light chain variable region amino acid sequences, with CDRs highlighted in bold typeface: CDR1 (marked with +), CDR 2 (marked with ^), and CDR3 (marked with #).

The HC CDR Sequence Table below lists the sequences of CDR1, CDR 2, and CDR3 of the $V_H$ of each of the 16 neutralizing antibodies described herein. The LC CDR Sequence Table below lists the sequences of CDR1, CDR 2, and CDR3 of the $V_L$ of each of the 16 neutralizing antibodies described herein.

| HC CDR Sequence Table. | | | |
|---|---|---|---|
| Antibody | HC CDR1 | HC CDR2 | HC CDR3 |
| 10.4B | GFNFRAYG (SEQ ID NO: 65) | IWSAETNRH (SEQ ID NO: 66) | AKARPGYDYVVDL (SEQ ID NO: 67) |
| 19.7E | GFSFSSYS (SEQ ID NO: 68) | INSDGSTKI (SEQ ID NO: 69) | VRLVHYDWSPFV (SEQ ID NO: 70) |
| 2.9D | GFTFTRFT (SEQ ID NO: 71) | ISSGSSDIN (SEQ ID NO: 72) | AKDPRSGISGRYGMDV (SEQ ID NO: 73) |
| 25.6A | GFMFERYS (SEQ ID NO: 74) | ISSLSGSHIN (SEQ ID NO: 75) | ARDRRSGSSPVPLDV (SEQ ID NO: 76) |
| 36.1F | GGPFSGAY (SEQ ID NO: 77) | AGRSGTTN (SEQ ID NO: 78) | GRRQIMSLSNLYKRPVDS (SEQ ID NO: 79) |
| 36.9F | GFTFSSYS (SEQ ID NO: 80) | ISSGGSSIH (SEQ ID NO: 81) | VRDPRSGISGRYGMDV (SEQ ID NO: 82) |
| 37.2D | GYTFTKYG (SEQ ID NO: 83) | ISAFNGYTR (SEQ ID NO: 84) | ARQYPDQYSSSGWPRLFAMDV (SEQ ID NO: 85) |
| 37.2G | GFTFSRDT (SEQ ID NO: 86) | ISSGSSDIN (SEQ ID NO: 87) | ARDPRSGISGRYGMDV (SEQ ID NO: 88) |
| 37.7H | GFTFSTYS (SEQ ID NO: 89) | ISSRSGSHIN (SEQ ID NO: 90) | ARDRRSGTSPLPLDV (SEQ ID NO: 91) |
| 8.9F | GYSISSGYY (SEQ ID NO: 92) | IYRSGSTY (SEQ ID NO: 93) | ARSGIKVADDYYYEMD VWGQGTDDYSYAMDV (SEQ ID NO: 94) |
| NE13 | GFTFSSYS (SEQ ID NO: 95) | ISSGSSYIE (SEQ ID NO: 96) | ARHTARIDSYHGMDV (SEQ ID NO: 97) |
| 12.1F | GESFNGFF (SEQ ID NO: 98) | INHLASTG (SEQ ID NO: 99) | ARGYSYGFAWPNYHYLDV (SEQ ID NO: 100) |
| 9.8A | GFTFSSHA (SEQ ID NO: 101) | FSGSSGTTK (SEQ ID NO: 102) | AKGFSPFRGVQFPYFDY (SEQ ID NO: 103) |
| 18.5C | GFTFKSYS (SEQ ID NO: 104) | ITSGGSKTY (SEQ ID NO: 105) | ARSLHSTSQPSYMDV (SEQ ID NO: 106) |

HC CDR Sequence Table.

| Antibody | HC CDR1 | HC CDR2 | HC CDR3 |
|---|---|---|---|
| 8.11G | GVSTRNYY (SEQ ID NO: 107) | IFNIGTTN (SEQ ID NO: 108) | ASGFEYGDYTFDY (SEQ ID NO: 109) |
| 25.10C | GFNFNKYN (SEQ ID NO: 110) | ISALSTYIY (SEQ ID NO: 111) | AREIRRASTWSADL (SEQ ID NO: 112) |

LC CDR Sequence Table.

| Antibody | LC CDR1 | LC CDR2 | LC CDR3 |
|---|---|---|---|
| 10.4B | RDINTY (SEQ ID NO: 113) | GAS | QQYSIYPLS (SEQ ID NO: 114) |
| 19.7E | QSINNW (SEQ ID NO: 115) | KAS | QQYNSNSWT (SEQ ID NO: 116) |
| 2.9D | QSVLYSSNNKNY (SEQ ID NO: 117) | WAS | QQYYSTPPT (SEQ ID NO: 118 |
| 25.6A | SSDVGAYNY (SEQ ID NO: 119) | EVK | SSYSTNSPWV (SEQ ID NO: 120) |
| 36.1F | QSVTKNY (SEQ ID NO: 121) | DAS | HQYGSSPPYT (SEQ ID NO: 122) |
| 36.9F | QTVLFTSYY (SEQ ID NO: 123) | GAS | QQYHTPPFT (SEQ ID NO: 124) |
| 37.2D | QNVINN (SEQ ID NO: 125) | GAS | QQYNDWPRS (SEQ ID NO: 126) |
| 37.2G | QSVNSIF (SEQ ID NO: 127 | GAS | QQYHSSPKLT (SEQ ID NO: 128) |
| 37.7H | GSDIGGYNF (SEQ ID NO: 129) | EVR | NSYSIHSPWV (SEQ ID NO: 130) |
| 8.9F | NSDIGDFNF (SEQ ID NO: 131) | EVS | TSYTSSSTFV (SEQ ID NO: 132) |
| NE13 | QSVSSTY (SEQ ID NO: 133) | GAS | QQFGSPWT (SEQ ID NO: 134) |
| 12.1F | QSVSSY (SEQ ID NO: 135) | GAS | QHRSDWRTT (SEQ ID NO: 136) |
| 9.8A | QSIDRW (SEQ ID NO: 137) | QAS | QQYNGYPLT (SEQ ID NO: 138) |
| 18.5C | QSVISYY (SEQ ID NO: 139) | GAS | QYYGSSPLWA (SEQ ID NO: 140) |
| 8.11G | QSIGDK (SEQ ID NO: 141) | GAY | QQYENWPRT (SEQ ID NO: 142) |
| 25.10C | QSISSS (SEQ ID NO: 143) | AAV | QQSDTRT (SEQ ID NO: 144) |

Diagnostics

The antibodies described herein may be used in a variety of immunoassays for LASV, LCMV, and other arenaviruses. The antibodies of the invention can be produced with high quality control and are suitable as reagents for the purposes of detecting antigen in biological samples. By way of example and not limitation, antibodies of the invention could be used as reagents in an ELISA assay to detect Lassa antigen in a biological sample from a subject. The antibodies can be labeled, e.g., bound to a detectable labelling group such as a fluorescent dye, a quantum dot label, R-phycoerythrin, streptavidin, biotin, an enzyme, a radioiosotope, and the like. Such labelling techniques are well known in the antibody art.

Vaccines

Vaccines for LASV, LCMV, and other arenaviruses also are described herein. In one aspect the vaccines are DNA-based vaccines. One skilled in the art is familiar with administration of expression vectors to obtain expression of an exogenous protein in vivo. See, e.g., U.S. Pat. Nos. 6,436,908; 6,413,942; and 6,376,471. Viral-based vectors for delivery of a desired polynucleotide and expression in a desired cell are well known in the art and non-limiting examples are described herein.

Administration of expression vectors includes local or systemic administration, including injection, oral administration, particle gun or catheterized administration, and topical administration. Targeted delivery of therapeutic compositions containing an expression vector or subgenomic polynucleotides can also be used. Receptor-mediated DNA delivery techniques are described in, for example, Findeis et al., *Trends Biotechnol.* (1993) 11:202; Chiou et al., *Gene Therapeutics: Methods And Applications Of Direct Gene Transfer* (J. A. Wolff, ed.) (1994); Wu et al., *J. Biol. Chem.* (1988) 263:621; Wu et al., *J. Biol. Chem.* (1994) 269:542; Zenke et al., *Proc. Natl. Acad. Sci. USA* (1990) 87:3655; Wu et al., *J. Biol. Chem.* (1991) 266:338.

Non-viral delivery vehicles and methods can also be employed, including but not limited to, polycationic condensed DNA linked or unlinked to killed adenovirus alone (see, e.g., Cunel, *Hum. Gene Ther.* (1992) 3:147); ligand-linked DNA (see, e.g., Wu, *J. Biol. Chem.* (1989) 264: 16985); eukaryotic cell delivery vehicles (see, e.g., U.S. Pat. No. 5,814,482; PCT Publication Nos. WO 95/07994; WO 96/17072; WO 95/30763; and WO 97/42338); and nucleic charge neutralization or fusion with cell membranes. Naked DNA can also be employed. Exemplary naked DNA introduction methods are described in PCT Publication No. WO 90/11092 and U.S. Pat. No. 5,580,859. Liposomes that can act as gene delivery vehicles are described in U.S. Pat. No. 5,422,120; PCT Publication Nos. WO 95/13796, WO 94/23697, WO 91/14445; and EP 0524968. Additional approaches are described in Philip, *Mol. Cell Biol.* (1994) 14:2411, and in Woffendin, *Proc. Natl. Acad. Sci.* (1994) 91:1581.

For human administration, the codons comprising the polynucleotide encoding one or more antibodies specific for LASV glycoprotein and/or LCMV glycoprotein may be optimized for human use, a process that is standard in the art.

In another aspect, one or more antibodies specific to LASV and/or LCMV or combinations thereof is used as a vaccine. The one or more antibodies or combination thereof may be administered by itself or in combination with an adjuvant. Examples of adjuvants include, but are not limited to, aluminum salts, water-in-soil emulsions, oil-in-water emulsions, saponin, QuilA and derivatives, iscoms, liposomes, cytokines including gamma-interferon or interleukin 12, DNA (e.g. unmethylated poly-CpG), microencapsulation in a solid or semi-solid particle, Freunds complete and incomplete adjuvant or active ingredients thereof including muramyl dipeptide and analogues, DEAE dextrarilmineral oil, Alhydrogel, Auspharm adjuvant, and Algammulin.

The antibody vaccine comprising one or more antibodies specific to LASV and/or LCMV or combinations thereof can be administered orally or by any parenteral route such as intravenously, subcutaneously, intraarterially, intramuscularly, intracardially, intraspinally, intrathoracically, intraperitoneally, intraventricularly, sublingually, and/or transdermally.

Dosage and schedule of administration can be determined by methods known in the art. Efficacy of the one or more antibodies specific to LASV and/or LCMV or combinations thereof as a vaccine for Lassa virus, lymphocytic choriomeningitis virus, or related arenaviruses may also be evaluated by methods known in the art.

Pharmaceutical Compositions

The polynucleotides, polypeptides, and antibodies described herein can further comprise pharmaceutically acceptable carriers, excipients, or stabilizers known in the art (*Remington: The Science and practice of Pharmacy* 20th Ed., 2000, Lippincott Williams and Wilkins, Ed. K. E. Hoover), in the form of lyophilized formulations or aqueous solutions. Acceptable carriers, excipients, or stabilizers are non-toxic to recipients at the employed dosages and concentrations, and may comprise buffers such as phosphate, citrate, and other organic acids; antioxidants including ascorbic acid and methionine; preservatives (e.g. octadecyldimethylbenzyl ammonium chloride, hexamethonium chloride, benzalkonium chloride, benzethonium chloride, phenol, butyl or benzyl alcohol, alkyl parabens such as methyl or propyl paraben, catechol, resorcinol, cyclohexanol, 3-pentanol, and m-cresol); low molecular weight (less than about 10 residues) polypeptides; proteins such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, marmose, or dextrans; chelating agents such as EDTA; sugars such as sucrose, mannitol, trehalose or sorbitol; salt-forming counter-ions such as sodium; metal complexes (e.g. Zn-protein complexes); and/or non-ionic surfactants such as TWEEN™, PLURONICS™ or polyethylene glycol (PEG). Pharmaceutically acceptable excipients are further described herein.

The compositions used in the methods described herein generally comprise, by way of example and not limitation, an effective amount of a polynucleotide or polypeptide (e.g., an amount sufficient to induce an immune response) of the invention or antibody of the invention (e.g., an amount of a neutralizing antibody sufficient to mitigate infection, alleviate a symptom of infection and/or prevent infection).

The pharmaceutical composition can further comprise additional agents that serve to enhance and/or complement the desired effect. By way of example, to enhance the efficacy of the one or more antibodies specific to LASV and/or LCMV or combinations thereof administered as a pharmaceutical composition, the pharmaceutical composition may further comprise an adjuvant. Examples of adjuvants are provided herein.

Also by way of example and not limitation, if the one or more antibodies specific to LASV and/or LCMV or combinations thereof of the invention is being administered to augment the immune response in a subject infected with or suspected of being infected with LASV or LCMV and/or if antibodies of the present invention are being administered as a form of passive immunotherapy, the composition can further comprise other therapeutic agents (e.g., anti-viral agents).

Kits

Kits for use in the instant methods also are described. Kits include one or more containers comprising by way of example, and not limitation, polynucleotides encoding one or more antibodies specific to LASV and/or LCMV or combinations thereof or fragments thereof of the invention and instructions for use in accordance with any of the methods of the invention described herein. In some embodiments of the kit, the antibodies are bound to a detectable label as discussed above.

Generally, instructions comprise a description of administration or instructions for performance of an assay. The containers may be unit doses, bulk packages (e.g., multi-dose packages) or sub-unit doses. Instructions supplied in the kits of the invention are typically written instructions on a label or package insert (e.g., a paper sheet included in the kit), but machine-readable instructions (e.g., instructions carried on a magnetic or optical storage disk) are also acceptable.

The kits are in suitable packaging. Suitable packaging includes, but is not limited to, vials, bottles, jars, flexible packaging (e.g., sealed Mylar or plastic bags), and the like. Also contemplated are packages for use in combination with a specific device, such as an inhaler, nasal administration device (e.g., an atomizer) or an infusion device such as a minipump. A kit may have a sterile access port (e.g. the container may be an intravenous solution bag or a vial having a stopper pierceable by a hypodermic injection needle). The container may also have a sterile access port (e.g. the container may be an intravenous solution bag or a vial having a stopper pierceable by a hypodermic injection needle). Kits may optionally provide additional components such as buffers and interpretive information. Normally, the kit comprises a container and a label or package insert(s) on or associated with the container.

The following non-limiting examples are provided to illustrate certain aspects and features of the materials and methods described herein.

EXAMPLES

Example 1: LCMV Infection of the Mouse and Recombinant Arenaviruses are a Powerful Experimental System to Assess the Potency and Breath of LCMV Neutralizing mMAbs In Vivo Both host and viral factors, as well as route of infection and dose of virus influence the outcome of LCMV infection of the mouse. Thus, intravenous (i.v.) inoculation of adult immune competent mice with LCMV Armstrong (ARM) strain results in an acute infection that induces a protective immune response that mediates virus clearance in 10 to 14 days, a process predominantly mediated by virus-specific CD8+ cytotoxic T lymphocytes (CTL). In contrast, i.v. inoculation with a high dose of the immunosuppressive clone 13 (Cl-13) strain of LCMV causes a persistent infection associated with sustained viremia and generalized immune suppression that can last for 60 to 100 days. This model is robust and has clear outcomes, which provide a valid and cost effective experimental system for initial evaluation of the efficacy of antibody-based strategies to control and clear a LCMV infection. In this regard, the use of Cl-13 based recombinant viruses expressing GPs of interest allows assessment of the safety and in vivo neutralizing activity of GP-specific BNmMAbs. This approach is feasible using state-of-the-art arenavirus reverse genetics that allows rescue of infectious recombinant LCM viruses with predetermined mutations of interest, as well as expressing heterologous either viral or non-viral genes of interest. A single-cycle infectious, reporter expressing, recombinant LCMV in which the GP ORF is replaced by GFP (rLCMVΔGP/GFP) was generated. Genetic complementation with plasmids or stable cell lines expressing arenavirus GPs of interest produces the corresponding GP-pseudotyped rLCMVΔGP/GFP that can be used to evaluate antibody responses to HF arenaviruses using a BSL2 platform.

Example 2: Identification of LASV (Josiah Strain) GP-Specific hMAbs that Cross-React with the GP of LCMV ARM Strain Generation of LASV GP-specific hMAbs: Peripheral blood mononuclear cells (PBMCs) isolated from 17 different LF survivors in Sierra Leone and Nigeria were used to identify B cell clones producing specific IgG to LASV GP. RNA from these B cell clones was used to clone the light chain (LC) and heavy chain (HC) genes. Paired LC and HC were expressed in human 293T cells to generate a collection of 120 LASV GP-specific hMAbs. These hMAbs arose from different germline genes and were likely independently derived. All but one (8.9F) of the hMAbs reacted in ELISA with GP from Josiah strain of LASV (lineage IV), which is closely related to the currently circulating LASV strains in Sierra Leone. LASV GP consists of a SSP and GP1 and GP2 subunits, as shown in FIG. 1, Panels A and B. To define the GP subunits recognized by the LASV hMAbs, an immunofluorescence assay was used to test the recognition by hMAbs of human 293T cells expressing either rGP1 or rGP2 alone, or full-length GP, shown in FIG. 1, Panel C. Twenty-nine hMAbs, including three with neutralizing activity, reacted with LASV rGP1, shown by FIG. 1, Panel C, left and Table 1. Fifty-seven hMAbs recognized LASV rGP2 but none of these exhibited neutralizing activity, as shown by FIG. 1, Panel C, middle and Table 1. Seven hMAbs reacted with peptides representing three linear epitopes in GP2, whereas the remaining hMAbs appeared to recognize conformational epitopes. Twenty-seven hMAbs reacted with cells expressing full-length GP but did not react with either rGP1 or rGP2 expressed individually. Remarkably, thirteen of these hMAbs were neutralizing, as shown by FIG. 1, Panel C, right and Table 1. Inhibitory concentration 50 (IC50) and 80 (IC80) neutralizing activity of LASV GP-specific hMAbs was evaluated using lentivirus particles pseudotyped with the different lineage I-IV LASV GPs. Results are shown in Table 1. Based on the data in Table 1, the antibodies can be classified as most potent (hMAbs exhibiting IC values of <1 µg/mL); potent (hMAbs exhibiting IC values in the range of 1 to 2.5 µg/mL), weak (hMAbs exhibiting IC values of >3 and <20 µg/mL); non-neutralizing (hMAbs exhibiting IC values >20 µg/mL).

TABLE 1

Neutralizing activity of LASV GP-specific hMAbs against LASV lineages I-IV.

| Mab | LASV Josiah (IV) | | LASV 237 (III) | | LASV A19 (II) | | LASV Pinneo(I) | |
| --- | --- | --- | --- | --- | --- | --- | --- | --- |
| | IC50 | IC80 | IC50 | IC80 | IC50 | IC80 | IC50 | IC80 |
| 25.10C | 0.094 | 0.174 | 0.058 | 0.180 | 0.104 | 0.364 | 0.226 | 0.564 |
| 12.1F | 0.158 | 0.562 | 0.146 | 0.458 | 0.463 | 2.266 | 0.285 | 0.692 |
| 8.9F | 0.126 | 1.604 | 0.182 | 3.097 | 0.125 | 0.467 | 0.403 | 2.210 |
| 37.2D | 0.559 | 1.983 | 0.256 | 0.844 | 0.469 | 1.154 | 0.537 | 1.861 |
| 37.7H | 0.191 | 0.532 | 0.077 | 0.202 | 0.255 | 0.537 | 0.301 | 1.658 |
| 25.6A | 0.743 | 1.999 | 0.169 | 0.603 | 0.483 | 3.509 | 1.826 | 3.114 |
| 9.8A | 1.309 | 2.423 | 0.193 | 0.494 | 0.150 | 0.527 | 1.003 | 2.587 |
| 18.5C | 1.935 | 3.985 | 0.621 | 3.231 | 1.200 | 4.633 | 6.111 | 12.170 |
| 8.11G | 0.361 | 1.736 | 1.166 | 3.637 | 1.481 | 4.591 | 3.245 | 10.540 |
| 37.2G | 5.599 | 16.000 | 2.020 | 5.231 | 1.100 | 10.000 | >20 | >20 |
| 2.9D | 6.895 | 16.700 | 1.582 | 5.511 | 3.072 | 14.780 | 10.130 | >20 |
| NE13 | 10.680 | 19.500 | 2.136 | 7.000 | 5.409 | 13.180 | >20 | >20 |
| 19.7E | 5.908 | >20 | 1.062 | 15.000 | >20 | >20 | 1.558 | 3.273 |
| 36.9F | 18.000 | >20 | 4.687 | 19.350 | 13.000 | >20 | 6.984 | >20 |
| 36.1F | 0.248 | 0.755 | >20 | >20 | >20 | >20 | >20 | >20 |
| 10.4B | >20 | >20 | >20 | >20 | >20 | >20 | >20 | >20 |

Neutralizing properties of LASV GP-specific hMAbs: The neutralizing properties of the LASV GP-specific hMAbs were evaluated using envelope-deficient core HIV-1 pseudotyped with LASV GP (LASVpp) (shown in Table 1) and standard plaque reduction neutralization test (PRNT) with authentic LASV. Fifteen of the 120 hMAbs neutralized LASVpp expressing GP from Josiah strain of LASV lineage IV, as shown in Table 1. These neutralizing GP-specific hMAbs were also tested against LASVpp containing GP of the three other LASV lineages I-III (shown in Table 1). The IC50 and IC80 values showed that those with the greatest potency and breadth against all four LASV lineages were 25.10C, 12.1F, 8.9F, 37.2D, 37.7H, 25.6A and 8.11G (Table 1). The remaining hMAbs showed weaker and variable potency. Neutralization activity of these GP-specific hMAbs was further confirmed for LASV Josiah strain using a LCMV-based pseudovirus assay. These results revealed that out of the 120 tested LASV GP-specific hMAbs, 15 neutralized to different degrees LASV Josiah strain, and some of them exhibited broad neutralizing activity against representative strains from LASV lineages I-II.

Cross-reactivity of LASV GP-specific hMAbs with LCMV ARM: The 16 LASV GP-specific hMAbs with neutralizing activity (as shown in Table 1) were characterized with respect their ability to recognize LCMV ARM strain GP expressed in human 293T cells transfected with GP-expressing plasmids by immunofluorescence. Human 293T cells transfected with LASV GPs from lineages I-IV were included as controls. Nine of the LASV GP-specific neutralizing hMAbs (12.1F, 37.7H, 37.2D, 25.6A, 9.8A, 18.5C, 37.2G, 2.9D and 36.9F) cross-reacted with LCMV ARM GP.

Example 3: Identification of LASV GP-Specific hMAbs with Broad Cross-Reactivity Against GPs from Different LCMV Strains The ability of LASV GP-specific neutralizing hMAbs (as shown by FIG. 1 and Table 1) to recognize GPs from five LCMV strains associated with human cases of LCMV-induced disease was examined. These strains corresponded to the WE strain that caused a zoonotic infection in New York in 1935; Rhode Island (RI) strain, responsible for four human cases and three fatalities from a transplant case in 2005; Ohio (OH) strain that is similar to the Michigan LCMV strain responsible for a human case in 2005; Wisconsin (WI) strain responsible for four human deaths in 2003; and Massachusetts (MA) strain, responsible for two human deaths in 2008. LASV GP-specific neutralizing hMAbs 12.1F, 37.2D, 9.8A, 18.5C and 36.9F recognized all five LCMV GP strains. LASV GP-specific neutralizing hMAbs 37.7H, 25.6A, 37.2G and 2.9D recognized four LCMV strains (ARM, WE, WI, and MA, but not RI or AH). The rest of the hMAbs did not cross-react with any of the LCMV strains tested.

Figure 2:
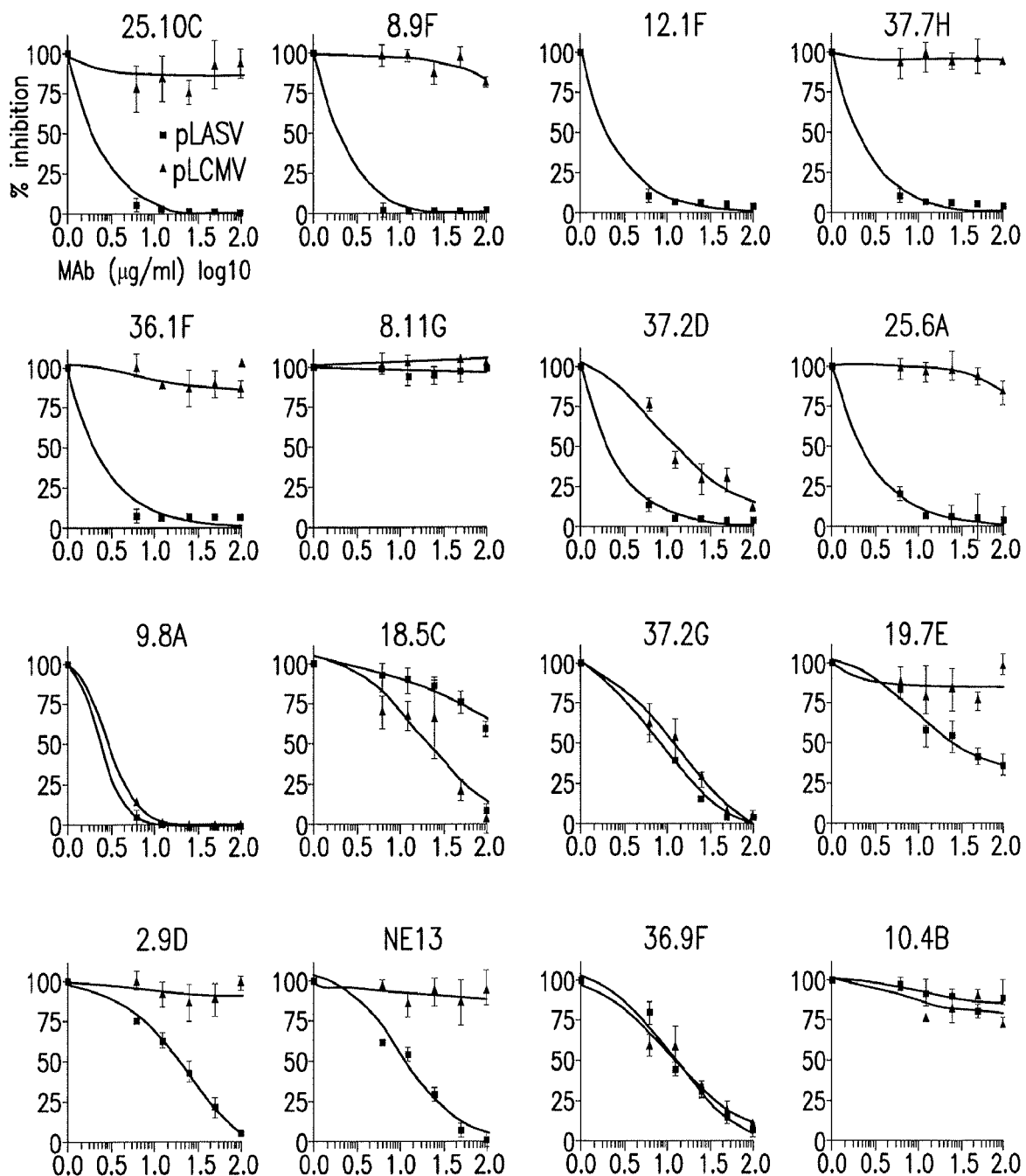
FIG. 2 depicts in vitro neutralization of LCMV ARM with the 15 LASV GP-specific neutralizing hMAbs: LASV Josiah (squares) and LCMV ARM (triangles) GP-pseudotyped rLCMVΔGP/GFP viruses were incubated for 90 min at 37° C. with a 2-fold dilution of the indicated LASV GP-specific BNhMAb before infecting LCMV GP-expressing Vero cells (96 plate format, triplicates). Virus neutralization was determined under a fluorescent microscope and quantified using a GFP microplate reader at 72 hours post-infection. Results are presented as percent inhibition after normalizing to respective viral infections in the absence of hMAbs. Virus infection in the absence of hMAbs was used as internal control. Mean values and standard deviation are shown. Standard error was calculated based on 2-6 replicates.

Example 4: Identification of LASV GP-Specific hMAbs with Strong Broadly Neutralizing Activity (BNhMAbs) Against GPs from Different LCMV Strains in Cell-Based Assays A validated cell-based microneutralization assay was used to identify LASV GP-specific hMAbs that not only cross-reacted with different LCMV GPs, but also neutralized LCMV ARM, as they would represent primary candidates to display broadly antiviral activity in vivo against LCMV strains previously associated with disease cases in humans. From the 15 LASV GP-specific neutralizing hMAbs, six of them (12.1F, 37.2D, 9.8A, 18.5C, 37.2G and 36.9F) neutralized LCMV ARM, as shown in FIG. 2, with IC50<1 µg/mL, with the exception of 18.5C that exhibited a higher (>10 µg/mL) IC50. Results are displayed in Table 2, which shows the neutralizing activity of the 15 LASV GP-specific neutralizing hMAbs against LCMV ARM, and in particular, the IC50 and IC80 values of the 15 LASV GP-specific neutralizing hMAbs against LCMV ARM. Values were obtained from the cell-based microneutralization assay (shown in FIG. 2) using LASV or LCMV GP-pseudotyped rLCMVΔGP/GFP viruses. Grey indicates LASV GP-specific neutralizing hMAbs that neutralized LCMV GP ARM. Neutralization of LASV GP-pseudotyped rLCMVΔGP/GFP was similar to neutralization results obtained using the LASV GP-pseudotyped lentivirus particles shown in Table 1.

TABLE 2

Neutralizing activity of 15 LASV GP-specific neutralizing hMAbs against LCMV Armstrong strain (ARM).

| | LASV Josiah (IV) | | LCMV ARM | |
| --- | --- | --- | --- | --- |
| hMAb | IC50 | IC80 | IC50 | IC80 |
| 25.10C | 0.160 | 0.247 | >10 | >10 |
| 12.1F | 0.172 | 0.258 | 0.167 | 0.265 |
| 8.9F | 0.134 | >10 | >10 | >10 |
| 37.2D | 0.137 | 0.260 | 0.518 | 2.358 |
| 37.7H | 0.134 | 0.214 | >10 | >10 |
| 25.6A | 0.188 | 0.300 | >10 | >10 |
| 9.8A | 0.139 | 0.253 | 0.112 | 0.248 |
| 18.5C | >10 | >10 | 2.207 | 4.83 |
| 8.11G | >10 | >10 | >10 | >10 |
| 37.2G | 0.405 | 1.776 | 0.525 | 2.461 |
| 2.9D | 0.942 | 2.706 | >10 | >10 |
| NE13 | 0.567 | 1.763 | >10 | >10 |
| 19.7E | 1.189 | >10 | >10 | >10 |
| 36.9F | 0.570 | 2.228 | 0.591 | 3.328 |
| 36.1F | 0.132 | 0.206 | >10 | >10 |
| 10.4B | >10 | >10 | >10 | >10 |

Example 5: In Vivo Characterization of Selected GP-Specific BNhMAb

Figure 3:
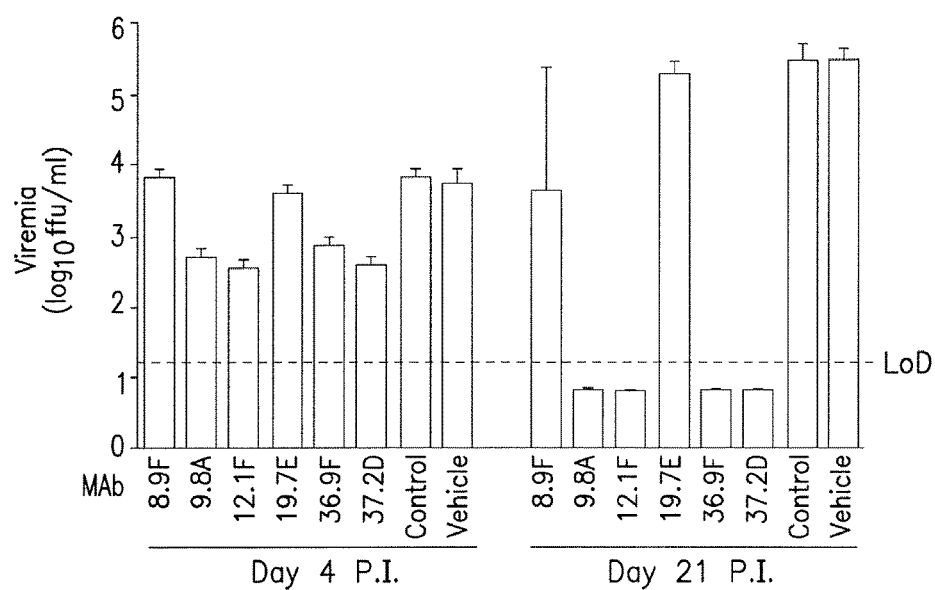
FIG. 3 depicts in vivo neutralization of the 6 LCMV neutralizing antibodies (12.1F, 9.8A, 37.2D, 36.9F, 37.2G, and 18.5C) using the non-crossreactive antibodies 19.7E and 8.9F as internal controls. Mice were infected with rCl-13 (2×106 pfu; i.v.) and treated with the indicated hMAb (20 mg/kg; i.p.), as well as an isotype hMAb control (20 mg/kg, i.p.) or vehicle. At days 4 and 21, post inoculation (p.i.) viremia (i.e., the presence of viruses in the blood) was determined. Results correspond to the average and standard deviation (SD) of four mice/group; LoD=limit of detection.

The well-characterized mouse model of LCMV infection was used to test whether LASV GP-specific neutralizing hMAbs with broadly neutralizing activity against LCMV (shown in FIG. 2 and Table 2) also exhibited in vivo neutralizing activity. The immunosuppressive Clone 13 (Cl-13) strain of LCMV was used. Infection (i.v.) of B6 WT mice with a high dose ($\geq 10^6$ PFU) of Cl-13 results in transient generalized immunosuppression and establishment of a persistent infection with well-established parameters. Virus clearance takes place between days 60 to 100 (post inoculation (p.i.). However, treatment of Cl-13 infected mice that results in reduced viral load accelerates Cl-13 clearance. Therefore, it was predicted that LASV GP-specific neutralizing hMAbs exhibiting in vivo neutralizing activity would either prevent the establishment of Cl-13 persistence or accelerate its clearance. Mice were treated with the indicated hMAbs at 20 mg/Kg intraperitoneally (i.p.) and were infected with either rCl-13/WT or rCl-13/LASV-GP(mCD). rCl-13/LASV-GP(mCD) was used because it contains mutations C459K and K461G within the cytosolic domain of GP that enhance persistence in mice. The in vivo results are shown in FIG. 3 and correlate with those previously documented in cultured cells (shown in FIG. 2 and Table 2). Mice treated with hMAbs 12.1F, 37.2D, 9.8A and 36.9F prevented persistence of rCl-13/WT. Unexpectedly, hMAbs 37.2G and 18.5C did not prevent Cl-13 persistence in vivo. As expected, based on cross-reactivity and neutralization results in cultured cells, hMAbs 19.7E and 8.9F did not prevent persistence of rCl-13.

Table 3 displays a summary of the cross-reactivity and neutralizing activity in vitro and in vivo of LASV GP-specific hMAbs against six LCMV strains (ARM, WE, RI, OH, WI, and MA) tested.

The advantage of using outbred animals to model human infection is inferred from the higher variability of immune responses inherent in outbred populations. Viremia was compared by Kruskal-Wallis test supported by Dunn's Multiple comparison posttest (PRISM 5™ software available from GraphPad Software, La Jolla, Calif.) to detect differences from the control group for time points relevant to onset (day 7) or peak viremia (day 14) as determined from historical data.

TABLE 3

Summary of the cross-reactivity and neutralizing activity in vitro and in vivo of LASV GP-specific hMAbs against LCMV.

| | Cross-reactivity | | | | | | Neutralizing activity | |
|---|---|---|---|---|---|---|---|---|
| | $LCMV_{ARM}$ | $LCMV_{WE}$ | $LCMV_{RI}$ | $LCMV_{OH}$ | $LCMV_{WI}$ | $LCMV_{MA}$ | In vitro | In vivo |
| 25.10C | − | − | − | − | − | − | − | − |
| 8.9F | − | − | − | − | − | − | − | − |
| 12.1F | + | + | + | + | + | + | + | + |
| 37.7H | + | + | − | − | + | + | − | − |
| 36.1F | − | − | − | − | − | − | − | − |
| 8.11G | − | − | − | − | − | − | − | − |
| 37.2D | + | + | + | + | + | + | + | + |
| 25.6A | + | + | − | − | + | + | − | − |
| 9.8A | + | + | + | + | + | + | + | + |
| 18.5C | − | − | − | − | − | − | + | − |
| 37.2G | + | + | − | − | + | + | + | − |
| 19.7E | − | − | − | − | − | − | − | − |
| 2.9D | + | + | − | − | + | + | − | − |
| NE13 | − | − | − | − | − | − | − | − |
| 36.9F | + | + | + | + | + | + | + | + |
| 10.4B | − | − | − | − | − | − | − | − |

Example 6: Assay Development

A panel of murine antibodies against Fab or F(ab')2 fragments of leading candidate therapeutic BNhMAbs was derived for isolation of highly specific anti-idiotypic reagents for assay development. In order to develop a highly protective therapeutic BNhMAb cocktail containing two to four antibodies that together confer maximum pre- and post-exposure protection against LCMV infections, while minimizing the emergence of escape mutants, it is important to characterize the PK of each antibody when administered in a cocktail form. To distinguish between all BNhMAbs included in the cocktail after administration, highly specific anti-idiotypic antibodies are the best tool available to rapidly determine concentration and clearance of individual hMAbs from the blood. A panel of anti-idiotypic antibodies to 37.2D and 12.1F has been developed. Anti-idiotypic mMAbs to 37.2D have specifically detected this BNhMAb when spiked into human serum. The anti-idiotypic antibodies do not capture or detect any other arenaviral BNhMAb tested or any other IgG specificity present in human serum on both ELISA and SPR based studies, and thus are useful for assaying 37.2D.

Example 7: Therapeutic Efficacy of First-in-Class Human LASV-Specific Antibodies in Guinea Pig (GP) and Cynomolgus Macaque (CM) Models of Lassa Fever These studies were done under BSL-4 biocontainment at the Galveston National Laboratory. Outbred Hartley strain GP were challenged i.p. with 1,000 pfu of GP adapted (GPA) LASV Josiah strain (N=5/group). This model has been described recently for testing therapeutics against LASV.

Eleven LASV hMAbs tested in a Hartley GP model of LF segregated into three distinct protection groups: (1) 25.6A, 2.9D, 8.9F, 12.1F, and 37.7H conferred 100% protection and no change in clinical score in GPs. (2) 37.2D, 19.7E, and 37.2G protected 80 to 90% of animals. (3) 10.4B, 25.10C, and 36.1F, conferred 40%, 30%, and 20% protection, respectively. An irrelevant recombinant human isotype control (IgG1) Ab did not confer protection (0% survival).

Figure 4:
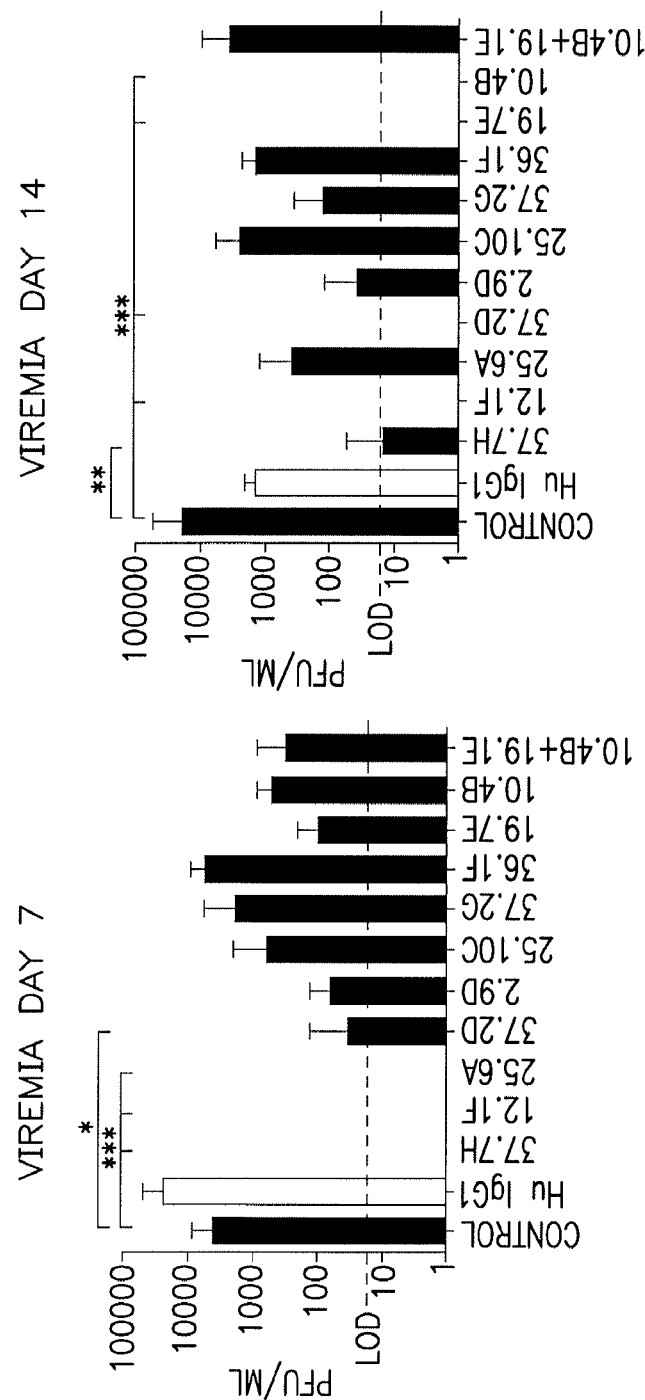
FIG. 4 illustrates Viremia data from treated and control GP plasma on days 7 and 14 PI. Viremia levels for day 7 treatment groups 37.7H, 12.1F, and 25.6A as well as day 14 12.1F, 37.2D, 19.7E, and 10.4B were below the limit of detection (LOD). Error bars represent standard deviation from mean values. *denotes P_0.05. denotes P_0.001. *denotes P<0.0001.
Figure 5A:
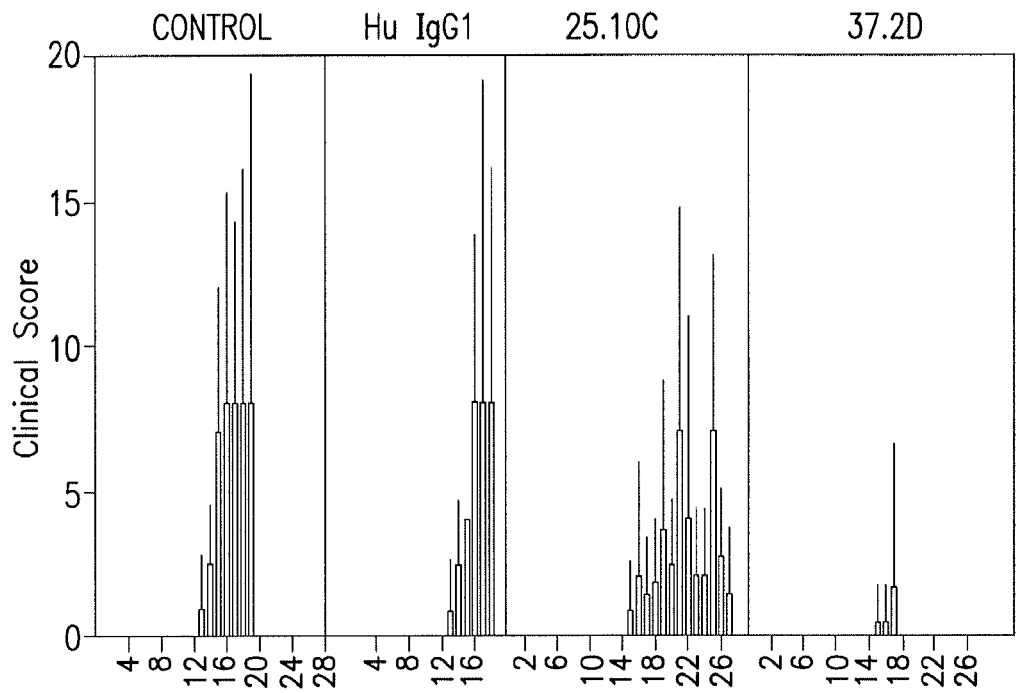
FIG. 5 depicts clinical scores of HuMAb treated and untreated guinea pigs. HuMAbs 8.9F and 12.1 treated GP showed no variation in clinical score from baseline (data not shown). Error bars (thin lines) represent standard deviation from mean values.
Figure 5B:
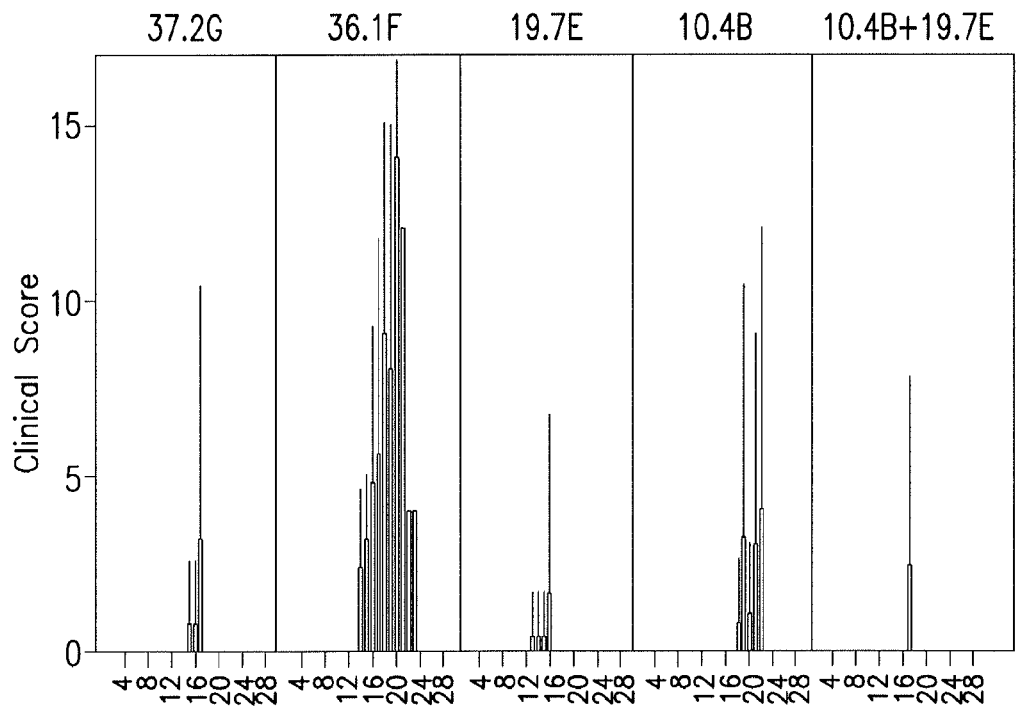

With respect to viremia, untreated control animals averaged 3.5 and 4.5 Log PFU/mL on days 7 and 14, respectively, as shown in FIG. 4. Despite 100% protection at the study endpoint, some animals from treatment group 8.9F or 37.7H, 2.9D, and 25.6A had low level viremia on day 7 or 14, respectively. Treatment groups where 90% protection was afforded (37.2D and 19.7E) had reduced mean viremia titers and minimal clinical score values. Treatment groups with 80% or less survival had comparable mean viremia titers to control animals on day 7, but by day 14 mean viremia was markedly lower than control animals. Groups with 80 to 90% survival exhibited relatively low mean clinical scores (FIG. 5) and all remaining treatment groups exhibited concomitant increases in mean clinical scores with decreases in survival per group. Endpoint viremia was not determined for these studies as survival was the primary metric of interest, though all surviving animals demonstrated no clinical signs.

Results from the guinea pig studies informed studies for the Cynomolgus macaque (CM) model of LF. These studies demonstrated that several of the antibodies with high potency in the GP model also protected 100% of the CMs when administered on the day of challenge. 19.7E protected 75% of CMs. Notably a treatment dose as low as 6 mg/kg of hMAb 37.2D provided 100% protection in CMs, whereas 19.7E protected 75% of CMs. A cocktail of three human MAbs (37.2D, 12.1F, and 8.9F at 15 mg/kg each) rescued 100% of CMs even after delay in the start of treatment to 3, 6, or 8 days post-infection (therapeutic walk-out studies). At 8 days post-infection, untreated CMs had developed high viral loads and were extremely ill. CM also were protected from lethal LF induced by challenge with either strain Josiah (lineage IV) or a contemporary lineage II strain derived from a lethal case of LF in Nigeria, both with the first treatment administered at 8 days post-infection.

Example 8: Structural Definition of the Anti-LASV 37.711 Epitope

Monomeric GPCysR4 was incubated with excess Fab 37.7H and subjected to SEC-MALS analysis. SEC-MALS indicated the formation of trimeric GP-Fab complexes in addition to monomeric GP-Fab complexes. Crystals of both the monomeric and trimeric fractions of the GPCysR4-Fab 37.7H complex formed in space group P6122 and diffract to 3.2 Å with a trimer of GP bound to three Fabs in the asymmetric unit. Phases were determined with an iterative approach by using molecular replacement with a related Fab structure and the LCMV GP crystal structure.

The antibody 37.7H against LASV neutralizes viruses representing all four known lineages of LASV in vitro and offers protection from lethal LASV challenge in guinea pig and nonhuman primates. The antibody simultaneously binds two GP monomers at the base of the GP trimer, where it engages four discontinuous regions of LASV GP, two in "site A" and two in "site B". Site A contains residues 62 to 63 of the N-terminal loop of GP1 and residues 387 to 408 in the T-loop and HR2 of GP2. Site B contains residues 269 to 275 of the fusion peptide and residues 324 to 325 of HR1 of GP2. In total, 37.7H buries about 1620 Å$^2$ of GP: about 1000 Å$^2$ of GP at site A and about 620 Å$^2$ of GP at site B. Although nearly the entire surface buried on GP belongs to GP2, the presence of both GP1 and GP2 is critical for 37.7H recognition, likely because GP1 is required to maintain the proper prefusion conformation of GP2 for 37.7H binding.

The antibody 37.7H also recognizes the GPC of LCMV but does not recognize the GPC of the more distantly related Old World arenavirus LUJV nor the GPC of New World arenaviruses. A sequence comparison among these arenaviruses demonstrates nearly complete sequence conservation throughout the 37.7H epitope for all LASV lineages and LCMV. However, the sequences of LUJO, JUNV, and MACV GPCs are far more divergent, particularly in HR2 of GP2, which is heavily involved in binding to 37.7H. The 37.7H antibody neutralizes by stabilizing the prefusion GP.

The quaternary nature and the involvement of the fusion peptide in the 37.7H epitope suggest that this antibody neutralizes the virus by stabilizing GPC in the prefusion conformation, thereby preventing the conformational changes required for infection. This was verified by analyzing the ability of LASV GP-pseudotyped recombinant vesicular stomatitis virus (rVSV-LASV GP) to mediate fusion with cell membranes.

First the ability of 37.7H to neutralize rVSVLASV GP was determined. FIG. 6 shows the effect of antibodies on rVSV-LASV GP infection and fusion. Antibody-mediated neutralization of rVSV-LASV GP is shown in FIG. 6, Panel A. Antibody-mediated neutralization of rVSV-VSV-G is shown in FIG. 6, Panel B. The antibody 9.7 Å is non-neutralizing antibody and in the same competition group as 37.7H (GPC-B); 13.4E binds to a linear epitope in the T-loop of GP2; 12.1F binds to the GP1 subunit of LASV. Error bars indicate the standard deviation of at least six (two biological replicates, each having three or more technical replicates). FIG. 6, Panel C shows antibody-mediated inhibition of rVSVLASV GP fusion at the cell surface. Error bars indicate the standard error of the mean of six (except 37.7H, where N=9). FIG. 6, Panel D shows Fab 37.7H reduces binding of a LAMP1-Fc fusion protein to LASV GPCysR4. Error bars indicate the standard deviation of six and three technical replicates.

37.7H effectively prevented cellular infection by rVSV-LASV GP, as did the antibody 12.1F, which binds to the upper, β-sheet face of LASV GP1 and is presumed to block cell attachment. In contrast, antibodies 13.4E, which binds a linear epitope in the T-loop, and 9.7A, which is a non-neutralizing GPC-B antibody, did not prevent viral infection (FIG. 6, Panels A and B).

Next, the ability of 37.7H to prevent fusion of rVSV-LASV GP with cell membranes when exposed to low pH was examined. Unlike the non-neutralizing antibodies 9.7 Å and 13.4E, which were not effective in preventing fusion, 37.7H reduced fusion by nearly 80% compared with rVSV-LASV GP alone (FIG. 6, Panel C). In contrast, the neutralizing antibody against GP1 (anti-GP1), 12.1F, showed only a slight reduction in infectivity, suggesting that the effect of 37.7H was strictly due to disruption in fusogenicity of the GPC and not attachment to cells.

Before exposure of the GP2 fusion peptide and loop and subsequent fusion of the viral and host cell membranes, LASV GP1 engages LAMP1. Engagement of this receptor is thought to require conformational changes in GP1 that are triggered by exposure to the low pH in the endosome. Tomography of LASV spikes in the presence of low pH and LAMP1 shows an opening of the trimer compared with its neutral pH conformation. To determine whether 37.7H could prevent these conformational changes, the ability of GPCysR4 to bind to a soluble LAMP1-Fc fusion alone and when bound to Fab 37.7H was analyzed. In the absence of Fab 37.7H, GPCysR4 effectively bound to LAMP1 when exposed to low pH. In the presence of Fab 37.7H, however, interaction between GPCysR4 and LAMP1 was markedly reduced (FIG. 6, Panel D).

Based on crystallographic data, the footprint of 37.7H and the footprint of LAMP1 are separated by about 50 Å, and the angle adopted by the bound Fab fragments of 37.7H suggests that it is unlikely to sterically interfere with LAMP1. Thus, there are likely to be conformational changes in GP1 required for LAMP1 binding that are prevented by this human survivor antibody. Taken together, these results demonstrate that the probable mechanism of action for 37.7H and probably for other antibodies in its potent GPC-B competition group is stabilization of the prefusion GPC trimer and prevention of the conformational changes required for binding of LAMP1 and triggering of the GP2 fusion peptide and fusion loop in the endosome.

Other embodiments and uses of the invention will be apparent to those skilled in the art from consideration of the specification and practice of the invention disclosed herein. All references cited herein, including all publications, U.S. and foreign patents and patent applications, are specifically and entirely incorporated by reference. It is intended that the specification and examples be considered exemplary only with the true scope and spirit of the invention indicated by the claims.

The following reference articles are incorporated herein by reference.

REFERENCES

1. Auperin, D. D., Sasso, D. R. and McCormick, J. B. (1986). Nucleotide sequence of the glycoprotein gene and intergenic region of the Lassa virus S genome RNA. Virology 154, 155-167.
2. Beyer, W. R., Popplau, D., Garten, W., von Laer, and Lenz 0. (2003). Endoproteolytic processing of the lymphocytic choriomeningitis virus glycoprotein by the sibtilase SKI-1/S1P. J. Virol. 77, 2866-2872.
3. Buchmeier, M. J. (2002). Arenaviruses: protein structure and function. Curr. Top. Microbiol. Immunol. 262, 259-173.
4. Buchmeier, M. J., and Parekh, B. S. (1987). Protein structure and expression among arenaviruses. Current Topics in Microbiology and Immunology 133, 41-57.
5. Buchmeier, M. J., Lewicki, H. A., Tomor, O., and Jonhson, K. M. (1980). Monoclonal antibodies to lymphocytic choriomeningitis virus reacts with pathogenic arenaviruses. Nature, London 288, 4876-4877.
6. Burnette, W. N. (1981). "Western Blotting": electrophoretic transfer of proteins from sodium dodecyl sulfate-polyacrylamide gels to unmodified nitrocellulose and radiographic detection with antibody and radioiodinated protein A. Analytical Biochemistry 112, 195-203.
7. Clegg, J. C. and Lloyd, G. (1983). Structureal and cell-associated proteins of Lassa virus. Journal of General Virology 64, 1127-1136.
8. Eichler, R., Lenz, O., Strecker, T., Eickmann, M., Klenk, H. D., and Garten, W. (2004). Lassa virus glycoprotein signal peptide displays a novel topology with an extended ER-luminal region. J. Biol. Chem. 279, 12293-12299.
9. Eichler, R., Lenz, O., Strecker, T., Eickmann, M., Klenk, H. D., and Garten, W. (2003). Identification of Lassa virus glycoprotein signal peptide as a trans-acting maturation factor. EMBO Rep. 4, 1084-1088.
10. Eichler, R., Lenz, O., Strecker, T., Eickmann, and Garten, W. (2003). Signal peptide of Lassa virus glycoprotein GP-C exhibits an unusual length. FEBS Lett. 538, 203-206.
11. Elagoz, A., Benjannet, S., Mammarbassi, A., Wickham, L., and Seidah, N. G. (2002). Biosynthesis and cellular trafficking of the convertase SKI-1/S1P: ectodomain shedding requires SKI-1 activity. J. Biol. Chem. 277, 11265-11275.
12. Hufert, F. T., Ludke, W., and Schmitz, H. (1989). Epitope mapping of the Lassa virus nucleocapsid protein using monoclonal anti-nucleocapsid antibodies. Archives of Virology 106, 201-212.
13. Lenz, O., ter Meulen, J., Feldmann, H., Lenk, H.-D., and Garten, W. (2000). Identification of a novel consensus sequence at the cleavage site of the Lassa virus glycoprotein. J. Virol. 74, 11418-11421.
14. Lukashevich L. S., Clegg J. C., and Sidibe K. (1993). Lassa virus activity in Guinea: distribution of human antiviral antibody defined using enzyme-linked immunosorbent assay with recombinant antigen. J Med Virol. 40, 210-7.
15. McCormick, J. B., and Fisher-Hoch, S. P. (2002). Lassa Fever. Curr. Top. Microbiol. Immunol. 262, 75-109.
16. Ruo, S. L., Mitchell, S. W., Killey, M. P., Roumillat, L. F., Fisher-Hoch, S. P., and McCormick, J. B. (1991). Antigenic relatedness between arenaviruses defined at the epitope level by monoclonal antibodies. Journal of General Virology 72, 549-555.
17. Sanchez, A., Pifat, D. Y., Kenyon, R. H., Peters, C. J., McCormick, J. B., and Kiley, M. P. (1989). Junin virus monoclonal antibodies: characterization and cross-reactivity with other arenaviruses. J. Gen. Virol. 70, 1125-1132.
18. Spiropoulou, C. F., Kunz, S., Rollin, P. E., Campbell, K. P., and Oldstone, M. B. A. (2002). New World arenavirus clade C, but not clade A and B viruses, utilizes a-dystroglycan as its major receptor. J. Virol. 76, 5140-5146.
19. ter Meulen J., Badusche M., Kuhnt K., Doetze A., Satoguina J., Marti T., Loeliger C., Koulemou K., Koivogui L., Schmitz H., Fleischer B., and Hoerauf A. (2000). Characterization of human CD4(+) T-cell clones recognizing conserved and variable epitopes of the Lassa virus nucleoprotein. J. Virol. 74, 2186-92.
20. ter Meulen, J., Koulemou K., Wittekindt T., Windisch K., Strigl S., Conde S., and Schmitz H. (1998). Detection of Lassa Virus Antinucleoprotein Immunoglobulin G (IgG) and IgM Antibodies by a Simple Recombinant Immunoblot Assay for Field Use. J. Clin. Microbiol. 36, 3143-3148.
21. York, J., Agnihothram, S. S., Ronamowski, V., and Nunberg, J. H. (2005). Genetic analysis of heptad-repeat regions in the G2 fusion subunit of the Junin arenavirus envelope glycoprotein. Virology 343, 267-279.
22. York, J., Ronamowski, V., Lu, M., and Nunberg, J. H. (2004). The signal peptide of the Junin arenavirus envelope glycoprotein is myristoylated and forms an essential subunit of the mature G1-G2 complex. J. Virol. 78, 10783-10792.
23. Shaffer J G, Grant D S, Schieffelin J S, Boisen M L, Goba A, et al. 2014. Lassa Fever in Post-Conflict Sierra Leone. *PLoS Negl Trop Dis* 8: e2748.
24. Hartnett J N, Boisen M L, Oottamasathien D, Jones A B, Millett M M, . . . Garry R F, Branco L M & the VHFC (2015). Current and emerging strategies for the diagnosis, prevention and treatment of Lassa fever. Future *Virology. Review.* Vol. 10, No. 5, Pages 559-584.
25. Andersen K G, Shapiro B J, Matranga C B, Sealfon R, Lin A E, . . . Branco L M, Gire S K, Phelan E, Tariyal R, Tewhey R, . . . Garry R F, Sabeti P C. Clinical Sequencing Uncovers Origins and Evolution of Lassa Virus. *Cell.* 2015 Aug. 13; 162(4):738-50.
26. Luis M Branco, Jessica N Grove, Matt L Boisen, Jeffrey G Shaffer, Augustine Goba, . . . Robert F Garry. Emerging trends in Lassa fever: redefining the role of immunoglobulin M and inflammation in diagnosing acute infection. *Virology Journal* 2011, 8:478 (24 Oct. 2011).
27. Jessica N Grove, Luis M Branco, Matt L Boisen, Ivana J Muncy, Lee A Henderson, . . . Robert F Garry. Capacity building permitting comprehensive monitoring of a severe case of Lassa hemorrhagic fever in Sierra Leone with a positive outcome: Case Report. *Virology Journal* 2011, 8:314 (20 Jun. 2011).
28. Luis M Branco, Jessica N Grove, Frederick J Geske, Matt L Boisen, Ivana J Muncy, . . . Robert F Garry. Lassa virus-like particles displaying all major immunological determinants as a vaccine candidate for Lassa hemorrhagic fever. *Virology Journal* 2010, 7:279 (20 Oct. 2010).
29. Luis M Branco, Matt L Boisen, Kristian G Andersen, Jessica N Grove, Lina M Moses, . . . Robert F Garry. Lassa Hemorrhagic Fever in a Late Term Pregnancy from Northern Sierra Leone with a Positive Maternal Outcome: Case Report. *Virology Journal* 2011, 8:404 (15 Aug. 2011).

What is claimed is:

1. An antigen-binding composition comprising a neutralizing human monoclonal antibody or neutralizing antigen-binding antibody fragment thereof specific to glycoprotein 1 (GP1), glycoprotein precursor (GPC), or full-length glycoprotein (GP) of Lassa virus (LASV), wherein the antibody or antibody fragment comprises a heavy chain variable region ($V_H$) and a light chain variable region ($V_L$), the $V_H$ and $V_L$ each comprising the following complementarity determining regions: a $V_H$ CDR1 of SEQ ID NO: 98, a $V_H$ CDR2 of SEQ ID NO: 99, a $V_H$ CDR3 of SEQ ID NO: 100, a $V_L$ CDR1 of SEQ ID NO: 135, a $V_L$ CDR2 of sequence Gly Ala Ser, and a $V_L$ CDR3 of SEQ ID NO: 136.

2. The composition of claim 1, wherein the composition comprises two or more of said antibodies or antigen-binding antibody fragments.

3. The composition of claim 1, wherein the antibody comprises a human monoclonal antibody.

4. The composition of claim 1, wherein the antigen-binding antibody fragment is selected from the group consisting of a Fab, a Fab', and a F(ab')$_2$ fragment.

5. An antigen-binding composition comprising a neutralizing human monoclonal antibody or neutralizing antigen-binding antibody fragment thereof specific to glycoprotein 1 (GP1), glycoprotein precursor (GPC), or full-length glycoprotein (GP) of Lassa virus (LASV), wherein the antibody or antibody fragment comprises the following heavy chain variable region ($V_H$) and light chain variable region ($V_L$): a $V_H$ of SEQ ID NO: 44 and a $V_L$ of SEQ ID NO: 60.

6. The composition of claim 5, wherein the composition comprises two or more of said antibodies or antigen-binding antibody fragments.

7. The composition of claim 5, wherein the antibody comprises a human monoclonal antibody.

8. The composition of claim 5, wherein the antigen-binding antibody fragment is selected from the group consisting of a Fab, a Fab', and a F(ab')$_2$ fragment.

9. A pharmaceutical composition for treating infection by a Lassa virus or lymphocytic choriomeningitis virus comprising the antibody or antibody fragment of the composition of claim 1 and a pharmaceutically acceptable carrier.

10. A diagnostic kit for detecting infection of a subject by Lassa virus or lymphocytic choriomeningitis virus comprising at least one antibody or antibody fragment of the composition of claim 1 bound to a detectable labelling group and packaged in a container; wherein the container is selected from the group consisting of a vial, a bottle, a jar, and a flexible packaging container.

11. An antibody or antibody fragment of the composition of claim 1 bound to a detectable labelling group.

12. A method of treating or preventing infection by a Lassa virus in a subject comprising administering the antibody or antibody fragment of the composition of claim 1 to the subject.

13. A method of treating a lymphocytic choriomeningitis virus infection in a subject comprising administering the antibody or antibody fragment of the composition of claim 1 to the subject.

* * * * *